US012692263B2

(12) United States Patent
Wang et al.

(10) Patent No.: US 12,692,263 B2
(45) Date of Patent: Jul. 28, 2026

(54) SOS1 INHIBITORS AND USES THEREOF

(71) Applicant: QILU REGOR THERAPEUTICS INC., Shanghai (CN)

(72) Inventors: Kailiang Wang, Shanghai (CN); Zhilong Hu, Shanghai (CN); Fei Zhang, Shanghai (CN); Wei Huang, Shanghai (CN); Teng Feng, Shanghai (CN); Fei Xiao, Shanghai (CN); Wenge Zhong, Thousand Oaks, CA (US)

(73) Assignee: QILU REGOR THERAPEUTICS INC., Shanghai (CN)

( * ) Notice: Subject to any disclaimer, the term of this patent is extended or adjusted under 35 U.S.C. 154(b) by 486 days.

(21) Appl. No.: 18/268,914

(22) PCT Filed: Dec. 21, 2021

(86) PCT No.: PCT/US2021/064668

§ 371 (c)(1),
(2) Date: Jun. 21, 2023

(87) PCT Pub. No.: WO2022/140427

PCT Pub. Date: Jun. 30, 2022

(65) Prior Publication Data

US 2024/0051956 A1 Feb. 15, 2024

(30) Foreign Application Priority Data

Dec. 22, 2020 (WO) ................ PCT/CN2020/138288

(51) Int. Cl.

| | |
|---|---|
| *C07D 471/04* | (2006.01) |
| *A61P 35/00* | (2006.01) |
| *C07D 519/00* | (2006.01) |

(52) U.S. Cl.

CPC ............ *C07D 471/04* (2013.01); *A61P 35/00* (2018.01); *C07D 519/00* (2013.01)

(58) Field of Classification Search

CPC .. C07D 471/04; C07D 519/00; C07D 471/14; A61P 35/00; A61K 31/519; A61K 31/5377; A61K 45/06

See application file for complete search history.

(56) References Cited

U.S. PATENT DOCUMENTS

| | | | |
|---|---|---|---|
| 2004/0038959 | A1 | 2/2004 | Bunker et al. |
| 2018/0334454 | A1 | 11/2018 | Lanman et al. |

FOREIGN PATENT DOCUMENTS

| | | | | |
|---|---|---|---|---|
| WO | 1999/61444 | A2 | 12/1999 | |
| WO | 1999/64400 | A1 | 12/1999 | |
| WO | 2018/119183 | A2 | 6/2018 | |
| WO | WO-2019122129 | A1 * | 6/2019 | ............. A61P 35/00 |
| WO | 2019/201848 | A1 | 10/2019 | |
| WO | 2019/191470 | A1 | 12/2019 | |
| WO | 2020/063860 | A1 | 4/2020 | |
| WO | 2020/180770 | A1 | 9/2020 | |

OTHER PUBLICATIONS

International Search Report and Written Opinion for Application No. PCT/US2021/064668, dated Mar. 4, 2022, 8 pages.

* cited by examiner

*Primary Examiner* — Kamal A Saeed
*Assistant Examiner* — Meghan C Heasley
(74) *Attorney, Agent, or Firm* — McCarter & English, LLP; Yu Lu; Wei Song

(57) ABSTRACT

The present disclosure provides a compound of Formula (I) a pharmaceutically acceptable salt or a stereoisomer and their use in, e.g. treating a condition, disease or disorder in which the inhibition of the interaction of SOS 1 and a RAS-family protein or RAC1 is of therapeutic benefit, specifically in treating oncological diseases. This disclosure also features compositions containing the same as well as methods of using and making the same.

(I)

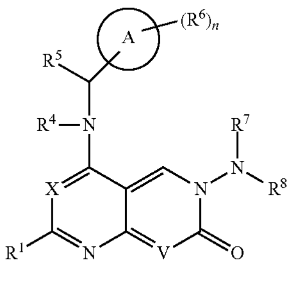

20 Claims, No Drawings

SOS1 INHIBITORS AND USES THEREOF

CROSS-REFERENCE TO RELATED APPLICATIONS

This application is a 35 U.S.C. § 371 national stage filing of International Application No. PCT/US2021/064668, filed on Dec. 21, 2021, which in turn claims the benefit of priority to International Patent Application No. PCT/CN2020/138288, filed on Dec. 22, 2020. The entire contents of each of the aforementioned applications are incorporated herein by reference.

BACKGROUND

RAS-family proteins including KRAS (V-Ki-ras2 Kirsten rat sarcoma viral oncogene homolog), NRAS (neuroblastoma RAS viral oncogene homolog), and HRAS (Harvey murine sarcoma virus oncogene) and any mutants thereof are small GTPases that exist in cells in either GTP-bound or GDP-bound states (McCormick et al., J. Mol. Med. (Berl)., 2016, 94(3):253-8; Nimnual et al., Sci. STKE., 2002, 2002 (145):pe36). The RAS-family proteins have a weak intrinsic GTPase activity and slow nucleotide exchange rates (Hunter et al., Mol. Cancer Res., 2015, 13(9): 1325-35). Binding of GTPase activating proteins (GAPs) such as NF1 increases the GTPase activity of RAS-family proteins. The binding of guanine nucleotide exchange factors (GEFs) such as SOS1 (Son of Sevenless 1) promotes release GDP from RAS-family proteins, enabling GTP binding (Chardin et al., Science, 1993, 260(51 12):1338-43). When in the GTP-bound state, RAS-family proteins are active and engage effector proteins including C-RAF and phosphoinositide 3-kinase (PI3K) to promote the RAF/mitogen or extracellular signal-regulated kinases (MEK/ERK) pathway, PI3K/AKT/mammalian target of rapamycin (mTOR) pathway and RaIGDS (Ral guanine nucleotide dissociation stimulator) pathway (McCormick et al., J. Mol. Med. (Berl)., 2016, 94(3):253-8; Rodriguez-Viciana et al., Cancer Cell. 2005, 7(3):205-6). These pathways affect diverse cellular processes such as proliferation, survival, metabolism, motility, angiogenesis, immunity and growth (Young et al., Adv. Cancer Res., 2009, 102:1-17; Rodriguez-Viciana et al., Cancer Cell. 2005, 7(3):205-6).

Cancer-associated mutations in RAS-family proteins suppress their intrinsic and GAP-induced GTPase activity leading to an increased population of GTP-bound/active RAS-family proteins (McCormick et al., Expert Opin. Ther. Targets., 2015, 19(4):451-4; Hunter et al., Mol. Cancer Res., 2015, 13(9): 1325-35). This in turn leads to persistent activation of effector pathways (e.g. MEK/ERK, PI3K/AKT/mTOR, RaIGDS pathways) downstream of RAS-family proteins. KRAS mutations (e.g. amino acids G12, G13, Q61, A146) are found in a variety of human cancers including lung cancer, colorectal cancer and pancreatic cancer (Cox et al., Nat. Rev. Drug Discov., 2014, 13(11):828-51). Mutations in HRAS (e.g. amino acids G12, G13, Q61) and NRAS (e.g. amino acids G12, G13, Q61, A146) are also found in a variety of human cancer types, however, typically at a lower frequency compared to KRAS mutations (Cox et al., Nat. Rev. Drug Discov., 2014, 13(11):828-51). Alterations (e.g. mutation, over-expression, gene amplification) in RAS-family proteins have also been described as a resistance mechanism against cancer drugs such as the EGFR antibodies cetuximab and panitumumab (Leto et al., J. Mol. Med. (Berl). 2014 July; 92(7):709-22) and the EGFR tyrosine kinase inhibitor osimertinib/AZD9291 (Ortiz-Cuaran et al., Clin. Cancer Res., 2016, 22(19):4837-47; Eberlein et al., Cancer Res., 2015, 75(12):2489-500).

Son of Sevenless 1 (SOS1) is a human homologue of the originally identified *Drosophila* protein Son of Sevenless (Pierre et al., Biochem. Pharmacol., 2011, 82(9): 1049-56; Chardin et al., Cytogenet. Cell. Genet., 1994, 66(1):68-9). The SOS1 protein consists of 1333 amino acids (150 kDa). SOS1 is a multi-domain protein with two tandem N-terminal histone domains (HD) followed by the db1 homology domain (DH), a Pleckstrin homology domain (PH), a helical linker (HL), RAS exchanger motif (REM), CDC25 homology domain and a C-terminal proline rich domain (PR). SOS1 has two binding sites for RAS-family proteins; a catalytic site that binds GDP-bound RAS-family proteins to promote guanine nucleotide exchange and an allosteric site that binds GTP-bound RAS-family proteins which causes a further increase in the catalytic GEF function of SOS1 (Freedman et al., Proc. Natl. Acad. Sci. USA., 2006, 103 (45): 16692-7; Pierre et al., Biochem. Pharmacol., 2011, 82(9): 1049-56). Published data indicate a critical involvement of SOS1 in mutant KRAS activation and oncogenic signaling in cancer (Jeng et al., Nat. Commun., 2012, 3:1 168). Depleting SOS1 levels decreased the proliferation rate and survival of tumor cells carrying a KRAS mutation whereas no effect was observed in KRAS wild type cell lines. The effect of loss of SOS1 could not be rescued by introduction of a catalytic site mutated SOS1, demonstrating the essential role of SOS1 GEF activity in KRAS mutant cancer cells.

SOS1 is critically involved in the activation of RAS-family protein signaling in cancer via mechanisms other than mutations in RAS-family proteins. SOS1 interacts with the adaptor protein Grb2 and the resulting SOS1/Grb2 complex binds to activated/phosphorylated Receptor Tyrosine Kinases (e.g. EGFR, ErbB2, ErbB3, ErbB4, PDGFR-A/B, FGFR1/2/3, IGF1 R, INSR, ALK, ROS, TrkA, TrkB, TrkC, RET, c-MET, VEGFR1/2/3, AXL) (Pierre et al., Biochem. Pharmacol., 2011, 82(9): 1049-56). SOS1 is also recruited to other phosphorylated cell surface receptors such as the T cell Receptor (TCR), B cell Receptor (BCR) and monocyte colony-stimulating factor receptor (Salojin et al., J. Biol. Chem. 2000, 275(8):5966-75). This localization of SOS1 to the plasma membrane, proximal to RAS-family proteins, enables SOS1 to promote RAS-family protein activation. SOS1-activation of RAS-family proteins can also be mediated by the interaction of SOS1/Grb2 with the BCR-ABL oncoprotein commonly found in chronic myelogenous leukemia (Kardinal et al., 2001, Blood, 98:1773-81; Sini et al., Nat. Cell Biol., 2004, 6(3):268-74). Furthermore, alterations in SOS1 have been implicated in cancer. SOS1 mutations are found in embryonal rhabdomyosarcomas, sertoli cell testis tumors, granular cell tumors of the skin (Denayer et al., Genes Chromosomes Cancer, 2010, 49(3):242-52) and lung adenocarcinoma (Cancer Genome Atlas Research Network, Nature. 2014, 511 (7511):543-50). Meanwhile over-expression of SOS1 has been described in bladder cancer (Watanabe et al., IUBMB Life, 2000, 49(4): 317-20) and prostate cancer (Timofeeva et al., Int. J. Oncol., 2009, 35(4):751-60). In addition to cancer, hereditary SOS1 mutations are implicated in the pathogenesis of RASopathies like e.g. Noonan syndrome (NS), cardio-facio-cutaneous syndrome (CFC) and hereditary gingival fibromatosis type 1 (Pierre et al., Biochem. Pharmacol., 2011, 82(9): 1049-56).

SOS1 is also a GEF for the activation of the GTPases RAC1 (Ras-related C3 botulinum toxin substrate 1) (Innocenti et al., J. Cell Biol., 2002, 156(1): 125-36). RAC1, like RAS-family proteins, is implicated in the pathogenesis of a variety of human cancers and other diseases (Bid et al., Mol. Cancer Ther. 2013, 12(10):1925-34).

Son of Sevenless 2 (SOS2), a homolog of SOS1 in mammalian cells, also acts as a GEF for the activation of RAS-family proteins (Pierre et al., Biochem. Pharmacol., 2011, 82(9): 1049-56; Buday et al., Biochim. Biophys. Acta., 2008, 1786(2):178-87). Published data from mouse knockout models suggests a redundant role for SOS1 and SOS2 in homeostasis in the adult mouse. Whilst germline knockout of SOS1 in mice results in lethality during mid-embryonic gestation (Qian et al., EMBO J., 2000, 19(4): 642-54), systemic conditional SOS1 knockout adult mice are viable (Baltanas et al., Mol. Cell. Biol., 2013, 33(22): 4562-78). SOS2 gene targeting did not result in any overt phenotype in mice (Esteban et al., Mol. Cell. Biol., 2000, 20(17):6410-3). In contrast, double SOS1 and SOS2 knock-out leads to rapid lethality in adult mice (Baltanas et al., Mol. Cell. Biol., 2013, 33(22):4562-78). These published data suggest that selective targeting of individual SOS isoforms (e.g. selective SOS1 targeting) may be adequately tolerated to achieve a therapeutic index between SOS1/RAS-family protein driven cancers (or other SOS1/RAS-family protein pathologies) and normal cells and tissues.

Selective pharmacological inhibition of the binding of the catalytic site of SOS1 to RAS-family proteins is expected to prevent SOS1-mediated activation of RAS-family proteins to the GTP-bound form. Such SOS1 inhibitor compounds are expected to consequently inhibit signaling in cells down-stream of RAS-family proteins (e.g. ERK phosphorylation). In cancer cells associated with dependence on RAS-family proteins (e.g. KRAS mutant cancer cell lines), SOS1 inhibitor compounds are expected to deliver anti-cancer efficacy (e.g. inhibition of proliferation, survival, metastasis etc.). High potency towards inhibition of SOS1:RAS-family protein binding (nanomolar level $IC_{50}$ values) and ERK phosphorylation in cells (nanomolar level $IC_{50}$ values) are desirable characteristics for a SOS1 inhibitor compound. Furthermore, a desirable characteristic of SOS1 inhibitor compound would be the selective inhibition of SOS1 over SOS2. This conclusion is based on the viable phenotype of SOS1 knockout mice and lethality of SOS1/SOS2 double knockout mice, as described above.

These characteristics have not been fully achieved in previously described SOS1 inhibitor compounds. In the last decades the RAS family proteins-SOS1 protein interaction has gained increasing recognition. Until today several efforts to identify and optimize binders, which target either the effector binding site of RAS or the catalytic binding site of SOS1 (for a selected review see: Lu et al., Chem Med Chem. 2016, 11 (8):814-21), have been made with limited success.

Recently, small activating molecules have been identified, which bind to a lipophilic pocket of SOS1 in close proximity to the RAS binding site (Burns et al., Proc. Natl. Acad. Sci. 2014, 111 (9):3401-6). However, binding of these molecules seems to lead to increased nucleotide exchange and thereby activation of RAS instead of deactivation.

In an effort to stabilize the protein-protein-interaction of RAS-family proteins with SOS1 and to prevent reloading of RAS-family proteins with GTP, several different fragments were subsequently identified (Winter et al., J. Med. Chem. 2015, 58(5):2265-74). However, reversible binding of fragments to SOS1 did not translate into a measurable effect on the nucleotide exchange and only a weak effect was observed for fragments covalently bound to RAS.

Also recently, studies have been conducted to combine rational design and screening platforms to identify small molecule inhibitors of SOS1 (Evelyn et al., Chem. Biol. 2014, 21 (12):1618-28; Evelyn et al., J. Biol. Chem. 2015, 290(20):12879-98; Zheng et al., WO 2016/077793), i.e. compounds which bind to SOS1 and inhibit protein-protein interaction with RAS-family proteins. Although compounds with a slight inhibitory effect on SOS1 have been identified, the effects on guanine nucleotide exchange and cellular signal transduction modulation (e.g. ERK phosphorylation) are weak. WO2018/115380 and WO2018/172250 disclose quinazoline-based SOS inhibitors.

Accordingly, there are needs to for new compounds that modulate SOS1 activity for the treatment of diseases and disorders, e.g. oncological diseases.

SUMMARY

The present disclosure provides SOS1 inhibitors, for example, compounds of structural formula (I), (II), (III-A), or (III-B), pharmaceutically acceptable salts, stereoisomers, and pharmaceutical compositions thereof. It was unexpected to find that the compounds disclosed herein significantly improve human liver microsomal stability and effectively inhibit the SOS1 activity.

(I)

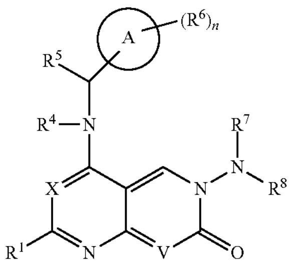

The present disclosure further provides methods of using the compounds disclosed herein (e.g., compounds of structural formula (I), (II), (III-A), or (III-B)), pharmaceutically acceptable salts, stereoisomers, or pharmaceutical compositions thereof, to inhibit the activity of SOS1.

The present disclosure further provides methods for using the compounds disclosed herein (e.g., compounds of structural formula (I), (II), (III-A), or (III-B)), pharmaceutically acceptable salts, stereoisomers, or pharmaceutical compositions thereof, to treat a condition, disease or disorder in which the inhibition of the interaction of SOS1 and a RAS-family protein or RAC1 is of therapeutic benefit, specifically in treating oncological diseases.

In one aspect, the present disclosure provides a compound of any one of the formulae described herein (e.g., structural formula (I), (II), (III-A), or (III-B)), a pharmaceutically acceptable salt, or a stereoisomer thereof.

In one aspect, the present disclosure provides a pharmaceutical composition comprising a compound of any one of the formulae described herein (e.g., structural formula (I), (II), (III-A), or (III-B)), a pharmaceutically acceptable salt, or a stereoisomer thereof, as defined in any one of the embodiments described herein, in a mixture with at least one pharmaceutically acceptable carrier.

In another aspect, the present disclosure provides a compound of any one of the formulae described herein (e.g., structural formula (I), (II), (III-A), or (III-B)), a pharmaceutically acceptable salt, or a stereoisomer thereof, as defined in any one of the embodiments described herein, for use as a medicament.

In another aspect, the present disclosure provides a compound of any one of the formulae described herein (e.g., structural formula (I), (II), (III-A), or (III-B)), a pharmaceutically acceptable salt, or a stereoisomer thereof, as defined in any one of the embodiments described herein, for use in the treatment of a condition, disease or disorder in which the inhibition of the interaction of SOS1 and a RAS-family protein or RAC1 is of therapeutic benefit, specifically in treating oncological diseases.

In another aspect, the present disclosure provides a use of a compound of any one of the formulae described herein (e.g., structural formula (I), (II), (III-A), or (III-B)), a pharmaceutically acceptable salt, or a stereoisomer thereof, as defined in any one of the embodiments described herein, for the manufacture of a medicament for treating a condition, disease or disorder in which the inhibition of the interaction of SOS1 and a RAS-family protein or RAC1 is of therapeutic benefit, specifically in treating oncological diseases.

DETAILED DESCRIPTION

1. Compounds

In a first embodiment, the present disclosure provides a compound represented by Formula (I):

(I)

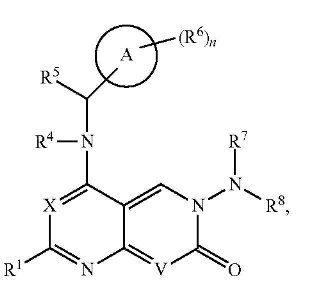

a pharmaceutically acceptable salt, or a stereoisomer thereof, wherein:

- ring A is 3-12 membered carbocyclyl, 3-12 membered heterocyclyl, 6-10 membered aryl, or 5-10 membered heteroaryl;
- $R^1$ is hydrogen, halogen, $C_{1-6}$alkyl, or $C_{3-6}$cycloalkyl, wherein said $C_{1-6}$alkyl or $C_{3-6}$cycloalkyl represented by $R^1$ is optionally substituted by one to more groups selected from halogen and —OH;
- V is N or $CR^2$; wherein
- $R^2$ is hydrogen, halogen, —CN, $C_{1-6}$alkyl, $C_{2-6}$alkenyl, $C_{2-6}$alkynyl, —$OR^{2a}$, —$NR^{2a}R^{2b}$, —$C(O)R^{2a}$, —$C(O)OR^{2a}$, —$C(O)NR^{2a}R^{2b}$, —$SO_2R^{2a}$, —$SO_2NR^{2a}R^{2b}$, —$P(O)R^{2a}R^{2b}$, —$NR^{2a}C(O)R^{2b}$, —$NR^{2a}C(O)OR^{2b}$, —$NR^{2a}SO_2R^{2b}$, —$NR^{2a}SO_2NR^{2b}R^{2c}$, 3-12 membered carbocyclyl, 3-12 membered heterocyclyl, 6-10 membered aryl, or 5-10 membered heteroaryl; wherein said $C_{1-6}$alkyl, $C_{2-6}$alkenyl, $C_{2-6}$alkynyl, 3-12 membered carbocyclyl, 3-12 membered heterocyclyl, 6-10 membered aryl, or 5-10 membered heteroaryl represented by $R^2$ is optionally substituted by one or more $R^{2d}$; wherein
  - $R^{2a}$, $R^{2b}$, and $R^{2c}$ are independently selected from the group consisting of hydrogen, $C_{1-6}$alkyl, 3-12 membered carbocyclyl, 3-12 membered heterocyclyl, 6-10 membered aryl, and 5-10 membered heteroaryl; or $R^{2a}$ and $R^{2b}$ or $R^{2b}$ and $R^{2c}$ together with the N or P atom to which they are attached form 4-12 membered heterocyclyl or 5-10 membered heteroaryl; wherein said $C_{1-6}$alkyl, carbocyclyl, heterocyclyl, aryl, or heteroaryl represented by $R^{2a}$, $R^{2b}$, or $R^{2c}$ or in the group represented by $R^{2a}$, $R^{2b}$, or $R^{2c}$ are optionally substituted with one or more $R^{2d}$; wherein
  - $R^{2d}$, in each occurrence, is hydrogen, halogen, oxo, —CN, $C_{1-6}$alkyl, $C_{1-6}$haloalkyl, —$OR^{2e}$, —$NR^{2e}R^{2f}$, —$C(O)R^{2e}$, —$C(O)OR^{2e}$, —$C(O)NR^{2e}R^{2f}$, —$SO_2R^{2e}$, —$SO_2NR^{2e}R^{2f}$, —$P(O)R^{2e}R^{2f}$, —$NR^{2e}C(O)R^{2f}$, —$NR^{2e}C(O)OR^{2f}$, —$NR^{2e}SO_2R^{2f}$, —$NR^{2e}SO_2NR^{2f}R^{2g}$, 3-12 membered carbocyclyl, 3-12 membered heterocyclyl, 6-10 membered aryl, or 5-10 membered heteroaryl;
  - $R^{2e}$, $R^{2f}$, and $R^{2g}$ are independently selected from the group consisting of hydrogen and $C_{1-6}$alkyl;
- X is N or $CR^3$;
- $R^3$ is hydrogen, halogen, or $C_{1-3}$alkyl;
- $R^4$ is hydrogen or $C_{1-6}$alkyl;
- $R^5$ is hydrogen, $C_{1-6}$alkyl, 3-6 membered monocyclic carbocyclyl, or 4-6 membered monocyclic heterocyclyl; wherein said $C_{1-6}$alkyl, 3-6 membered monocyclic carbocyclyl, or 4-6 membered monocyclic heterocyclyl represented by $R^5$ is optionally substituted with one or more groups selected from halogen and —OH;
- $R^6$ is hydrogen, —OH, halogen, —CN, oxo, $C_{1-6}$alkyl, $C_{1-6}$alkoxy, —$SO_2R^{6a}$, —$SO_2NR^{6a}R^{6b}$, —$P(O)R^{6a}R^{6b}$, —$C(O)NR^{6a}R^{6b}$, —$NR^{6a}C(O)R^{6a}$, —$NR^{6a}C(O)NR^{6a}R^{6b}$, —$(CH_2)_sNR^{6a}R^{6b}$, —$O(CH_2)_tNR^{6a}R^{6b}$, 3-12 membered carbocyclyl, 3-12 membered heterocyclyl, 6-10 membered aryl, 5-10 membered heteroaryl; wherein said $C_{1-6}$alkyl, $C_{1-6}$alkoxy, 3-12 membered carbocyclyl, 3-12 membered heterocyclyl, 6-10 membered aryl, or 5-10 membered heteroaryl represented by $R^6$ is optionally substituted by one to more $R^{6c}$; wherein
  - $R^{6a}$ and $R^{6b}$ are independently hydrogen or $C_{1-6}$alkyl, or $R^{6a}$ and $R^{6b}$ together with the N or P atom to which they are attached form 4-7 membered heterocyclyl;
  - s is an integral from 0 to 3;
  - t is an integral from 2 to 4;
  - $R^{6c}$, in each occurrence, is hydrogen, —OH, halogen, —CN, oxo, $C_{1-6}$alkyl, $C_{1-6}$alkoxy, $C_{3-6}$cycloalkyl, —$NR^{6a}R^{6b}$, —$SO_2R^{6a}$, —$SO_2NR^{6a}R^{6b}$, —$C(O)NR^{6a}R^{6b}$, —$P(O)R^{6a}R^{6b}$, —$NR^{6a}C(O)R^{6a}$, —$NR^{6a}C(O)NR^{6a}R^{6b}$, —$(CH_2)_sNR^{6a}R^{6b}$, or —$O(CH_2)_tNR^{6a}R^{6b}$; wherein said $C_{1-6}$alkyl or $C_{3-6}$cycloalkyl represented by $R^{6c}$ is optionally substituted with one to more groups selected from halogen, —OH and —$NR^{6a}R^{6b}$;
- $R^7$ and $R^8$ are independently hydrogen, $C_{1-6}$alkyl, $C_{3-6}$alkenyl, $C_{3-6}$alkynyl, $C_{2-6}$alkoxy, 3-12 membered carbocyclyl, 3-12 membered heterocyclyl, 6-10 membered aryl, or 5-10 membered heteroaryl; wherein said $C_{1-6}$alkyl, $C_{3-6}$alkenyl, $C_{3-6}$alkynyl, $C_{2-6}$alkoxy, 3-12 membered carbocyclyl, 3-12 membered heterocyclyl, 6-10 membered aryl, or 5-10 membered heteroaryl represented by $R^7$ or $R^8$ is optionally substituted by one or more $R^{7a}$; or
- $R^7$ and $R^8$ together with the N atom to which they are attached form 4-12 membered heterocyclyl or 5-10 membered heteroaryl; wherein said 4-12 membered heterocyclyl or 5-10 membered heteroaryl is optionally substituted with one or more $R^{7b}$;
  - $R^{7a}$ is hydrogen, halogen, —CN, $C_{1-6}$alkyl, —$OR^{7c}$, —$NR^{7c}R^{7d}$, —$C(O)R^{7c}$, —$C(O)OR^{7c}$, —C(O)

$NR^{7c}R^{7d}$, $—SO_2R^{7c}$, $—P(O)R^{7c}R^{7d}$, $—SO_2NR^{7c}R^{7d}$, $—NR^{7c}C(O)R^{7d}$, $—NR^{7c}C(O)OR^{7d}$, $—NR^{7c}SO_2R^{7d}$, $—NR^{7c}SO_2NR^{7d}R^{7e}$, 3-12 membered carbocyclyl, 3-12 membered heterocyclyl, 6-10 membered aryl, or 5-10 membered heteroaryl, wherein said $C_{1-6}$alkyl, 3-12 membered carbocyclyl, 3-12 membered heterocyclyl, 6-10 membered aryl, or 5-10 membered heteroaryl represented by $R^{7a}$ is optionally substituted by one or more $R^{7f}$;

$R^{7b}$ is hydrogen, halogen, —CN, oxo, $C_{1-6}$alkyl, $C_{2-6}$alkenyl, $C_{2-6}$alkynyl, $C_{1-6}$alkoxy, $—OR^{7c}$, $—NR^{7c}R^{7d}$, $—C(O)R^{7c}$, $—C(O)OR^{7c}$, $—C(O)NR^{7c}R^{7d}$, $—SO_2R^{7c}$, $—P(O)R^{7c}R^{7d}$, $—SO_2NR^{7c}R^{7d}$, $—NR^{7c}C(O)R^{7d}$, $—NR^{7c}C(O)OR^{7d}$, $—NR^{7c}SO_2R^{7d}$, $—NR^{7c}SO_2NR^{7d}R^{7e}$, 3-12 membered carbocyclyl, 3-12 membered heterocyclyl, 6-10 membered aryl, or 5-10 membered heteroaryl, wherein $C_{1-6}$alkyl, $C_{2-6}$alkenyl, $C_{2-6}$alkynyl, $C_{1-6}$alkoxy, 3-12 membered carbocyclyl, 3-12 membered heterocyclyl, or 5-10 membered heteroaryl represented by $R^{7b}$ is optionally substituted by one or more $R^{7f}$;

$R^{7c}$, $R^{7d}$, and $R^{7e}$ are independently selected from the group consisting of hydrogen, $C_{1-6}$alkyl, 3-12 membered carbocyclyl, 4-12 membered heterocyclyl, 6-10 membered aryl, and 5-10 membered heteroaryl; or $R^{7c}$ and $R^{7d}$ together with the N or P atom to which they are attached form 4-12 membered heterocyclyl or 5-10 membered heteroaryl; wherein said $C_{1-6}$alkyl, carbocyclyl, heterocyclyl, aryl, or heteroaryl represented by $R^{7c}$, $R^{7d}$, or $R^{7e}$ or in the group represented by $R^{7c}$, $R^{7d}$, or $R^{7e}$ is optionally substituted with one or more $R^{7f}$;

$R^{7f}$, in each occurrence, is hydrogen, halogen, —CN, or OH; and n is 0, 1, 2, or 3;

wherein said heterocyclyl comprises 1-4 heteroatoms selected from O, N, and S; and said heteroaryl comprises 1-4 heteroatoms selected from O, N, and S.

In a second embodiment, the present disclosure provides a compound according to the first embodiment, wherein the compound is represented by Formula II:

(II)

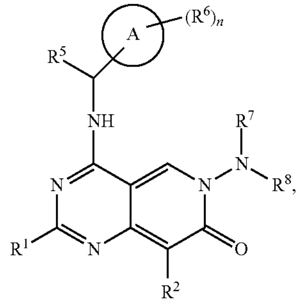

a pharmaceutically acceptable salt, or a stereoisomer thereof, and the definitions of the variables are provided in the first embodiment.

In a third embodiment, the present disclosure provides a compound according to the first or second embodiment, a pharmaceutically acceptable salt or a stereoisomer thereof, wherein ring A is 3-10 membered carbocyclyl, 4-10 membered heterocyclyl, 6-10 membered aryl, or 5-10 membered heteroaryl;

$R^1$ is hydrogen, $C_{1-4}$alkyl, or $C_{3-6}$cycloalkyl;

$R^2$ is hydrogen, halogen, —CN, $C_{1-4}$alkyl, $C_{2-4}$alkenyl, $C_{2-4}$alkynyl, $—OR^{2a}$, $—NR^{2a}R^{2b}$, $—C(O)R^{2a}$, $—C(O)OR^{2a}$, $—C(O)NR^{2a}R^{2b}$, $—NR^{2a}C(O)R^{2b}$, $—NR^{2a}C(O)OR^{2b}$, 3-6 membered monocyclic carbocyclyl, 3-6 membered monocyclic heterocyclyl, 6-10 membered aryl, or 5-10 membered heteroaryl; wherein said $C_{1-4}$alkyl, $C_{2-4}$alkenyl, $C_{2-4}$alkynyl, 3-6 membered monocyclic carbocyclyl, 3-6 membered monocyclic heterocyclyl, 6-10 membered aryl, or 5-10 membered heteroaryl represented by $R^2$ is optionally substituted by one to three $R^{2d}$; wherein $R^{2a}$ and $R^{2b}$ are independently selected from the group consisting of hydrogen, $C_{1-6}$alkyl, $C_{1-6}$haloalkyl, or $C_{1-6}$hydroxyalkyl; or $R^{2a}$ and $R^{2b}$ together with the N atom to which they are attached form 4-12 membered heterocyclyl or 5-10 membered heteroaryl;

$R^{2d}$, in each occurrence, is hydrogen, halogen, oxo, —CN, $C_{1-6}$alkyl, $C_{1-6}$haloalkyl, $C_{1-6}$hydroxyalkyl, $—OR^{2e}$, $—NR^{2e}R^{2f}$, $—SO_2R^{2e}$, $—P(O)R^{2e}R^{2f}$, $COOR^{2e}$, $CONR^{2e}R^{2f}$, 3-6 membered monocyclic carbocyclyl, 3-6 membered monocyclic heterocyclyl, 6-10 membered aryl, or 5-10 membered heteroaryl;

$R^{2e}$ and $R^{2f}$ are independently selected from the group consisting of hydrogen and $C_{1-6}$alkyl;

$R^5$ is hydrogen, $C_{1-4}$alkyl, 3-5 membered monocyclic carbocyclyl, or 4-5 membered monocyclic heterocyclyl;

$R^6$ is hydrogen, —OH, halogen, —CN, oxo, $C_{1-6}$alkyl, $—(CH_2)_sNR^{6a}R^{6b}$, 3-6 membered monocyclic carbocyclyl, 3-6 membered monocyclic heterocyclyl, 6-10 membered aryl, 5-10 membered heteroaryl; wherein said $C_{1-6}$alkyl, 3-6 membered monocyclic carbocyclyl, 3-6 membered monocyclic heterocyclyl, 6-10 membered aryl, or 5-10 membered heteroaryl represented by $R^6$ is optionally substituted by one to more $R^{6c}$; wherein $R^{6a}$ and $R^{6b}$ are independently hydrogen or $C_{1-4}$alkyl;

s is an integral from 0 to 2;

$R^{6c}$, in each occurrence, is hydrogen, —OH, halogen, —CN, oxo, $C_{1-6}$alkyl, $—NR^{6a}R^{6b}$, or $—(CH_2)_sNR^{6a}R^{6b}$; wherein said $C_{1-6}$alkyl represented by $R^{6c}$ is optionally substituted with one to more groups selected from halogen and —OH;

$R^7$ and $R^8$ are independently hydrogen, $C_{1-4}$alkyl, $C_{3-4}$alkenyl, $C_{3-4}$alkynyl, $C_{2-4}$alkoxy, 3-6 membered monocyclic carbocyclyl, 3-6 membered monocyclic heterocyclyl, 6-10 membered aryl, or 5-10 membered heteroaryl; wherein said $C_{1-4}$alkyl, $C_{3-4}$alkenyl, $C_{3-4}$alkynyl, $C_{2-4}$alkoxy, 3-6 membered monocyclic carbocyclyl, 3-6 membered monocyclic heterocyclyl, 6-10 membered aryl, or 5-10 membered heteroaryl represented by $R^7$ or $R^8$ is optionally substituted by one or more $R^{7a}$; or $R^7$ and $R^8$ together with the N atom to which they are attached form 4-12 membered heterocyclyl or 5-10 membered heteroaryl; wherein said 4-12 membered heterocyclyl or 5-10 membered heteroaryl is optionally substituted with one to three $R^{7b}$;

$R^{7a}$ is hydrogen, halogen, —CN, $C_{1-6}$alkyl, $—OR^{7c}$, or $—NR^{7c}R^{7d}$;

$R^{7b}$ is hydrogen, halogen, —CN, oxo, $C_{1-6}$alkyl, $C_{1-6}$alkoxy, $—OR^{7c}$, $—NR^{7c}R^{7d}$, $—C(O)R^{7c}$, —C(O)OR$^{7c}$, —SO$_2$R$^{7c}$, or 5-10 membered heteroaryl, wherein C$_{1-6}$alkyl, C$_{1-6}$alkoxy, or 5-10 membered heteroaryl represented by R$^{7b}$ is optionally substituted by one or more R$^{7f}$;

R$^{7c}$ or R$^{7d}$ are independently selected from the group consisting of hydrogen, C$_{1-4}$alkyl, 3-6 membered monocyclic carbocyclyl, 4-8 membered heterocyclyl, 6-10 membered aryl, and 5-10 membered heteroaryl; or R$^{7c}$ and R$^{7d}$ together with the N atom to which they are attached form 4-8 membered heterocyclyl or 5-10 membered heteroaryl; wherein said C$_{1-4}$alkyl, 3-6 membered monocyclic carbocyclyl, 4-8 membered heterocyclyl, 6-10 membered aryl, or 5-10 membered heteroaryl represented by R$^{7c}$ or R$^{7d}$ is optionally substituted with one to three R$^{7f}$; and R$^{7f}$, in each occurrence, is hydrogen, halogen, —CN, or —OH.

In a fourth embodiment, the present disclosure provides a compound according to any one of the first through third embodiments, a pharmaceutically acceptable salt or a stereoisomer thereof, wherein R$^2$ is hydrogen, halogen, —CN, C$_{1-4}$alkyl, C$_{2-4}$alkenyl, C$_{2-4}$alkynyl, 3-6 membered monocyclic carbocyclyl, 3-6 membered monocyclic heterocyclyl, 6-10 membered aryl, or 5-10 membered heteroaryl; wherein said C$_{1-4}$alkyl, C$_{2-4}$alkenyl, C$_{2-4}$alkynyl, 3-6 membered monocyclic carbocyclyl, 3-6 membered monocyclic heterocyclyl, 6-10 membered aryl, or 5-10 membered heteroaryl represented by R$^2$ is optionally substituted by one to three R$^{2d}$; wherein R$^{2d}$, in each occurrence, is hydrogen, halogen, oxo, —CN, C$_{1-6}$alkyl, C$_{1-6}$haloalkyl, C$_{1-6}$hydroxyalkyl, —OR$^{2e}$, —NR$^{2e}$R$^{2f}$, —SO$_2$R$^{2e}$, —P(O)R$^{2e}$R$^{2f}$, COOR$^{2e}$, CONR$^{2e}$R$^{2f}$, 3-6 membered monocyclic carbocyclyl, 3-6 membered monocyclic heterocyclyl, 6-10 membered aryl, or 5-10 membered heteroaryl; and R$^{2e}$ and R$^{2f}$ are independently selected from the group consisting of hydrogen and C$_{1-6}$alkyl.

In a fifth embodiment, the present disclosure provides a compound according to any one of the first through fourth embodiments, a pharmaceutically acceptable salt or a stereoisomer thereof, wherein R$^7$ and R$^8$ are independently hydrogen, C$_{1-4}$alkyl, C$_{3-4}$alkenyl, C$_{3-4}$alkynyl; wherein said C$_{1-4}$alkyl, C$_{3-4}$alkenyl, C$_{3-4}$alkynyl represented by R$^7$ or R$^8$ is optionally substituted by one or more R$^{7a}$; or R$^7$ and R$^8$ together with the N atom to which they are attached form 4-12 membered heterocyclyl or 5 membered heteroaryl, each of which is optionally substituted with one to three R$^{7b}$;

R$^{7a}$ is hydrogen, halogen, —CN, C$_{1-6}$alkyl, —OR$^{7c}$, or —NR$^{7c}$R$^{7d}$;

R$^{7b}$ is hydrogen, halogen, —CN, oxo, —OH, C$_{1-6}$alkyl, C$_{1-6}$alkoxy, —NR$^{7c}$R$^{7d}$, —C(O)R$^{7c}$, —C(O)OR$^{7c}$, —SO$_2$R$^{7c}$, or 5-10 membered heteroaryl, wherein C$_{1-6}$alkyl, C$_{1-6}$alkoxy, or 5-10 membered heteroaryl represented by R$^{7b}$ is optionally substituted by one or more R$^{7f}$;

R$^7$, or R$^{7d}$ are independently selected from the group consisting of hydrogen, C$_{1-4}$alkyl, 3-6 membered monocyclic carbocyclyl, 4-8 membered heterocyclyl, 6-10 membered aryl, and 5-10 membered heteroaryl; or R$^{7c}$ and R$^{7d}$ together with the N atom to which they are attached form 4-8 membered heterocyclyl or 5-10 membered heteroaryl; wherein said C$_{1-4}$alkyl, 3-6 membered carbocyclyl, 4-8 membered heterocyclyl, 6-10 membered aryl, or 5-10 membered heteroaryl represented by R$^{7c}$ or R$^{7d}$ is optionally substituted with one to three R$^{7f}$; and R$^{7f}$, in each occurrence, is hydrogen, halogen, —CN, or —OH.

In a sixth embodiment, the present disclosure provides a compound according to the first, second, third, fourth, or fifth embodiment, a pharmaceutically acceptable salt or a stereoisomer thereof, wherein ring A is 3-6 membered monocyclic cycloalkyl, 4-6 membered monocyclic heterocyclyl, phenyl, or 5-10 membered heteroaryl;

R$^6$ is hydrogen, —OH, halogen, —CN, C$_{1-6}$alkyl, or —(CH$_2$)$_s$NR$^{6a}$R$^{6b}$; wherein said C$_{1-6}$alkyl represented by R$^6$ is optionally substituted with one to more groups selected from halogen and —OH;

R$^{6a}$ and R$^{6b}$ are independently hydrogen or C$_{1-4}$alkyl; and s is 0 or 1.

In a seventh embodiment, the present disclosure provides a compound according to the first, second, third, fourth, fifth, or sixth embodiment, a pharmaceutically acceptable salt or a stereoisomer thereof, wherein ring A is cyclopropyl, phenyl, thiophenyl, or indole.

In an eighth embodiment, the present disclosure provides a compound according to the first, second, third, fourth, fifth, sixth, or seventh embodiment, a pharmaceutically acceptable salt or a stereoisomer thereof, wherein the compound is represented by Formula (III-A) or (III-B):

(III-A)

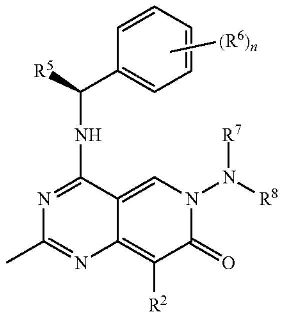

or (III-B)

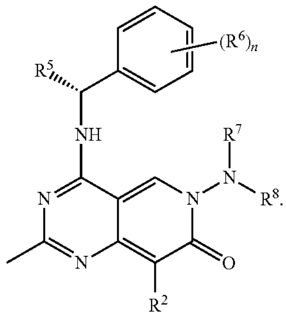

The definitions of the variables are provided in any one of the first through seventh embodiments.

In a ninth embodiment, the present disclosure provides a compound according to the first, second, third, fourth, fifth, sixth, seventh, or eighth embodiment, a pharmaceutically acceptable salt or a stereoisomer thereof, wherein R$^6$ is hydrogen, halogen, C$_{1-4}$alkyl, or —(CH$_2$)NR$^{6a}$R$^{6b}$; wherein said C$_{1-4}$alkyl represented by R$^6$ is optionally substituted with one to more groups selected from halogen and —OH; and R$^{6a}$ and R$^{6b}$ are independently hydrogen or C$_{1-4}$alkyl.

In a tenth embodiment, the present disclosure provides a compound according to the first, second, third, fourth, fifth, sixth, seventh, eighth, or ninth embodiment, a pharmaceutically acceptable salt or a stereoisomer thereof, wherein $R^5$ is hydrogen, methyl, or ethyl, optionally, methyl.

In an eleventh embodiment, the present disclosure provides a compound according to the first, second, third, fourth, fifth, sixth, seventh, eighth, ninth, or tenth embodiment, a pharmaceutically acceptable salt or a stereoisomer thereof, wherein $R^2$ is hydrogen, halogen, —CN, $C_{1-4}$alkyl, $C_{2-4}$alkenyl, 3-6 membered monocyclic cycloalkyl, 5-6 membered monocyclic heterocyclyl, phenyl, or 5-10 membered heteroaryl; wherein said $C_{1-4}$alkyl, 3-6 membered monocyclic cycloalkyl, 5-6 membered monocyclic heterocyclyl, phenyl, or 5-10 membered heteroaryl represented by $R^2$ is optionally substituted by one to three $R^{2d}$;

$R^{2d}$, in each occurrence, is hydrogen, halogen, oxo, —CN, $C_{1-6}$alkyl, $C_{1-6}$haloalkyl, $C_{1-6}$hydroxyalkyl, —$OR^{2e}$, —$NR^{2e}R^{2f}$, —$SO_2R^{2e}$, —$P(O)R^{2e}R^{2f}$, $COOR^{2e}$, $CONR^{2e}R^{2f}$, 3-6 membered monocyclic carbocyclyl, 3-6 membered monocyclic heterocyclyl, phenyl, or 5-10 membered heteroaryl; and $R^{2e}$ and $R^{2f}$ are independently selected from the group consisting of hydrogen and $C_{1-6}$alkyl.

In a twelfth embodiment, the present disclosure provides a compound according to the first, second, third, fourth, fifth, sixth, seventh, eighth, ninth, tenth, or eleventh embodiment, a pharmaceutically acceptable salt, or a stereoisomer thereof, wherein $R^2$ is phenyl or 5-10 membered heteroaryl; wherein said phenyl or 5-10 membered heteroaryl is optionally substituted by one to three $R^{2d}$;

$R^{2d}$, in each occurrence, is hydrogen, halogen, —CN, $C_{1-6}$alkyl, $C_{1-6}$haloalkyl, $C_{1-6}$hydroxyalkyl, —$OR^{2e}$, —$NR^{2e}R^{2f}$, —$SO_2R^{2e}$, —$P(O)R^{2e}R^{2f}$, $COOR^{2e}$, $CONR^{2e}R^{2f}$, 3-6 membered monocyclic carbocyclyl, 3-6 membered monocyclic heterocyclyl, phenyl, or 5-10 membered heteroaryl; and $R^{2e}$ and $R^{2f}$ are independently selected from the group consisting of hydrogen and $C_{1-6}$alkyl.

In a thirteenth embodiment, the present disclosure provides a compound according to the twelfth embodiment, a pharmaceutically acceptable salt or a stereoisomer thereof, wherein $R^2$ is phenyl, pyridyl, pyrimidyl, imidazolyl, pyrazolyl, imidazo[1,2-a]pyrimidine, imidazo[1,2-a]pyridine, or triazolo[4,3-a]pyridine, each of which is optionally substituted by one to three $R^{2d}$; wherein $R^{2d}$ is selected from the group consisting of hydrogen, halogen, —CN, —$CH_3$, —$CF_3$, —$NH_2$, —$S(O)_2Me$, —$OCH_3$, COOH, $CONH_2$, COOMe, —$P(O)(CH_3)_2$, —$CH_2CH_2OH$, and —$CH_2CHF_2$.

In a fourteenth embodiment, the present disclosure provides a compound according to the thirteenth embodiment, a pharmaceutically acceptable salt, or a stereoisomer thereof, wherein $R^2$ is phenyl or pyridyl, each of which is optionally substituted by one to three $R^{2d}$; wherein $R^{2d}$ is selected from the group consisting of hydrogen, halogen, —CN, —$CH_3$, —$CF_3$, —$NH_2$, —$S(O)_2Me$, —$OCH_3$, COOH, $CONH_2$, COOMe, —$P(O)(CH_3)_2$, —$CH_2CH_2OH$, and —$CH_2CHF_2$.

In a fifteenth embodiment, the present disclosure provides a compound according to the first, second, third, fourth, fifth, sixth, seventh, eighth, ninth, tenth, eleventh, twelfth, thirteenth, or fourteenth embodiment, a pharmaceutically acceptable salt, or a stereoisomer thereof, wherein $R^7$ and $R^8$ together with the N atom to which they are attached form 5-10 membered heterocyclyl or 5 membered heteroaryl, each of which is optionally substituted with one to three groups selected from halogen, —CN, oxo, —OH, $C_{1-6}$alkyl, $C_{1-6}$alkoxy, —$C(O)R^{7c}$, —$C(O)OR^{7c}$, and pyridinyl optionally substituted with CN;

$R^7$, is independently selected from the group consisting of hydrogen, $C_{1-4}$alkyl optionally substituted with —CN or —OH.

In a sixteenth embodiment, the present disclosure provides a compound according to the first, second, third, fourth, fifth, sixth, seventh, eighth, ninth, tenth, eleventh, twelfth, thirteenth, or fourteenth embodiment, a pharmaceutically acceptable salt, or a stereoisomer thereof, wherein $R^7$ and $R^8$ are independently hydrogen or $C_{1-4}$alkyl, optionally, $R^7$ and $R^8$ are methyl.

In a seventeenth embodiment, the present disclosure provides a compound according to the first, second, third, fourth, fifth, sixth, seventh, eighth, ninth, tenth, eleventh, fifteenth, or sixteenth embodiment, a pharmaceutically acceptable salt, or a stereoisomer thereof, wherein $R^2$ is selected from the group consisting of H, F, Br, $CH_3$, —CN,
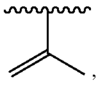
,
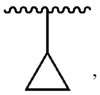
,
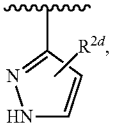
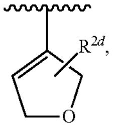
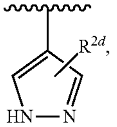
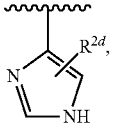
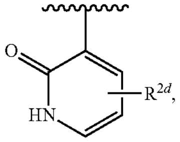
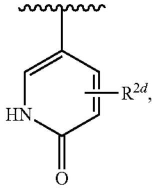
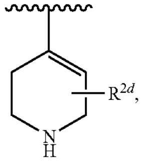
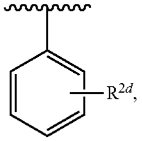
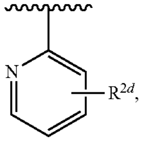
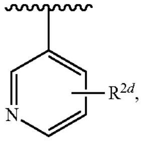
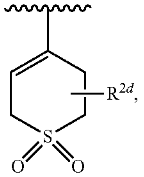
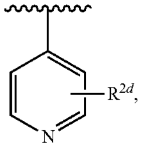
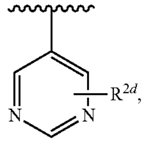
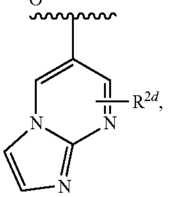
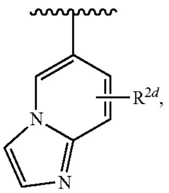
and
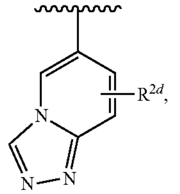

wherein $R^{2d}$ is selected from the group consisting of hydrogen, halogen, —CN, —$CH_3$, —$CF_3$, —$NH_2$, —$S(O)_2Me$, —$OCH_3$, COOH, $CONH_2$, COOMe, —$P(O)(CH_3)_2$, —$CH_2CH_2OH$, and —$CH_2CHF_2$.

In a eighteenth embodiment, the present disclosure provides a compound according to the first, second, third, fourth, fifth, sixth, seventh, eighth, ninth, tenth, eleventh, twelfth, thirteenth, fourteenth, fifteenth, or seventeenth embodiment, a pharmaceutically acceptable salt, or a stereoisomer thereof, wherein $R^7$ and $R^8$ together with the atom to which they are attached form a heterocyclyl selected from the group consisting of

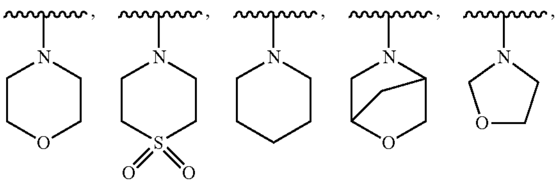

-continued

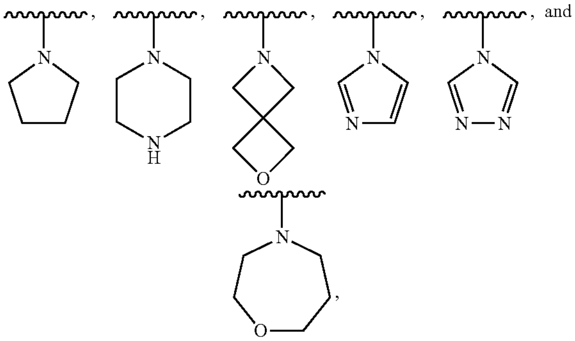

each of which is optionally substituted with one to three groups selected from —F, —CN, oxo, —OH, methyl, isopropyl, methoxyl, —$C(O)R^{7e}$, —$C(O)OR^{7e}$, and pyridinyl optionally substituted with CN.

In one embodiment, the present disclosure provides a compound selected from the compounds disclosed in examples and Table 1, a pharmaceutically acceptable salt or a stereoisomer thereof.

TABLE 1

| ID | Structure |
|---|---|
| Example 1 | 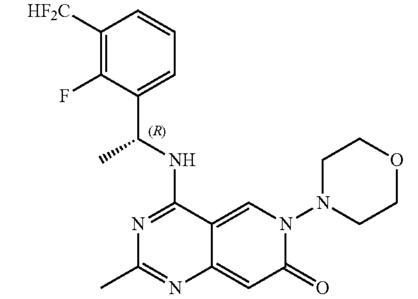 |
| Example 2 | 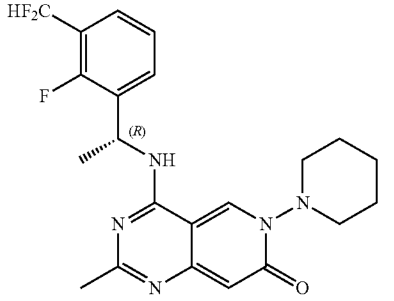 |
| Example 3 | 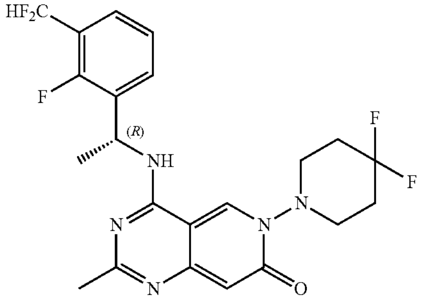 |

TABLE 1-continued
| ID | Structure |
|---|---|
| Example 4 | 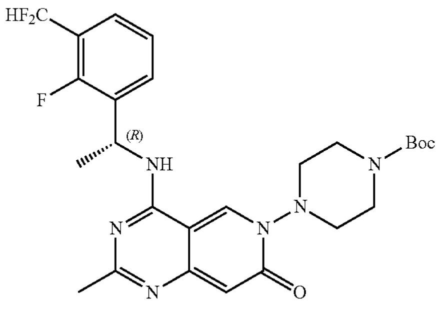 |
| Example 5 | 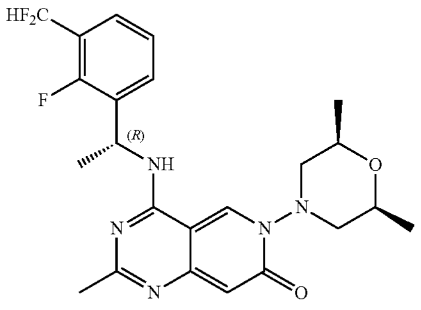 |
| Example 6 | 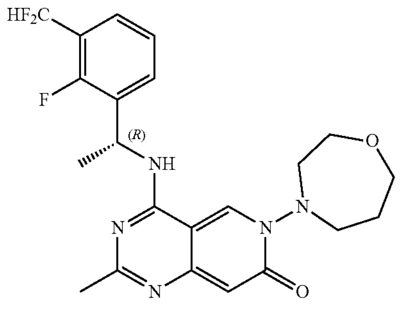 |
| Example 7 | 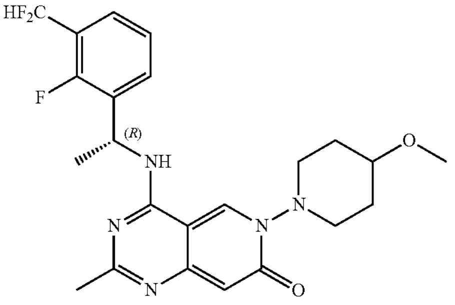 |
| Example 8 | 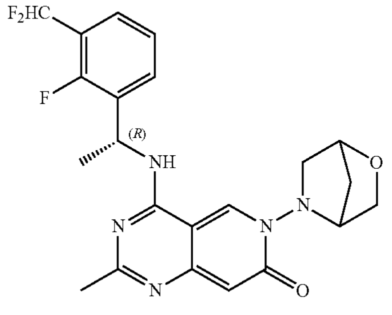 |

TABLE 1-continued
| ID | Structure |
|---|---|
| Example 9 | 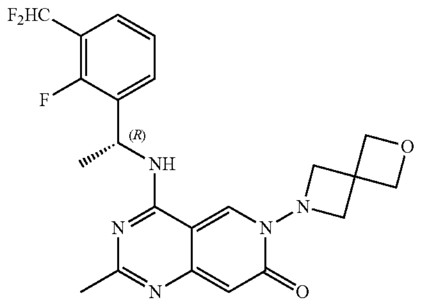 |
| Example 10 | 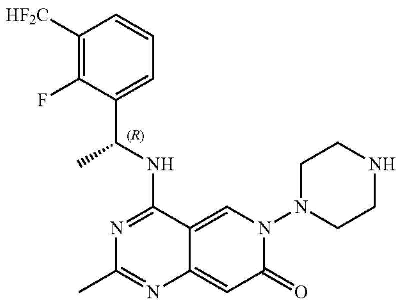 |
| Example 11 | 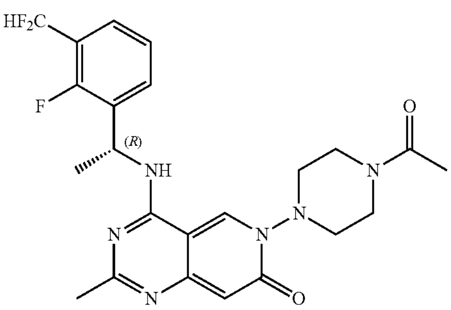 |
| Example 12 | 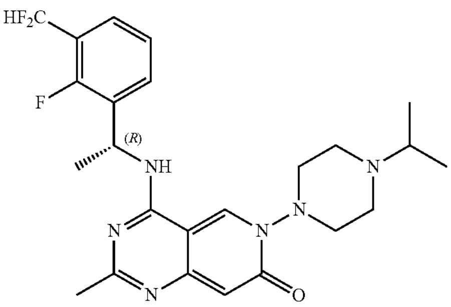 |
| Example 13 | 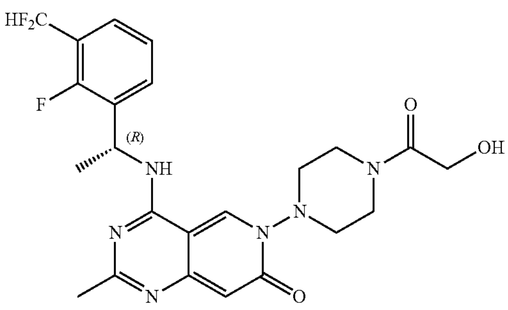 |

TABLE 1-continued
| ID | Structure |
|---|---|
| Example 14 | 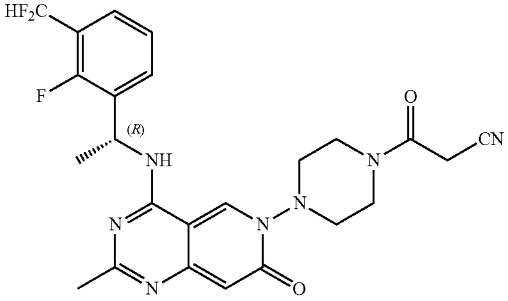 |
| Example 15 | 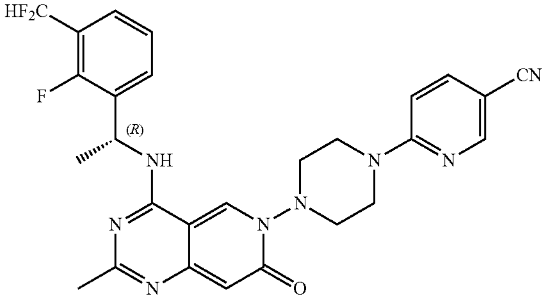 |
| Example 16 | 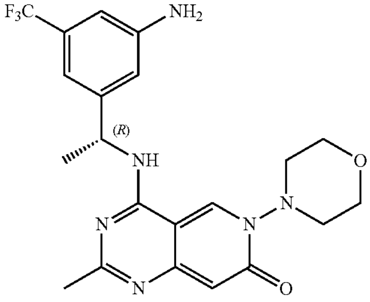 |
| Example 17 | 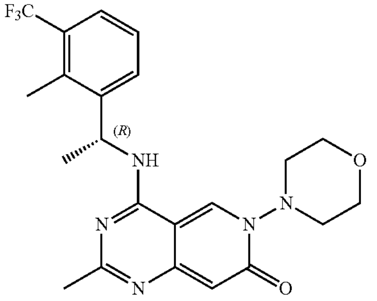 |
| Example 18 | 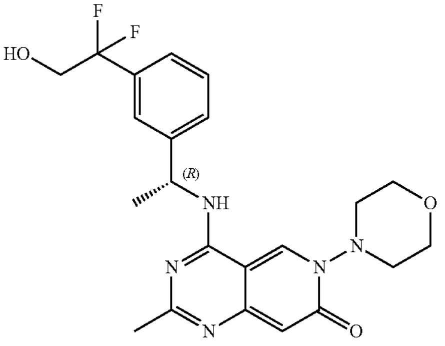 |

TABLE 1-continued
| ID | Structure |
| --- | --- |
| Example 19 | 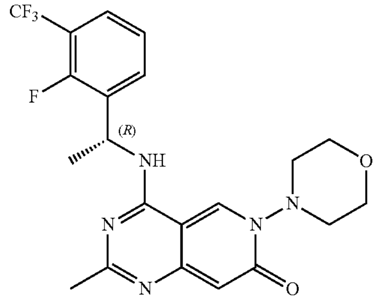 |
| Example 20 | 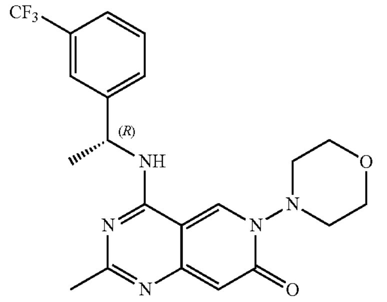 |
| Example 21 | 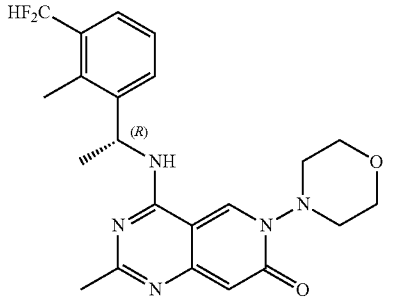 |
| Example 22 | 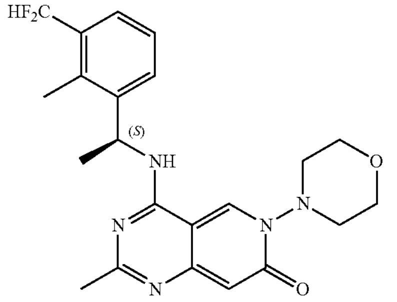 |
| Example 23 | 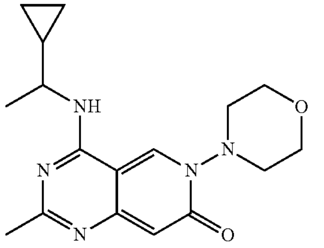 [SMILES: Cc1nc(NC(C)C2CC2)c2cn(N3CCOCC3)c(=O)cc2n1] |

TABLE 1-continued
| ID | Structure |
| --- | --- |
| Example 24 | 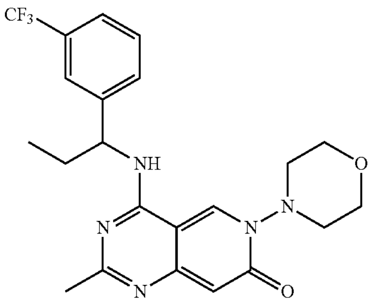 [SMILES: CCC(Nc1nc(C)nc2cc(=O)n(N3CCOCC3)cc12)c1cccc(C(F)(F)F)c1] |
| Example 25 | 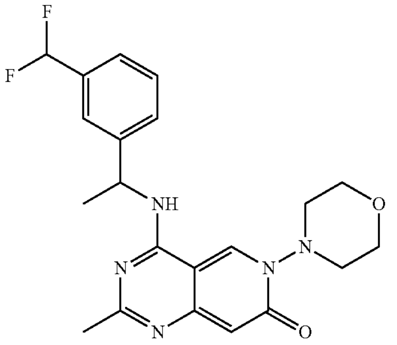 [SMILES: Cc1nc(NC(C)c2cccc(C(F)F)c2)c2cn(N3CCOCC3)c(=O)cc2n1] |
| Example 26 | 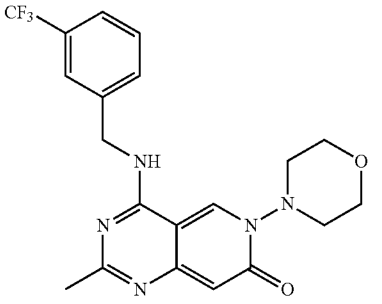 [SMILES: Cc1nc(NCc2cccc(C(F)(F)F)c2)c2cn(N3CCOCC3)c(=O)cc2n1] |
| Example 27 | 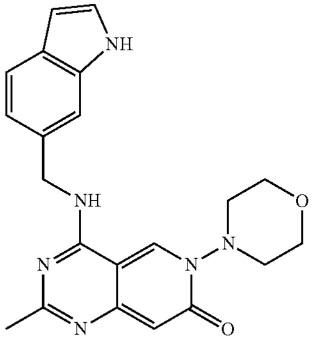 [SMILES: Cc1nc(NCc2ccc3cc[nH]c3c2)c2cn(N3CCOCC3)c(=O)cc2n1] |
| Example 28 | 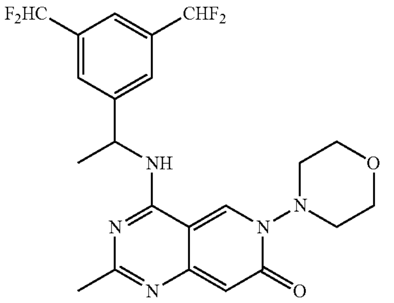 [SMILES: Cc1nc(NC(C)c2cc(C(F)F)cc(C(F)F)c2)c2cn(N3CCOCC3)c(=O)cc2n1] |

TABLE 1-continued
| ID | Structure |
| --- | --- |
| Example 29 | 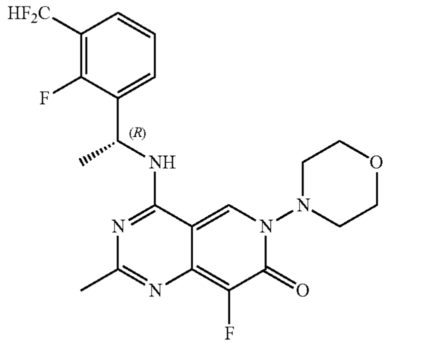 |
| Example 30 | 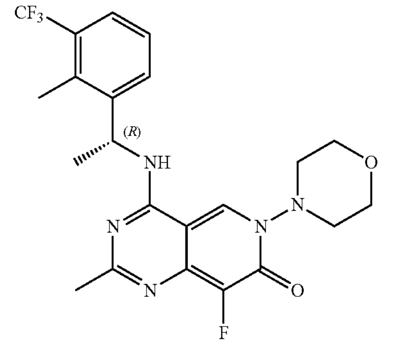 |
| Example 31 | 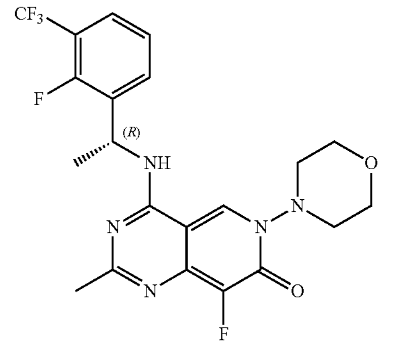 |
| Example 32 | 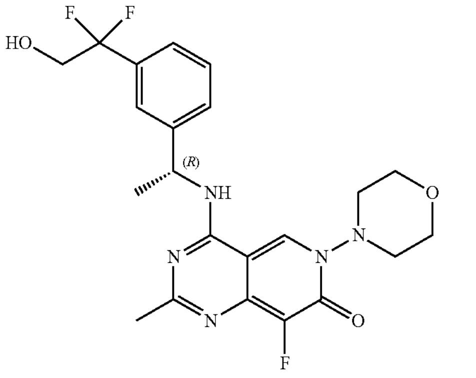 |

TABLE 1-continued
| ID | Structure |
|---|---|
| Example 33 | 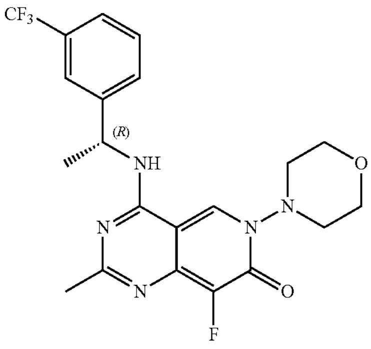 |
| Example 34 | 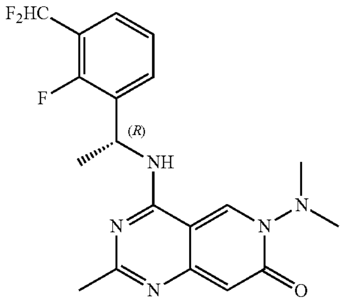 |
| Example 35 | 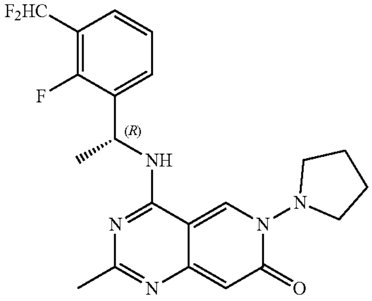 |
| Example 36 | 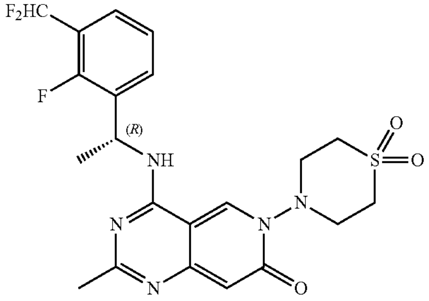 |
| Example 37 | 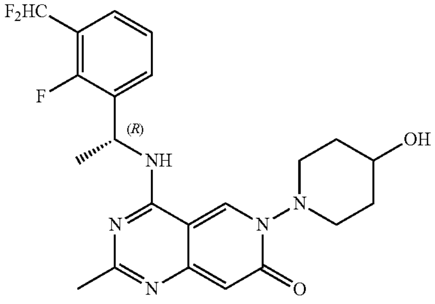 |

TABLE 1-continued
| ID | Structure |
| --- | --- |
| Example 38 | 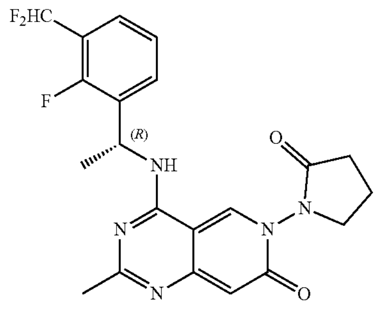 |
| Example 39 | 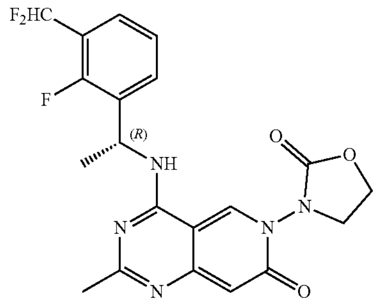 |
| Example 40 | 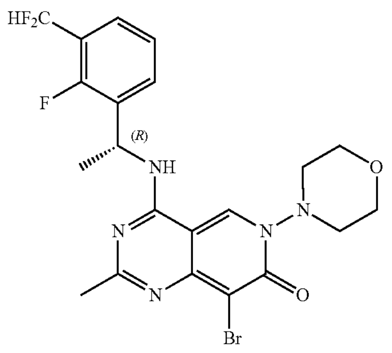 |
| Example 41 | 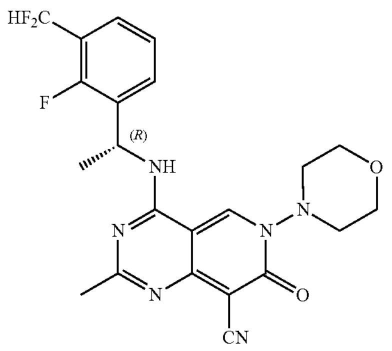 |

TABLE 1-continued
| ID | Structure |
| --- | --- |
| Example 42 | 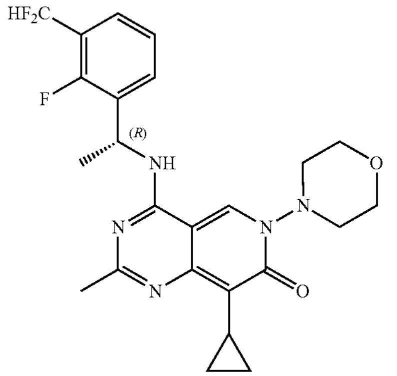 |
| Example 43 | 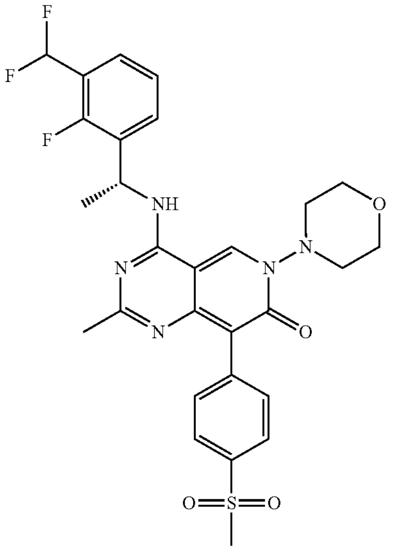 [SMILES: Cc1nc(N[C@H](C)c2cccc(C(F)F)c2F)c2cn(N3CCOCC3)c(=O)c(-c3ccc(S(C)(=O)=O)cc3)c2n1] |
| Example 44 | 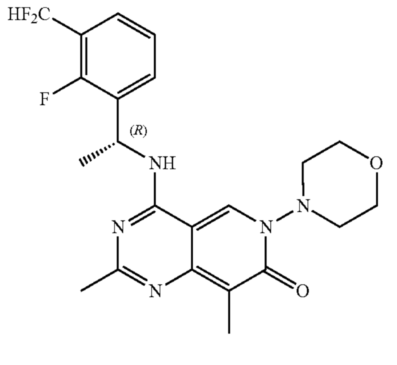 |

TABLE 1-continued
| ID | Structure |
|---|---|
| Example 45 | 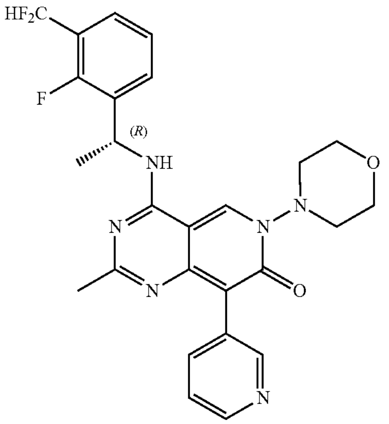 |
| Example 46 | 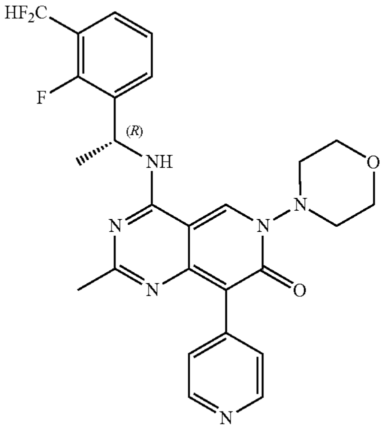 |
| Example 47 | 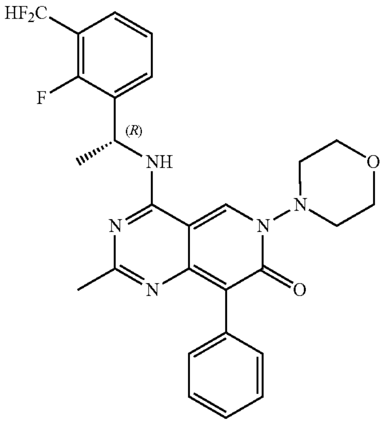 |

TABLE 1-continued
| ID | Structure |
|---|---|
| Example 48 | 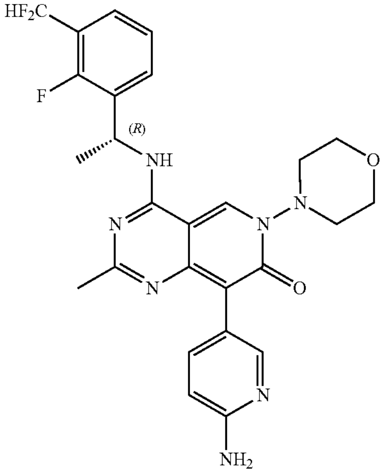 |
| Example 49 | 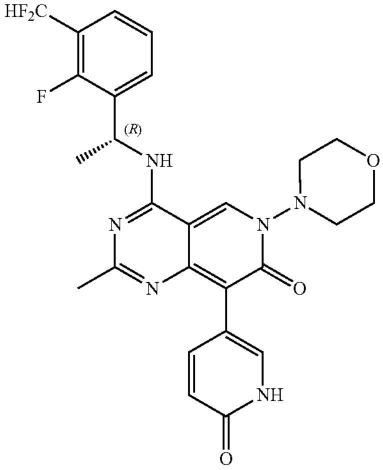 |
| Example 50 | 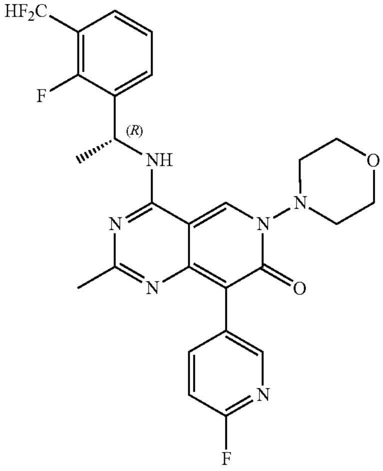 |

TABLE 1-continued
| ID | Structure |
| --- | --- |
| Example 51 | 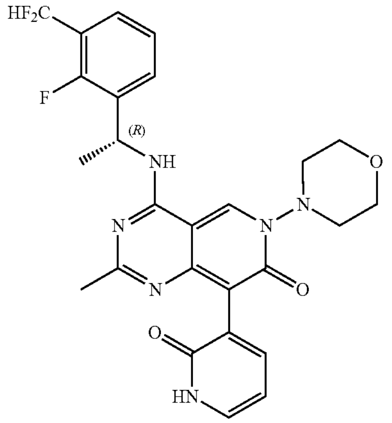 |
| Example 52 | 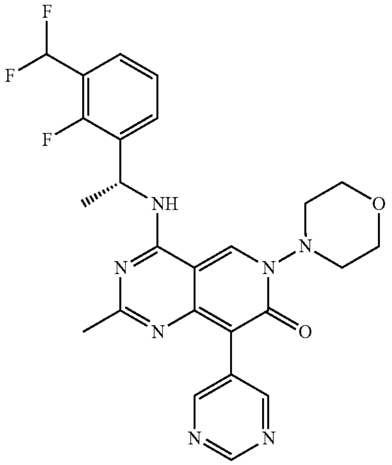 [SMILES: Cc1nc(N[C@H](C)c2cccc(C(F)F)c2F)c2cn(N3CCOCC3)c(=O)c(-c3cncnc3)c2n1] |
| Example 53 | 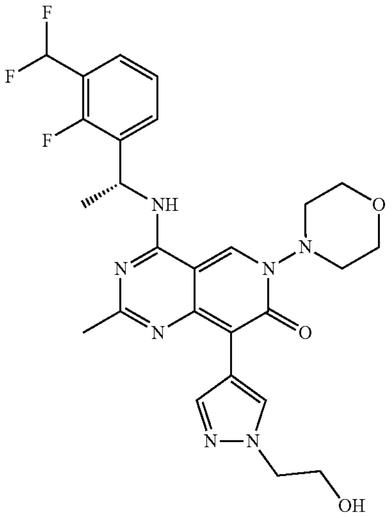 [SMILES: Cc1nc(N[C@H](C)c2cccc(C(F)F)c2F)c2cn(N3CCOCC3)c(=O)c(-c3cnn(CCO)c3)c2n1] |

TABLE 1-continued
| ID | Structure |
| --- | --- |
| Example 54 | 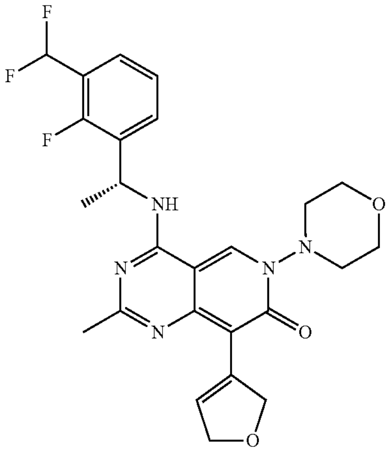 [SMILES: Cc1nc(N[C@H](C)c2cccc(C(F)F)c2F)c2cn(N3CCOCC3)c(=O)c(C3=CCOC3)c2n1] |
| Example 55 | 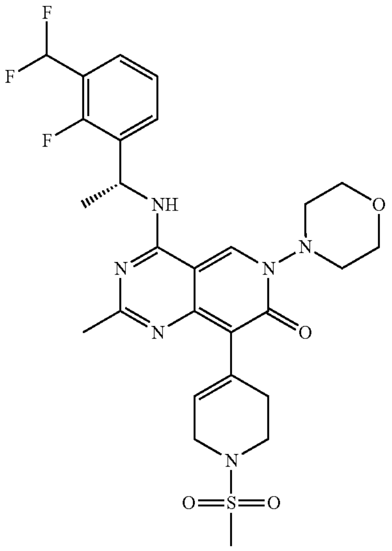 [SMILES: Cc1nc(N[C@H](C)c2cccc(C(F)F)c2F)c2cn(N3CCOCC3)c(=O)c(C3=CCN(S(C)(=O)=O)CC3)c2n1] |
| Example 56 | 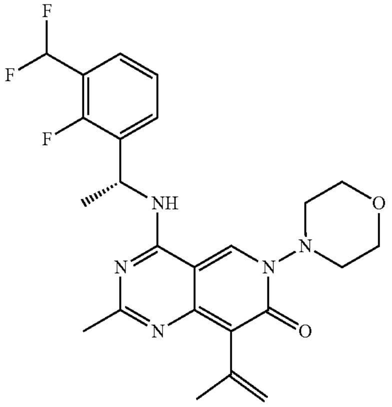 [SMILES: C=C(C)c1c(=O)n(N2CCOCC2)cc2c(N[C@H](C)c3cccc(C(F)F)c3F)nc(C)nc12] |

TABLE 1-continued
| ID | Structure |
| --- | --- |
| Example 57 | 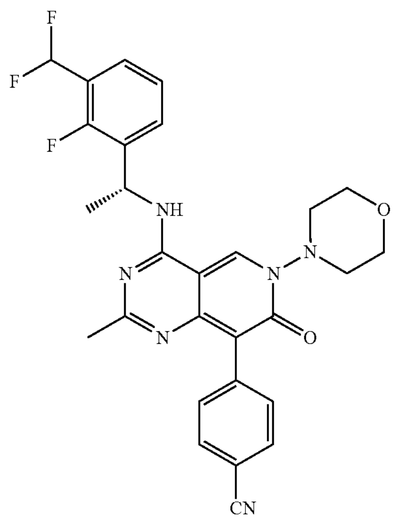 [SMILES: Cc1nc(N[C@H](C)c2cccc(C(F)F)c2F)c2cn(N3CCOCC3)c(=O)c(-c3ccc(C#N)cc3)c2n1] |
| Example 58 | 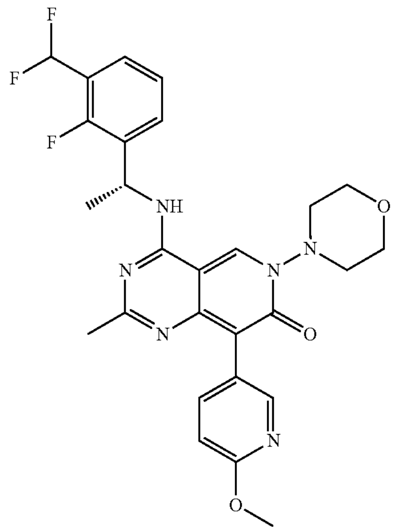 [SMILES: COc1ccc(-c2c(=O)n(N3CCOCC3)cc3c(N[C@H](C)c4cccc(C(F)F)c4F)nc(C)nc23)cn1] |
| Example 59 | 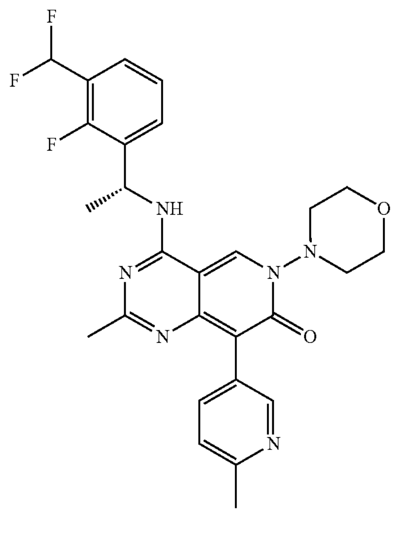 [SMILES: Cc1ccc(-c2c(=O)n(N3CCOCC3)cc3c(N[C@H](C)c4cccc(C(F)F)c4F)nc(C)nc23)cn1] |

TABLE 1-continued
| ID | Structure |
| --- | --- |
| Example 60 | 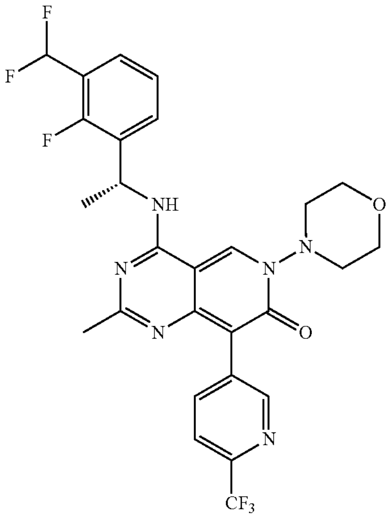 [SMILES: Cc1nc(N[C@H](C)c2cccc(C(F)F)c2F)c2cn(N3CCOCC3)c(=O)c(-c3ccc(C(F)(F)F)nc3)c2n1] |
| Example 61 | 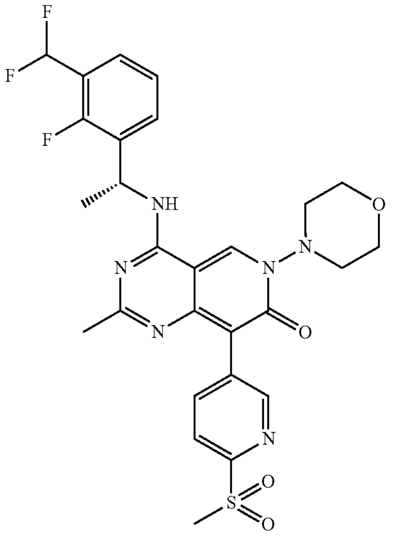 [SMILES: Cc1nc(N[C@H](C)c2cccc(C(F)F)c2F)c2cn(N3CCOCC3)c(=O)c(-c3ccc(S(C)(=O)=O)nc3)c2n1] |
| Example 62 | 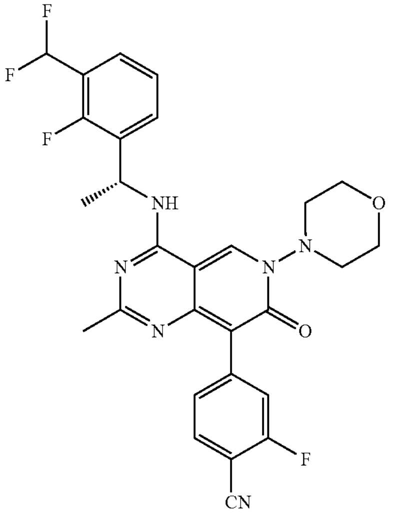 |

TABLE 1-continued
| ID | Structure |
| --- | --- |
| Example 63 | 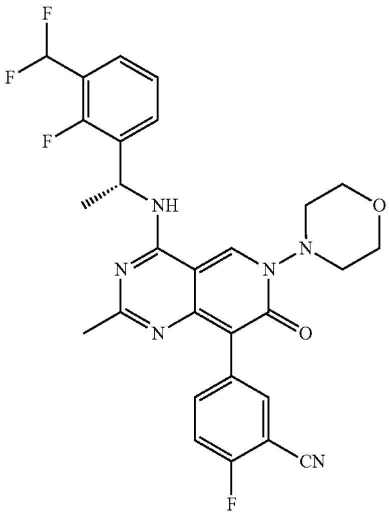 [SMILES: Cc1nc(N[C@H](C)c2cccc(C(F)F)c2F)c2cn(N3CCOCC3)c(=O)c(-c3ccc(F)c(C#N)c3)c2n1] |
| Example 64 | 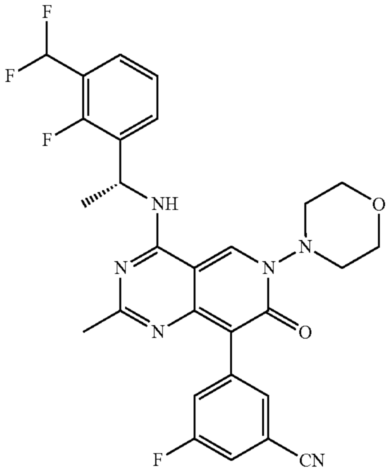 [SMILES: Cc1nc(N[C@H](C)c2cccc(C(F)F)c2F)c2cn(N3CCOCC3)c(=O)c(-c3cc(F)cc(C#N)c3)c2n1] |
| Example 65 | 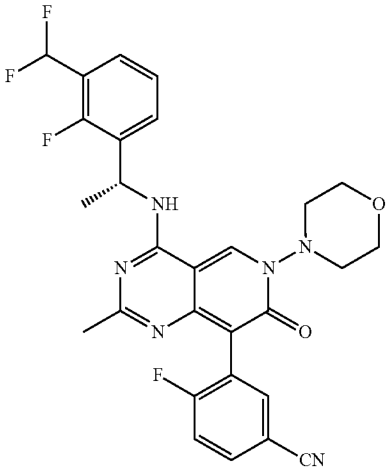 [SMILES: Cc1nc(N[C@H](C)c2cccc(C(F)F)c2F)c2cn(N3CCOCC3)c(=O)c(-c3cc(C#N)ccc3F)c2n1] |

TABLE 1-continued
| ID | Structure |
| --- | --- |
| Example 66 | 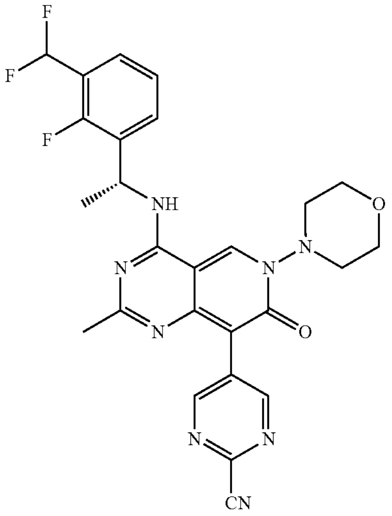 [SMILES: Cc1nc(N[C@H](C)c2cccc(C(F)F)c2F)c2cn(N3CCOCC3)c(=O)c(-c3cnc(C#N)nc3)c2n1] |
| Example 67 | 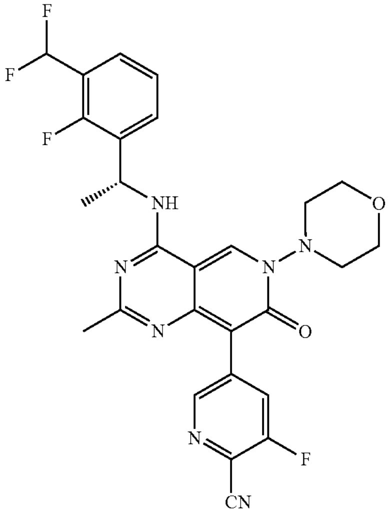 [SMILES: Cc1nc(N[C@H](C)c2cccc(C(F)F)c2F)c2cn(N3CCOCC3)c(=O)c(-c3cnc(C#N)c(F)c3)c2n1] |
| Example 68 | 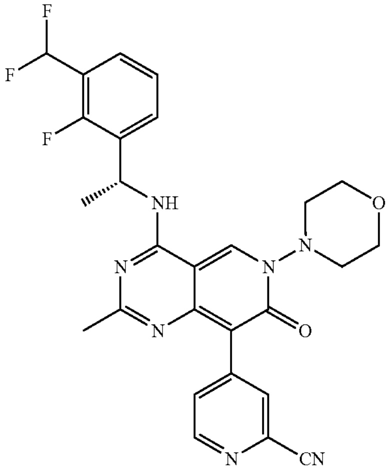 [SMILES: Cc1nc(N[C@H](C)c2cccc(C(F)F)c2F)c2cn(N3CCOCC3)c(=O)c(-c3ccnc(C#N)c3)c2n1] |

TABLE 1-continued
| ID | Structure |
| --- | --- |
| Example 69 | 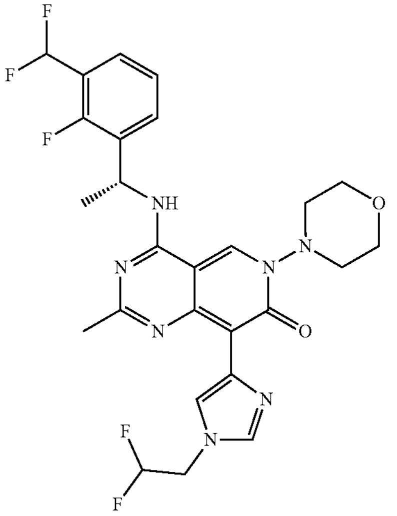 [SMILES: Cc1nc(N[C@H](C)c2cccc(C(F)F)c2F)c2cn(N3CCOCC3)c(=O)c(-c3cn(CC(F)F)cn3)c2n1] |
| Example 70 | 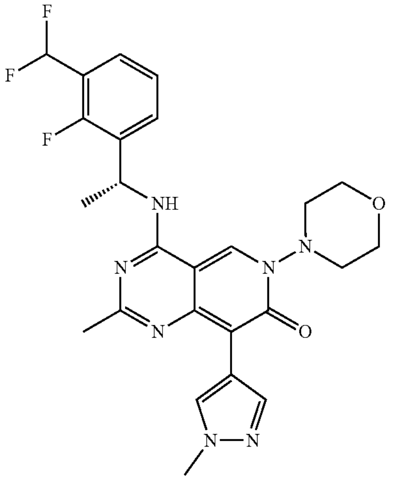 [SMILES: Cc1nc(N[C@H](C)c2cccc(C(F)F)c2F)c2cn(N3CCOCC3)c(=O)c(-c3cnn(C)c3)c2n1] |
| Example 71 | 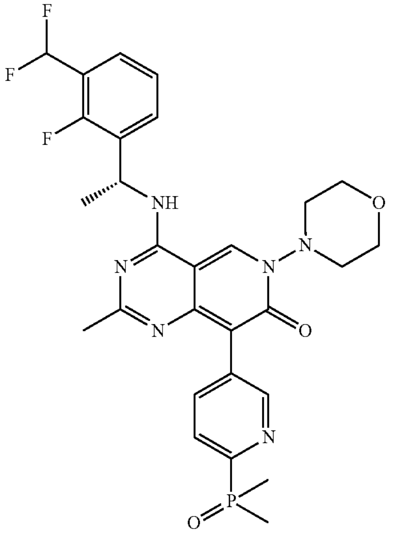 [SMILES: Cc1nc(N[C@H](C)c2cccc(C(F)F)c2F)c2cn(N3CCOCC3)c(=O)c(-c3ccc(P(C)(C)=O)nc3)c2n1] |

TABLE 1-continued
| ID | Structure |
| --- | --- |
| Example 72 | 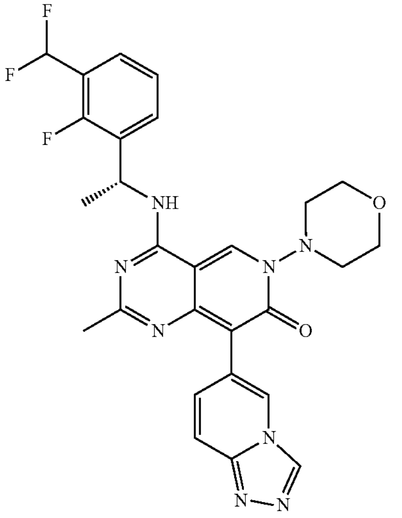 [SMILES: Cc1nc(N[C@H](C)c2cccc(C(F)F)c2F)c2cn(N3CCOCC3)c(=O)c(-c3ccc4nncn4c3)c2n1] |
| Example 73 | 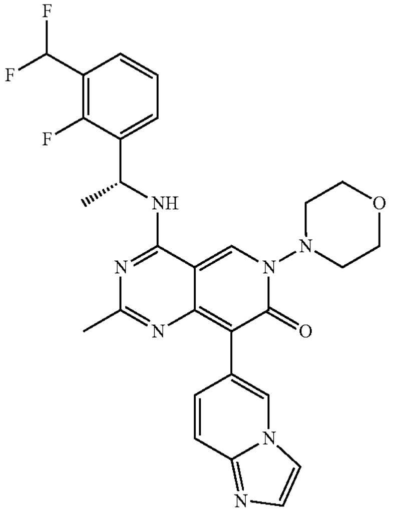 |
| Example 74 | 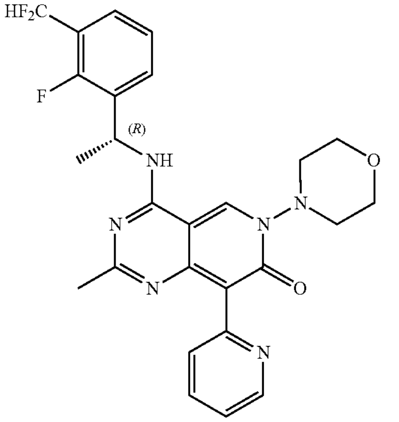 |

TABLE 1-continued
| ID | Structure |
| --- | --- |
| Example 75 | 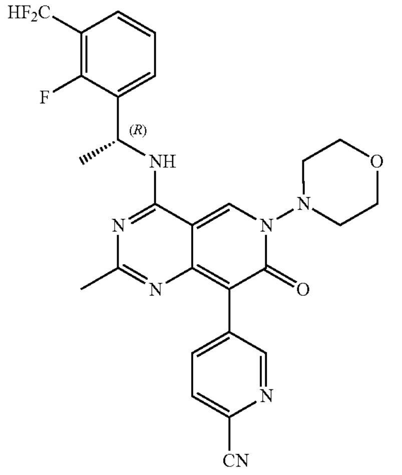 |
| Example 76 | 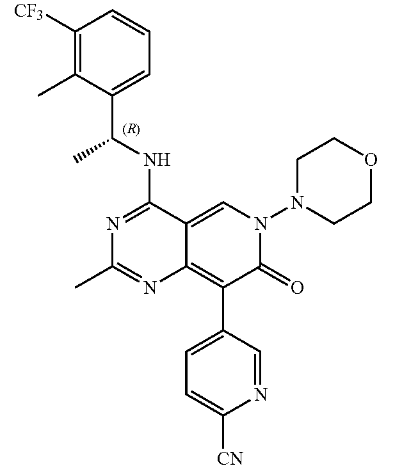 |
| Example 77 | 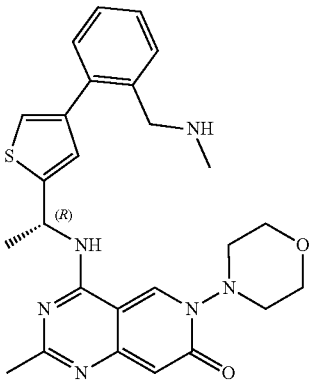 |

TABLE 1-continued
| ID | Structure |
| --- | --- |
| Example 78 | 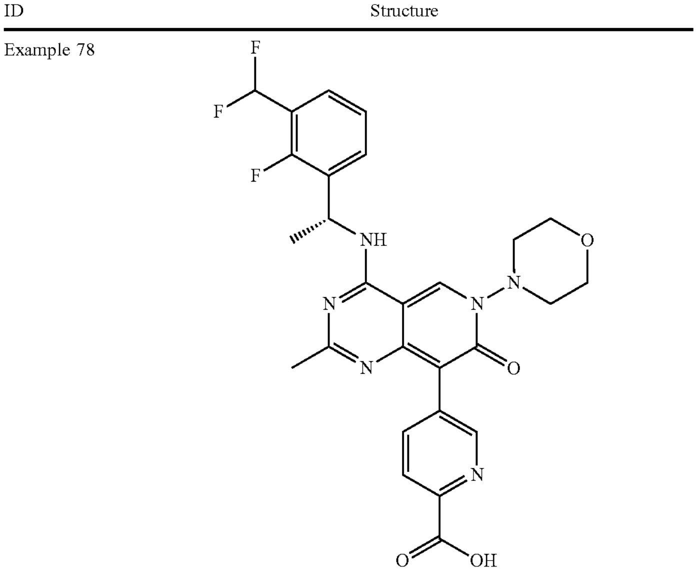 |
| Example 79 | 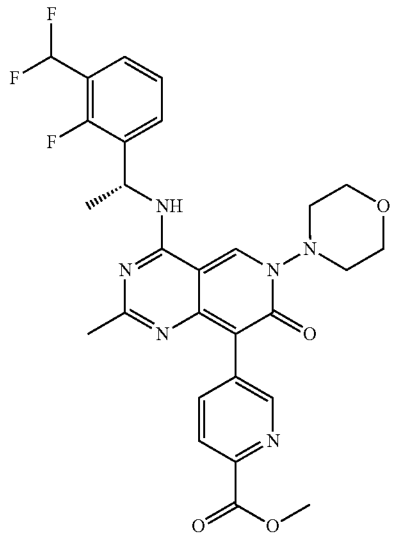 [SMILES: COC(=O)c1ccc(-c2c(=O)n(N3CCOCC3)cc3c(N[C@H](C)c4cccc(C(F)F)c4F)nc(C)nc23)cn1] |
| Example 80 | 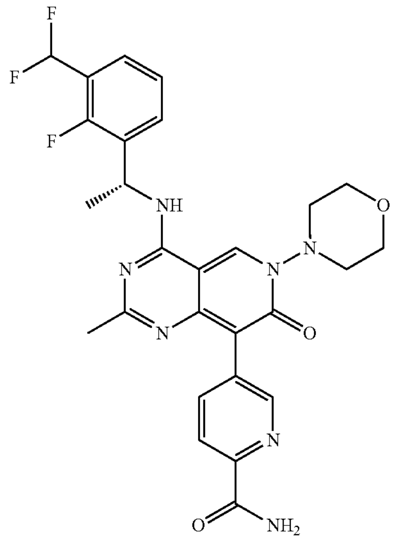 [SMILES: Cc1nc(N[C@H](C)c2cccc(C(F)F)c2F)c2cn(N3CCOCC3)c(=O)c(-c3ccc(C(N)=O)nc3)c2n1] |

TABLE 1-continued
| ID | Structure |
| --- | --- |
| Example 81 | 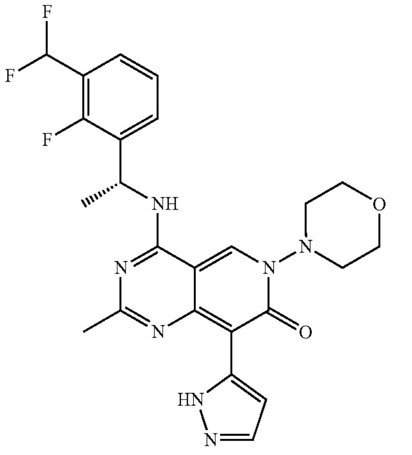 [SMILES: Cc1nc(N[C@H](C)c2cccc(C(F)F)c2F)c2cn(N3CCOCC3)c(=O)c(-c3ccn[nH]3)c2n1] |
| Example 82 | 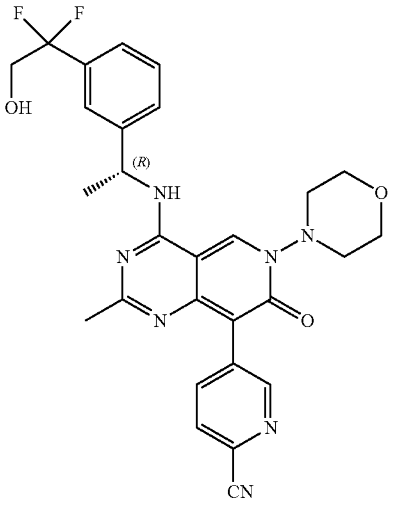 |
| Example 83 | 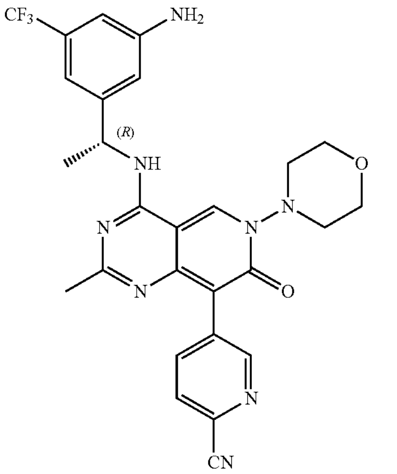 |

TABLE 1-continued
| ID | Structure |
| --- | --- |
| Example 84 | 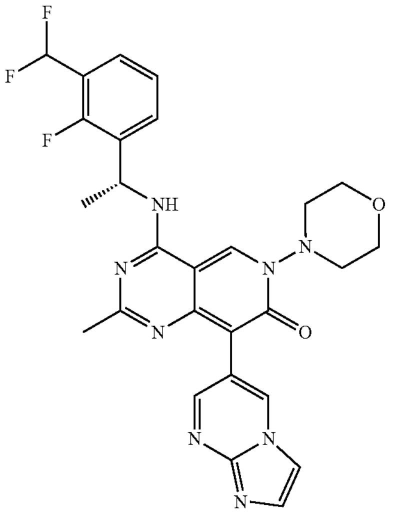 [SMILES: Cc1nc(N[C@H](C)c2cccc(C(F)F)c2F)c2cn(N3CCOCC3)c(=O)c(-c3cnc4nccn4c3)c2n1] |
| Example 85 | 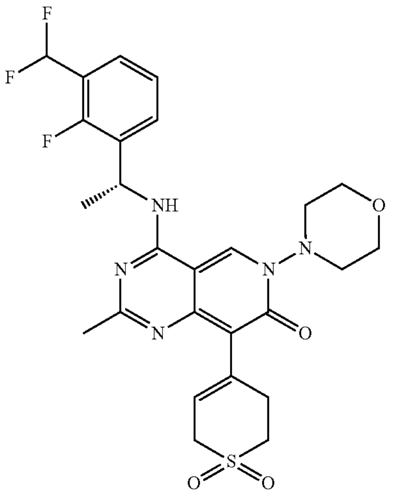 [SMILES: Cc1nc(N[C@H](C)c2cccc(C(F)F)c2F)c2cn(N3CCOCC3)c(=O)c(C3=CCS(=O)(=O)CC3)c2n1] |
| Example 86 | 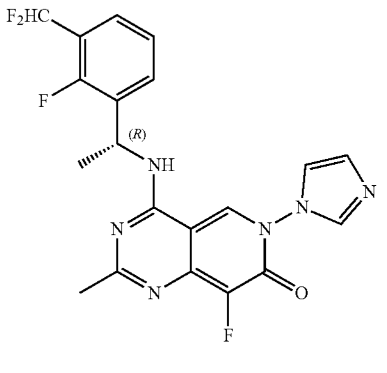 |

TABLE 1-continued

| ID | Structure |
|---|---|
| Example 87 | 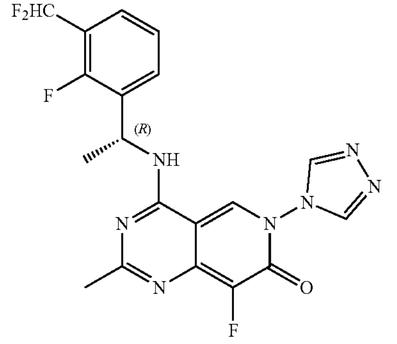 |

2. Definitions

The term "halogen," as used herein, refers to fluoride, chloride, bromide, or iodide.

The term "alkyl" used alone or as part of a larger moiety, such as "alkoxy" or "haloalkyl" and the like, means saturated aliphatic straight-chain or branched monovalent hydrocarbon radical of formula $—C_nH_{(2n+1)}$. Unless otherwise specified, an alkyl group typically has 1-6 carbon atoms, i.e. $C_{1-6}$alkyl. As used herein, a "$C_{1-6}$alkyl" group means a radical having from 1 to 6 carbon atoms in a linear or branched arrangement. Examples include methyl, ethyl, n-propyl, iso-propyl, n-butyl, iso-butyl, tert-butyl, n-pentyl, isopentyl, hexyl, and the like.

The term "alkylene" as used herein, means a straight or branched chain divalent hydrocarbon group of formula $—C_nH_{2n}—$. Non-limiting examples include ethylene, and propylene.

The term "alkenyl" means an alkyl group in which one or more carbon/carbon single bond is replaced by a double bond.

The term "alkynyl" means an alkyl group in which one or more carbon/carbon single bond is replaced by a triple bond.

The term "alkoxy" means an alkyl radical attached through an oxygen linking atom, represented by —O-alkyl. For example, "$(C_1-C_4)$alkoxy" includes methoxy, ethoxy, propoxy, and butoxy.

The term "haloalkyl" means alkyl, as the case may be, substituted with one or more halogen atoms.

The terms "hydroxyalkyl" means alkyl, as the case may be, substituted with one or more hydroxy groups.

The term "carbocyclyl" refers to any stable non-aromatic hydrocarbon ring having 3-12 membered carbocyclyl. In one embodiment, carbocyclyl is 3-, 4-, 5-, 6-, 7-, or 8-membered monocyclic or bicyclic or 7-, 8-, 9-, 10-, 11-, or 12-membered bicyclic or tricyclic hydrocarbon ring, any of which may be saturated, partially unsaturated, or unsaturated. Any substitutable ring atom can be substituted (e.g., by one or more substituents). Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, and cyclooctadienyl. In one embodiment, carbocyclyl is intended to include, bridged, fused, and spirocyclic rings. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cycloalkyl" refers to a cyclic, bicyclic, tricyclic, or polycyclic saturated hydrocarbon groups having 3 to 12 ring carbons. In one embodiment, cycloalkyl may have 3 to 7 ring carbons. Any substitutable ring atom can be substituted (e.g., by one or more substituents). Examples of cycloalkyl groups include, without limitation, cyclopropyl, cyclobutyl, cyclopentyl, cyclohexyl, cycloheptyl, and cyclooctyl. Cycloalkyl may include multiple fused and/or bridged rings. Non-limiting examples of fused/bridged cycloalkyl include: bicyclo[1.1.0]butane, bicyclo[2.1.0]pentane, bicyclo[1.1.0]pentane, bicyclo[3.1.0]hexane, bicyclo[2.1.1]hexane, bicyclo[3.2.0]heptane, bicyclo[4.1.0]heptane, bicyclo[2.2.1]heptane, bicyclo[3.1.1]heptane, bicyclo[4.2.0]octane, bicyclo[3.2.1]octane, bicyclo[2.2.2]octane, and the like. Cycloalkyl also includes spirocyclic rings (e.g., spirocyclic bicycle wherein two rings are connected through just one atom). Non-limiting examples of spirocyclic cycloalkyls include spiro[2.2]pentane, spiro[2.5]octane, spiro[3.5]nonane, spiro[3.5]nonane, spiro[3.5]nonane, spiro[4.4]nonane, spiro[2.6]nonane, spiro[4.5]decane, spiro[3.6]decane, spiro[5.5]undecane, and the like.

The term "heterocyclyl" or "heterocyclic" refers to a radical of a 3- to 12-membered non-aromatic ring system having ring carbon atoms and 1 to 4 ring heteroatoms, wherein each heteroatom is independently selected from nitrogen, quaternary nitrogen, oxidized nitrogen (e.g., NO), oxygen, and sulfur, including sulfoxide and sulfone ("3-12 membered heterocyclyl"). In some embodiments, a heterocyclyl group is a 3-7 membered non-aromatic ring system having ring carbon atoms and 1-4 ring heteroatoms, wherein each heteroatom is independently selected from nitrogen, oxygen, and sulfur ("3-7 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a bicyclic system ("bicyclic heterocyclyl") or tricyclic system ("tricyclic heterocyclyl"); polycyclic ring systems include fused, bridged, or spiro ring systems). Exemplary monocyclic heterocyclyl groups include azetidinyl, oxetanyl, thietanyl, tetrahydrofuranyl, pyrrolidinyl, piperidinyl, tetrahydropyranyl, piperazinyl, morpholinyl, azepanyl, oxepanyl, thiepanyl, tetrahydropyridinyl, and the like. Heterocyclyl polycyclic ring systems can include heteroatoms in one or more rings in the polycyclic ring system. Substituents may be present on one or more rings in the polycyclic ring system.

Spiro heterocyclyl refers to 5 to 12 membered polycyclic heterocyclyl with rings connected through one common carbon atom (called as spiro atom), wherein said rings have one or more heteroatoms selected from the group consisting of nitrogen, quaternary nitrogen, oxidized nitrogen (e.g., NO), oxygen, and sulfur, including sulfoxide and sulfone, the remaining ring atoms being C, wherein one or more rings may contain one or more double bonds, but none of the rings has a completely conjugated pi-electron system. Representative examples of spiro heterocyclyl include, but are not limited to the following groups:

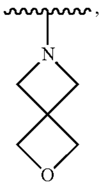,
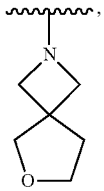,
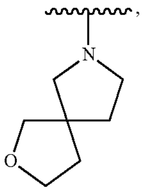, and
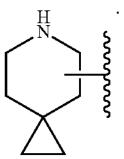.

Fused heterocyclyl refers to a 5 to 12 membered polycyclic heterocyclyl group, wherein each ring in the group shares an adjacent pair of carbon atoms with another ring in the group, wherein one or more rings can contain one or more double bonds, but at least one of the rings does not have a completely conjugated π-electron system, and wherein said rings have one or more heteroatoms selected from the group consisting of nitrogen, quaternary nitrogen, oxidized nitrogen (e.g., NO), oxygen, and sulfur, including sulfoxide and sulfone, the remaining ring atoms being C. Representative examples of fused heterocyclyl include, but are not limited to the following groups:

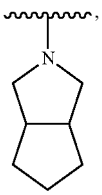,
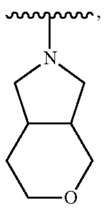,
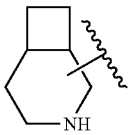, and
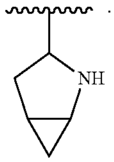.

Bridged heterocyclyl refers to a 5 to 12 membered polycyclic heterocyclyl group, wherein any two rings in the group share two disconnected atoms, the rings can have one or more double bonds but have no completely conjugated π-electron system, and the rings have one or more heteroatoms selected from the group consisting of nitrogen, quaternary nitrogen, oxidized nitrogen (e.g., NO), oxygen, and sulfur, including sulfoxide and sulfone as ring atoms, the remaining ring atoms being C. Representative examples of bridged heterocyclyl include, but are not limited to the following groups:

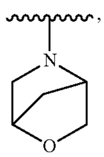,
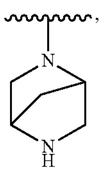,
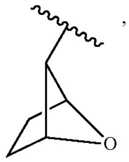, and
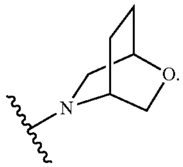.

Generally, the carbocyclyl, the cycloalkyl, or the heterocyclyl may be unsubstituted, or be substituted with one or more substituents as valency allows, wherein the substituents can be independently selected from a number of groups such as oxo, —CN, halogen, alkyl and alkoxyl, optionally, the alkyl substitution may be further substituted.

The term "aryl" refers to a 6 to 10 membered all-carbon monocyclic ring or a polycyclic fused ring (a "fused" ring system means that each ring in the system shares an adjacent pair of carbon atoms with other ring in the system) group, and has a completely conjugated π-electron system. Representative examples of aryl are phenyl and naphthyl.

The term "heteroaryl," as used herein, refers to a monocyclic or multicyclic aromatic hydrocarbon in which at least one of the ring carbon atoms has been replaced with a heteroatom independently selected from oxygen, nitrogen and sulfur. Preferably, the heteroaryl is based on a $C_{5-10}$ aryl with one or more of its ring carbon atoms replaced by the heteroatom. A heteroaryl group may be attached through a ring carbon atom or, where valency permits, through a ring nitrogen atom. Generally, the heteroaryl may be unsubstituted, or be substituted with one or more substituents as valency allows with the substituents being independently selected from halogen, OH, alkyl, alkoxyl, and amino (e.g., $NH_2$, NHalkyl, $N(alkyl)_2$), optionally, the alkyl may be further substituted.

As used herein, the term "treating" includes any effect, e.g., lessening, reducing, modulating, ameliorating, or eliminating, that results in the improvement of the condition, disease, disorder, and the like, or ameliorating a symptom thereof.

The term "therapeutically effective amount" refers to an amount of an agent (e.g., a compound described herein) effective to treat at least one symptom of a disease or disorder in a patient or subject. The "therapeutically effective amount" of the agent for administration may vary based upon the desired activity, the disease state of the patient or subject being treated, the dosage form, method of administration, patient factors such as the patient's sex, genotype, weight and age, the underlying causes of the condition or disease to be treated, the route of administration and bioavailability, the persistence of the administered agent in the body, evidence of natriuresis and/or diuresis, the type of formulation, and the potency of the agent.

Pharmaceutically Acceptable Salts

The term "pharmaceutically-acceptable salt" refers to a pharmaceutical salt that is, within the scope of sound medical judgment, suitable for use in contact with the tissues of humans and lower animals without undue toxicity, irritation, and allergic response, and is commensurate with a reasonable benefit/risk ratio. Pharmaceutically-acceptable salts are well known in the art. For example, S. M. Berge et al. describes pharmacologically acceptable salts in J. Pharm. Sci., 1977, 66, 1-19.

Pharmaceutically acceptable salts of the compounds of any one of the formulae described above include acid addition and base salts.

Included in the present teachings are pharmaceutically acceptable salts of the compounds disclosed herein. Compounds having basic groups can form pharmaceutically acceptable salts with pharmaceutically acceptable acid(s). Suitable pharmaceutically acceptable acid addition salts of the compounds described herein include salts of inorganic acids (such as hydrochloric, hydrobromic, phosphoric, metaphosphoric, nitric, and sulfuric acids) and of organic acids (such as acetic, benzenesulfonic, benzoic, ethanesulfonic, methanesulfonic, and succinic acids). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts).

Pharmaceutically acceptable salts of compounds of any one of the formulae described above may be prepared by one or more of three methods:

(i) by reacting the compound of any one of the formulae described above with the desired acid or base;

(ii) by removing an acid- or base-labile protecting group from a suitable precursor of the compound of any one of the formulae described above or by ring-opening a suitable cyclic precursor, for example, a lactone or lactam, using the desired acid or base; or (iii) by converting one salt of the compound of any one of the formulae described above to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of any one of the formulae described above, and pharmaceutically acceptable salts thereof, may exist in unsolvated and solvated forms.

Stereoisomers and Other Variations

The compounds of any one of the formulae described above may exhibit one or more kinds of isomerism (e.g. optical, geometric or tautomeric isomerism). Such variation is implicit to the compounds of any one of the formulae described above defined as they are by reference to their structural features and therefore within the scope of the present disclosure.

Compounds having one or more chiral centers can exist in various stereoisomeric forms, i.e., each chiral center can have an R or S configuration, or can be a mixture of both. Stereoisomers are compounds that differ only in their spatial arrangement. Stereoisomers include all diastereomeric and enantiomeric forms of a compound. Enantiomers are stereoisomers that are mirror images of each other. Diastereomers are stereoisomers having two or more chiral centers that are not identical and are not mirror images of each other.

When a compound is designated by its chemical name (e.g., where the configuration is indicated in the chemical name by "R" or "S") or its structure (e.g., the configuration is indicated by "wedge" bonds) that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers is included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

When two stereoisomers are depicted by their chemical names or structures, and the chemical names or structures are connected by an "and", a mixture of the two stereoisomers is intended.

When two stereoisomers are depicted by their chemical names or structures, and the names or structures are connected by an "or", one or the other of the two stereoisomers is intended, but not both.

When a disclosed compound having a chiral center is depicted by a structure without showing a configuration at that chiral center, the structure is meant to encompass the compound with the S configuration at that chiral center, the compound with the R configuration at that chiral center, or the compound with a mixture of the R and S configuration at that chiral center. When a disclosed compound having a chiral center is depicted by its chemical name without indicating a configuration at that chiral center with "S" or "R", the name is meant to encompass the compound with the S configuration at that chiral center, the compound with the R configuration at that chiral center or the compound with a mixture of the R and S configuration at that chiral center.

Racemic mixture means 50% of one enantiomer and 50% of is corresponding enantiomer. When a compound with one chiral center is named or depicted without indicating the stereochemistry of the chiral center, it is understood that the name or structure encompasses both possible enantiomeric forms (e.g., both enantiomerically-pure, enantiomerically-enriched or racemic) of the compound. When a compound with two or more chiral centers is named or depicted without indicating the stereochemistry of the chiral centers, it is understood that the name or structure encompasses all possible diasteriomeric forms (e.g., diastereomerically pure, diastereomerically enriched and equimolar mixtures of one or more diastereomers (e.g., racemic mixtures) of the compound.

The term "geometric isomer" refers to compounds having at least one double bond, wherein the double bond(s) may exist in cis (also referred to as syn or entgegen (E)) or trans (also referred to as anti or zusammen (Z)) forms as well as mixtures thereof.

Where structural isomers are interconvertible via a low energy barrier, tautomeric isomerism ("tautomerism") can occur. This can take the form of proton tautomerism in compounds of any one of the formulae described above containing, for example, an imino, keto, or oxime group, or so-called valence tautomerism in compounds which contain an aromatic moiety. It follows that a single compound may exhibit more than one type of isomerism.

When a geometric isomer is depicted by name or structure, it is to be understood that the named or depicted isomer exists to a greater degree than another isomer, that is that the geometric isomeric purity of the named or depicted geometric isomer is greater than 50%, such as at least 60%, 70%, 80%, 90%, 99%, or 99.9% pure by weight. Geometric isomeric purity is determined by dividing the weight of the named or depicted geometric isomer in the mixture by the total weight of all of the geometric isomers in the mixture.

Cis/trans isomers may be separated by conventional techniques well known to those skilled in the art, for example, chromatography and fractional crystallisation.

Conventional techniques for the preparation/isolation of individual enantiomers/diastereomers include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of any one of the formulae described above contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person. Chiral compounds of any one of the formulae described above (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture. Chiral chromatography using sub- and supercritical fluids may be employed. Methods for chiral chromatography useful in some embodiments of the present disclosure are known in the art (see, for example, Smith, Roger M., Loughborough University, Loughborough, UK; Chromatographic Science Series (1998), 75 (Supercritical Fluid Chromatography with Packed Columns), pp. 223-249 and references cited therein). Columns can be obtained from Chiral Technologies, Inc, West Chester, Pa., USA, a subsidiary of Daicel® Chemical Industries, Ltd., Tokyo, Japan.

It must be emphasized that the compounds of any one of the formulae described above have been drawn herein in a single tautomeric form, all possible tautomeric forms are included within the scope of the present disclosure.

3. Administration and Dosing

Typically, a compound of the present disclosure is administered in an amount effective to treat a condition as described herein. The compounds of the present disclosure can be administered as compound per se, or alternatively, as a pharmaceutically acceptable salt. For administration and dosing purposes, the compound per se or pharmaceutically acceptable salt thereof will simply be referred to as the compounds of the present disclosure.

The compounds of the present disclosure are administered by any suitable route in the form of a pharmaceutical composition adapted to such a route, and in a dose effective for the treatment intended. The compounds of the present disclosure may be administered orally, rectally, vaginally, parenterally, or topically.

The compounds of the present disclosure may be administered orally. Oral administration may involve swallowing, so that the compound enters the gastrointestinal tract, or buccal or sublingual administration may be employed by which the compound enters the bloodstream directly from the mouth.

In another embodiment, the compounds of the present disclosure may also be administered directly into the bloodstream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the present disclosure may also be administered topically to the skin or mucosa, that is, dermally or transdermally. In another embodiment, the compounds of the present disclosure can also be administered intranasally or by inhalation. In another embodiment, the compounds of the present disclosure may be administered rectally or vaginally. In another embodiment, the compounds of the present disclosure may also be administered directly to the eye or ear.

The dosage regimen for the compounds of the present disclosure and/or compositions containing said compounds is based on a variety of factors, including the type, age, weight, sex and medical condition of the patient; the severity of the condition; the route of administration; and the activity of the particular compound employed. Thus the dosage regimen may vary widely. In one embodiment, the total daily dose of a compound of the present disclosure is typically from about 0.001 to about 100 mg/kg (i.e., mg compound of the present disclosure per kg body weight) for the treatment of the indicated conditions discussed herein.

For oral administration, the compositions may be provided in the form of tablets containing 0.1-500 milligrams of the active ingredient for the symptomatic adjustment of the dosage to the patient. A medicament typically contains from about 0.01 mg to about 500 mg of the active ingredient. Intravenously, doses may range from about 0.01 to about 10 mg/kg/minute during a constant rate infusion.

Suitable subjects according to the present disclosure include mammalian subjects, including non-human mammal such as primates, rodents (mice, rats, hamsters, rabbits etc). In one embodiment, humans are suitable subjects. Human subjects may be of either gender and at any stage of development.

4. Pharmaceutical Compositions

In another embodiment, the present disclosure comprises pharmaceutical compositions. Such pharmaceutical compositions comprise a compound of the present disclosure presented with a pharmaceutically acceptable carrier or excipient. Other pharmacologically active substances can also be present.

As used herein, "pharmaceutically acceptable carrier or excipient" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof, and may include isotonic agents, for example, sugars, sodium chloride, or polyalcohols such as mannitol, or sorbitol in the composition. Pharmaceutically acceptable substances such as wetting agents or minor amounts of auxiliary substances such as wetting or emulsifying agents, preservatives or buffers, which enhance the shelf life or effectiveness of the antibody or antibody portion.

The compositions of present disclosure may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form depends on the intended mode of administration and therapeutic application.

Typical compositions are in the form of injectable or infusible solutions, such as compositions similar to those used for passive immunization of humans with antibodies in general. One mode of administration is parenteral (e.g. intravenous, subcutaneous, intraperitoneal, intramuscular). In another embodiment, the antibody is administered by intravenous infusion or injection. In yet another embodiment, the antibody is administered by intramuscular or subcutaneous injection.

Oral administration of a solid dose form may be, for example, presented in discrete units, such as hard or soft capsules, pills, cachets, lozenges, or tablets, each containing a predetermined amount of at least one compound of the present disclosure. In another embodiment, the oral administration may be in a powder or granule form. In another embodiment, the oral dose form is sub-lingual, such as, for example, a lozenge. In such solid dosage forms, the compounds of any one of the formulae described above are ordinarily combined with one or more adjuvants. Such capsules or tablets may contain a controlled release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present disclosure comprises a parenteral dose form.

"Parenteral administration" includes, for example, subcutaneous injections, intravenous injections, intraperitoneally, intramuscular injections, intrasternal injections, and infusion. Injectable preparations (i.e., sterile injectable aqueous or oleaginous suspensions) may be formulated according to the known art using suitable dispersing, wetting agents, and/or suspending agents.

In another embodiment, the present disclosure comprises a topical dose form.

"Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of present disclosure are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, Finnin and Morgan, *J. Pharm. Sci.,* 88:955-958, 1999.

Formulations suitable for topical administration to the eye include, for example, eye drops wherein the compound of present disclosure is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed linked polyacrylic acid, polyvinyl alcohol, hyaluronic acid, a cellulosic polymer, for example, hydroxypropylmethylcellulose, hydroxyethylcellulose, or methylcellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the compounds of the present disclosure are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present disclosure comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the present disclosure may be prepared by any of the well-known techniques of pharmacy, such as effective formulation and administration procedures.

The above considerations in regard to effective formulations and administration procedures are well known in the art and are described in standard textbooks. Formulation of drugs is discussed in, for example, Hoover, John E., *Remington's Pharmaceutical Sciences*, Mack Publishing Co., Easton, Pa., 1975; Liberman et al., Eds., *Pharmaceutical Dosage Forms*, Marcel Decker, New York, N.Y., 1980; and Kibbe et al., Eds., *Handbook of Pharmaceutical Excipients* ($3^{rd}$ Ed.), American Pharmaceutical Association, Washington, 1999.

5. Method of Treatment

The present disclosure is directed to SOS1 inhibitor compounds, in particular compounds of formula (I), (II), (III-A), or (III-B) (including all its embodiments), which are useful in the treatment and/or prevention of a disease and/or condition associated with or modulated by SOS1, especially wherein the inhibition of the interaction of SOS1 and a RAS-family protein and/or RAC1 is of therapeutic benefit, including but not limited to the treatment and/or prevention of cancer.

In one embodiment, the present disclosure relates to a compound of formula (I), (II), (III-A), or (III-B), a pharmaceutically acceptable salt, or a stereoisomer thereof for use as a medicament.

In one embodiment, the present disclosure relates to a compound of (I), (II), (III-A), or (III-B), a pharmaceutically acceptable salt, or a stereoisomer thereof for use in a method of treatment of the human or animal body.

In one embodiment, the present disclosure relates to a SOS1 inhibitor compound, in particular a compound of (I), (II), (III-A), or (III-B), a pharmaceutically acceptable salt, or a stereoisomer thereof for use in the treatment and/or prevention of a disease and/or condition wherein the inhibition of the interaction of SOS1 and a RAS-family protein and/or RAC1 is of therapeutic benefit, including but not limited to the treatment and/or prevention of cancer.

In one embodiment, the present disclosure relates to a SOS1 inhibitor compound, in particular a compound of (I), (II), (III-A), or (III-B), a pharmaceutically acceptable salt, or a stereoisomer thereof for use in the treatment and/or prevention of cancer.

In one embodiment, the present disclosure relates to a SOS1 inhibitor compound, in particular a compound of formula (I), (II), (III-A), or (III-B), a pharmaceutically acceptable salt, or a stereoisomer thereof for use in a method of treatment and/or prevention of cancer in the human or animal body.

In one embodiment, the present disclosure relates to a SOS1 inhibitor compound, in particular a compound of formula (I), (II), (III-A), or (III-B), a pharmaceutically acceptable salt, or a stereoisomer thereof for use as hereinbefore defined wherein said SOS1 inhibitor compound is administered before, after or together with at least one other pharmacologically active substance.

In one embodiment, the present disclosure relates to a SOS1 inhibitor compound—or a pharmaceutically acceptable salt thereof—for use as hereinbefore defined, wherein said SOS1 inhibitor compound is administered in combination with at least one other pharmacologically active substance.

In one embodiment, the present disclosure relates to a compound of formula (I), (II), (III-A), or (III-B), a pharmaceutically acceptable salt, or a stereoisomer thereof for use as hereinbefore defined, wherein said compound is administered in combination with at least one other pharmacologically active substance.

In one embodiment, the present disclosure relates to a pharmacologically active substance prepared for being administered before, after or together with a SOS1 inhibitor compound—or a pharmaceutically acceptable salt thereof—for use as hereinbefore defined for the use of the compound of formula (I), (II), (III-A), or (III-B), a pharmaceutically acceptable salt, or a stereoisomer thereof.

In one embodiment, the present disclosure relates to a pharmacologically active substance prepared for being administered before, after or together with a compound of formula (I), (II), (III-A), or (III-B), a pharmaceutically acceptable salt, or a stereoisomer thereof for use as hereinbefore defined for the use of the compound of formula (I), (II), (III-A), or (III-B), a pharmaceutically acceptable salt, or a stereoisomer thereof.

In one embodiment, the present disclosure relates to a SOS1 inhibitor compound, in particular a compound of formula (I), (II), (III-A), or (III-B), a pharmaceutically acceptable salt, or a stereoisomer thereof for use in the treatment or in a method of treatment as hereinbefore defined.

In one embodiment, the present disclosure relates to the use of a SOS1 inhibitor compound, in particular a compound of formula (I), (II), (III-A), or (III-B), a pharmaceutically acceptable salt, or a stereoisomer thereof for preparing a pharmaceutical composition for the treatment and/or prevention of cancer.

In one embodiment, the present disclosure relates to the use of a SOS1 inhibitor compound—or a pharmaceutically acceptable salt thereof—as hereinbefore defined wherein said SOS1 inhibitor compound is administered before, after or together with at least one other pharmacologically active substance.

In one embodiment, the present disclosure relates to the use of a compound of formula (I), (II), (III-A), or (III-B), a pharmaceutically acceptable salt, or a stereoisomer thereof as hereinbefore defined wherein said compound is administered before, after or together with at least one other pharmacologically active substance.

In one embodiment, the present disclosure relates to the use of a SOS1 inhibitor compound, in particular a compound of formula (I), (II), (III-A), or (III-B), a pharmaceutically acceptable salt, or a stereoisomer thereof as hereinbefore defined for the treatment.

In one embodiment, the present disclosure relates to a method for the treatment and/or prevention of a disease and/or condition wherein the inhibition of the interaction of SOS1 and a RAS-family protein or RAC1 is of therapeutic benefit comprising administering a therapeutically effective amount of a SOS1 inhibitor compound, in particular a compound of formula (I), (II), (III-A), or (III-B), a pharmaceutically acceptable salt, or a stereoisomer thereof to a human being.

In one embodiment, the present disclosure relates to a method for the treatment and/or prevention of cancer comprising administering a therapeutically effective amount of a SOS1 inhibitor compound, in particular a compound of formula (I), (II), (III-A), or (III-B), a pharmaceutically acceptable salt, or a stereoisomer thereof to a human being.

In one embodiment, the present disclosure relates to a method as hereinbefore defined wherein the SOS1 inhibitor compound—or a pharmaceutically acceptable salt thereof—is administered before, after or together with at least one other pharmacologically active substance.

In one embodiment, the present disclosure relates to a method as hereinbefore defined wherein the compound of formula (I), (II), (III-A), or (III-B), a pharmaceutically acceptable salt, or a stereoisomer thereof is administered before, after or together with at least one other pharmacologically active substance.

In one embodiment, the present disclosure relates to a method as hereinbefore defined wherein the SOS1 inhibitor compound—or a pharmaceutically acceptable salt thereof—is administered in combination with a therapeutically effective amount of at least one other pharmacologically active substance.

In one embodiment, the present disclosure relates to a method as hereinbefore defined wherein the compound of formula (I), (II), (III-A), or (III-B), a pharmaceutically acceptable salt, or a stereoisomer thereof is administered in combination with a therapeutically effective amount of at least one other pharmacologically active substance.

In one embodiment, the present disclosure relates to a method for the treatment as hereinbefore defined.

In one embodiment, the disease/condition/cancer to be treated/prevented with the SOS1 inhibitor compound, SOS1 inhibitor compound for use, compound of formula (I), compound of formula (I) for use, use for preparing and method for the treatment and/or prevention as herein (above and below) defined is selected from the group consisting of pancreatic cancer, lung cancer, colorectal cancer, cholangiocarcinoma, multiple myeloma, melanoma, uterine cancer, endometrial cancer, thyroid cancer, acute myeloid leukaemia, bladder cancer, urothelial cancer, gastric cancer, cervical cancer, head and neck squamous cell carcinoma, diffuse large B cell lymphoma, oesophageal cancer, chronic lymphocytic leukaemia, hepatocellular cancer, breast cancer, ovarian cancer, prostate cancer, glioblastoma, renal cancer and sarcomas.

In one embodiment, the disease/condition/cancer to be treated/prevented with the SOS1 inhibitor compound, SOS1 inhibitor compound for use, compound of formula (I), compound of formula (I) for use, use for preparing and method for the treatment and/or prevention as herein (above and below) defined is selected from the group consisting of pancreatic cancer, lung cancer (preferably non-small cell lung cancer (NSCLC)), cholangiocarcinoma and colorectal cancer.

In one embodiment, the disease/condition to be treated/prevented with the SOS1 inhibitor compound, SOS1 inhibitor compound for use, compound of formula (I), compound of formula (I) for use, use for preparing and method for the treatment and/or prevention as herein (above and below) defined is a RASopathy. In one embodiment, it is selected from the group consisting of Neurofibromatosis type 1 (NF1), Noonan Syndrome (NS), Noonan Syndrome with Multiple Lentigines (NSML) (also referred to as LEOPARD syndrome), Capillary Malformation-Arteriovenous Malformation Syndrome (CM-AVM), Costello Syndrome (CS), Cardio-Facio-Cutaneous Syndrome (CFC), Legius Syndrome (also known as NF1-like Syndrome) and Hereditary gingival fibromatosis.

In one embodiment, the pharmacologically active substance to be used together/in combination with the SOS1 inhibitor compound, in particular compound of formula (I), (II), (III-A), or (III-B), a pharmaceutically acceptable salt, or a stereoisomer thereof, or in the medical uses, uses, methods of treatment and/or prevention as herein (above and below) defined can be selected from any one or more of the following:

1. an inhibitor of EGFR and/or of mutants thereof
    - a. e.g. afatinib, erlotinib, gefitinib, lapatinib, cetuximab, panitumumab, osimertinib, olmutinib, EGF-816;
    - b. afatinib, osimertinib and cetuximab; or
    - c. afatinib;
2. an inhibitor of ErbB2 (Her2) and/or of mutants thereof
    - a. e.g. afatinib, lapatinib, trastuzumab, pertuzumab;
    - b. afatinib and trastuzumab;
    - c. trastuzumab;
3. an inhibitor of ALK and/or of mutants thereof
    - a. e.g. crizotinib, alectinib, entrectinib, brigatinib;
    - b. crizotinib and alectinib;
    - c. crizotinib;
4. an inhibitor of MEK and/or of mutants thereof
    - a. e.g. trametinib, cobimetinib, binimetinib, selumetinib, refametinib;
    - b. trametinib and cobimetinib;
    - c. trametinib;
5. an inhibitor of GDP-bound KRAS and/or of mutants thereof
    - a. an irreversible inhibitor of KRAS G12C
        - i. e.g. ARS-853 (compound V-64 in WO 2014/152588), example I-272 in WO 2016/044772;
    - b. a reversible inhibitor of GDP-bound KRAS and/or of mutants thereof;
6. an inhibitor of BCR-ABL and/or of mutants thereof
    - a. e.g. imatinib, dasatinib, nilotinib;
    - b. imatinib and nilotinib;
    - c. imatinib;
7. an inhibitor of FGFR1 and/or FGFR2 and/or FGFR3 and/or of mutants thereof
    - a. e.g. nintedanib;
8. an inhibitor of ROS1 and/or of mutants thereof
    - a. e.g. crizotinib, entrectinib, lorlatinib, ceritinib, merestinib;
    - b. crizotinib and entrectinib;
    - c. crizotinib;
9. an inhibitor of c-MET and/or of mutants thereof
10. an inhibitor of AXL and/or of mutants thereof
11. an inhibitor of NTRK1 and/or of mutants thereof
12. an inhibitor of RET and/or of mutants thereof
13. a taxane
    - a. e.g. paclitaxel, nab-paclitaxel, docetaxel;
    - b. paclitaxel;
14. a platinum-containing compound
    - a. e.g. cisplatin, carboplatin, oxaliplatin;
15. an anf/-metabolite
    - a. e.g. 5-fluorouracil, capecitabine, floxuridine, cytarabine, gemcitabine, combination of trifluridine and tipiracil (=TAS102);
    - b. gemcitabine;
16. mitotic kinase inhibitor
    - a. e.g. CDK4/6 inhibitor
        - i. e.g. palbociclib, ribociclib, abemaciclib;
        - ii. palbociclib and abemaciclib;
        - iii. abemaciclib;
17. an immunotherapeutic agent
    - a. e.g. an immune checkpoint inhibitor
        - i. e.g. an anf/-CTLA4 mAb, anf/-PD1 mAb, anf/-PD-L1 mAb, anf/-PD-L2 mAb, anti-LAG3 mAb, anf/-TIM3 mAb;
        - ii. an anf/-PD1 mAb;
        - iii. e.g. ipilimumab, nivolumab, pembrolizumab, atezolizumab, avelumab, durvalumab, pidilizumab, PDR-001 (=spartalizumab);
        - iv. nivolumab, pembrolizumab and PDR-001 (=spartalizumab);
        - v. pembrolizumab;
18. an anti-angiogenic drug
    - a. e.g. bevacizumab, nintedanib;
    - b. bevacizumab;
19. a topoisomerase inhibitor
    - a. e.g. irinotecan, liposomal irinotecan, topotecan;
    - b. irinotecan;
20. an inhibitor of A-Raf and/or B-Raf and/or C-Raf and/or of mutants thereof
    - a. e.g. RAF-709 (=example 131 in WO 2014/151616), LY-3009120 (=example 1 in WO 2013/134243);
21. an inhibitor of ERK and/or of mutants thereof
    - a. e.g. ulixertinib;

22. an apoptose regulator
    a. e.g. an inhibitor of the interaction between p53 (functional p53, wt p53) and MDM2 (a "MDM2 inhibitor");
        i. e.g. HDM-201, NVP-CGM097, RG-7112, MK-8242, RG-7388, SAR405838, AMG-232, DS-3032, RG-7775, APG-1 15;
        ii. HDM-201, RG-7388 and AMG-232
    b. e.g. a PARP inhibitor;
    c. e.g. a MCL-1 inhibitor;
23. an inhibitor of mTOR
    a. e.g. rapamycin, temsirolimus, everolimus, ridaforolimus;
24. an epigenetic regulator
    a. e.g. a BET inhibitor
        i. e.g. JQ-1, GSK 525762, OTX 015 (=MK8628), CPI 0610, TEN-010 (=R06870810);
    b. e.g. a CDK9 inhibitor;
25. an inhibitor of IGF1/2 and/or of IGF1-R
    a. e.g. xentuzumab (antibody 60833 in WO 2010/066868), MEDI-573 (=dusigitumab);
26. an inhibitor of RAS GEFs and/or of mutants thereof
    a. e.g. an inhibitor of SOS2 and/or of mutants thereof
27. an inhibitor of PI3K and/or of mutants thereof.
28. an inhibitor of SHP2 and/or of mutants thereof.

In one embodiment, non-drug therapies can be used together/in combination with the SOS1 inhibitor compound, in particular compound of formula (I), (II), (III-A), or (III-B), a pharmaceutically acceptable salt, or a stereoisomer thereof, or in the medical uses, uses, methods of treatment and/or prevention as herein (above and below). Examples of non-drug treatments include, but are not limited to, radiation therapy, cryotherapy, hyperthermia, surgery (e.g., surgical excision of tumor tissue), and T cell adoptive transfer (ACT) therapy.

In one embodiment, the compounds of the present disclosure may be used as an adjuvant therapy after surgery. In some embodiments, the compounds of the present disclosure may be used as a neo-adjuvant therapy prior to surgery.

Radiation therapy may be used for inhibiting abnormal cell growth or treating a hyperproliferative disorder, such as cancer, in a subject (e.g., mammal (e.g., human)). Techniques for administering radiation therapy are known in the art. Radiation therapy can be administered through one of several methods, or a combination of methods, including, without limitation, external-beam therapy, internal radiation therapy, implant radiation, stereotactic radiosurgery, systemic radiation therapy, radiotherapy and permanent or temporary interstitial brachy therapy. The term "brachy therapy," as used herein, refers to radiation therapy delivered by a spatially confined radioactive material inserted into the body at or near a tumor or other proliferative tissue disease site. The term is intended, without limitation, to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present disclosure include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, or Y-90. Moreover, the radionuclide(s) can be embodied in a gel or radioactive micro spheres.

In one embodiment, the compounds of the present disclosure can render abnormal cells more sensitive to treatment with radiation for purposes of killing or inhibiting the growth of such cells. Accordingly, the present disclosure further relates to a method for sensitizing abnormal cells in a mammal to treatment with radiation which comprises administering to the mammal an amount of a compound of the present disclosure, which amount is effective to sensitize abnormal cells to treatment with radiation. The amount of the compound in this method can be determined according to the means for ascertaining effective amounts of such compounds described herein. In some embodiments, the compounds of the present disclosure may be used as an adjuvant therapy after radiation therapy or as a neo-adjuvant therapy prior to radiation therapy.

In one embodiment, the non-drug treatment is a T cell adoptive transfer (ACT) therapy. In some embodiments, the T cell is an activated T cell. The T cell may be modified to express a chimeric antigen receptor (CAR). CAR modified T (CAR-T) cells can be generated by any method known in the art. For example, the CAR-T cells can be generated by introducing a suitable expression vector encoding the CAR to a T cell. Prior to expansion and genetic modification of the T cells, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present disclosure, any number of T cell lines available in the art may be used. In some embodiments, the T cell is an autologous T cell. Whether prior to or after genetic modification of the T cells to express a desirable protein (e.g., a CAR), the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 7,572,631; 5,883,223; 6,905,874; 6,797,514; and 6,867,041.

In one embodiment, additional therapy agents can be used together/in combination with the SOS1 inhibitor compound, in particular compound of formula (I), (II), (III-A), or (III-B), a pharmaceutically acceptable salt, or a stereoisomer thereof, or in the medical uses, uses, methods of treatment and/or prevention as herein (above and below).

In one embodiment, the additional therapeutic agent may be a steroid. Accordingly, in some embodiments, the one or more additional therapies includes a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts or derivatives thereof.

Further examples of therapeutic agents that may be used in combination therapy with the compounds of the present disclosure include compounds described in the following patents: U.S. Pat. Nos. 6,258,812, 6,630,500, 6,515,004, 6,713,485, 5,521,184, 5,770,599, 5,747,498, 5,990,141, 6,235,764, and 8,623,885, and International Patent Applications WO01/37820, WO01/32651, WO02/68406, WO02/66470, WO02/55501, WO04/05279, WO04/07481, WO04/07458, WO04/09784, WO02/59110, WO99/45009, WO00/59509, WO99/61422, WO00/12089, and WO00/02871.

A therapeutic agent may be a biologic (e.g., cytokine (e.g., interferon or an interleukin such as IL-2)) used in treatment of cancer or symptoms associated therewith. In some embodiments, the biologic is an immunoglobulin-based biologic, e.g., a monoclonal antibody (e.g., a humanized antibody, a fully human antibody, an Fc fusion protein, or a functional fragment thereof) that agonizes a target to stimulate an anti-cancer response or antagonizes an antigen important for cancer. Also included are antibody-drug conjugates.

A therapeutic agent may be a checkpoint inhibitor. In one embodiment, the checkpoint inhibitor is an inhibitory antibody (e.g., a monospecific antibody such as a monoclonal antibody). The antibody may be, e.g., humanized or fully human. In some embodiments, the checkpoint inhibitor is a fusion protein, e.g., an Fc-receptor fusion protein. In some embodiments, the checkpoint inhibitor is an agent, such as an antibody, that interacts with a checkpoint protein. In some embodiments, the checkpoint inhibitor is an agent, such as an antibody, that interacts with the ligand of a checkpoint protein. In some embodiments, the checkpoint inhibitor is an inhibitor (e.g., an inhibitory antibody or small molecule inhibitor) of CTLA-4 (e.g., an anti-CTLA-4 antibody or fusion a protein). In some embodiments, the checkpoint inhibitor is an inhibitor or antagonist (e.g., an inhibitory antibody or small molecule inhibitor) of PD-1. In some embodiments, the checkpoint inhibitor is an inhibitor or antagonist (e.g., an inhibitory antibody or small molecule inhibitor) of PDL-1. In some embodiments, the checkpoint inhibitor is an inhibitor or antagonist (e.g., an inhibitory antibody or Fc fusion or small molecule inhibitor) of PDL-2 (e.g., a PDL-2/Ig fusion protein). In some embodiments, the checkpoint inhibitor is an inhibitor or antagonist (e.g., an inhibitory antibody or small molecule inhibitor) of B7-H3, B7-H4, BTLA, HVEM, TIM3, GAL9, LAG3, VISTA, KIR, 2B4, CD160, CGEN-15049, CHK 1, CHK2, A2aR, B-7 family ligands, or a combination thereof. In some embodiments, the checkpoint inhibitor is pembrolizumab, nivolumab, PDR001 (NVS), REGN2810 (Sanofi/Regeneron), a PD-L1 antibody such as, e.g., avelumab, durvalumab, atezolizumab, pidilizumab, JNJ-63723283 (JNJ), BGB-A317 (BeiGene & Celgene) or a checkpoint inhibitor disclosed in Preusser, M. et al. (2015) Nat. Rev. Neurol., including, without limitation, ipilimumab, tremelimumab, nivolumab, pembrolizumab, AMP224, AMP514/MEDIO680, BMS936559, MED14736, MPDL3280A, MSB0010718C, BMS986016, IMP321, lirilumab, IPH2101, 1-7F9, and KW-6002.

A therapeutic agent may be an agent that treats cancer or symptoms associated therewith (e.g., a cytotoxic agent, non-peptide small molecules, or other compound useful in the treatment of cancer or symptoms associated therewith, collectively, an "anti-cancer agent"). Anti-cancer agents can be, e.g., chemotherapeutics or targeted therapy agents.

Anti-cancer agents include mitotic inhibitors, intercalating antibiotics, growth factor inhibitors, cell cycle inhibitors, enzymes, topoisomerase inhibitors, biological response modifiers, alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Further anti-cancer agents include leucovorin (LV), irenotecan, oxaliplatin, capecitabine, paclitaxel, and doxetaxel. In some embodiments, the one or more additional therapies includes two or more anti-cancer agents. The two or more anti-cancer agents can be used in a cocktail to be administered in combination or administered separately. Suitable dosing regimens of combination anti-cancer agents are known in the art and described in, for example, Saltz et al., Proc. Am. Soc. Clin. Oncol. 18:233a (1999), and Douillard et al., Lancet 355(9209):1041-1047 (2000).

Other non-limiting examples of anti-cancer agents include Gleevec® (Imatinib Mesylate); Kyprolis® (carfilzomib); Velcade® (bortezomib); Casodex (bicalutamide); Iressa® (gefitinib); alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; sarcodictyin A; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, such as calicheamicin gammall and calicheamicin omegall (see, e.g., Agnew, Chem. Intl. Ed Engl. 33:183-186 (1994)); dynemicin such as dynemicin A; bisphosphonates such as clodronate; an esperamicin; neocarzinostatin chromophore and related chromoprotein enediyne antibiotic chromophores, aclacinomysins, actinomycin, authramycin, azaserine, bleomycins, cactinomycin, calicheamicin, carabicin, caminomycin, carminomycin, carzinophilin, chromomycins, dactinomycin, daunorubicin, detorubicin, 6-diazo-5-oxo-L-norleucine, adriamycin (doxorubicin), morpholino-doxorubicin, cyanomorpholino-doxorubicin, 2-pyrrolino-doxorubicin, deoxydoxorubicin, epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenishers such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone such as epothilone B; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes such as T-2 toxin, verracurin A, roridin A and anguidine; urethane; vindesine; dacarbazine; mannomustine; mitobronitol; mitolactol; pipobroman; gacytosine; arabinoside ("Ara-C"); cyclophosphamide; thiotepa; taxoids, e.g., Taxol® (paclitaxel), Abraxane® (cremophor-free, albumin-engineered nanoparticle formulation of paclitaxel), and Taxotere® (doxetaxel); chloranbucil; tamoxifen (Nolvadex™); raloxifene; aromatase inhibiting 4(5)-imidazoles; 4-hydroxytamoxifen; trioxifene; keoxifene; LY 117018; onapristone; toremifene (Fareston®); flutamide, nilutamide, bicalutamide, leuprolide, goserelin; chlorambucil; Gemzar® gemcitabine; 6-thioguanine; mercaptopurine; platinum coordination complexes such as cisplatin, oxaliplatin and carboplatin; vinblastine; platinum; etoposide (VP-16); ifosfamide; mitoxantrone; vincristine; Navelbine® (vinorelbine); novantrone; teniposide; edatrexate; daunomycin; aminopterin; ibandronate; irinotecan (e.g., CPT-11); topoisomerase inhibitor RFS 2000; difluoromethylornithine (DMFO); retinoids such as retinoic acid; esperamicins; capecitabine (e.g., Xeloda®); and pharmaceutically acceptable salts of any of the above.

Additional non-limiting examples of anti-cancer agents include trastuzumab (Herceptin®), bevacizumab (Avastin®), cetuximab (Erbitux®), rituximab (Rituxan®), Taxol®, Arimidex®, ABVD, avicine, abagovomab, acridine carboxamide, adecatumumab, 17-N-allylamino-17-demethoxygeldanamycin, alpharadin, alvocidib, 3-aminopyridine-2-carboxaldehyde thiosemicarbazone, amonafide, anthracenedione, anti-CD22 immunotoxins, antineoplastics (e.g., cell-cycle nonspecific antineoplastic agents, and other antineoplastics described herein), antitumorigenic herbs, apaziquone, atiprimod, azathioprine, belotecan, bendamustine, BIBW 2992, biricodar, brostallicin, bryostatin, buthionine sulfoximine, CBV (chemotherapy), calyculin, dichloroacetic acid, discodermolide, elsamitrucin, enocitabine, eribulin, exatecan, exisulind, ferruginol, forodesine, fosfestrol, ICE chemotherapy regimen, IT-101, imexon, imiquimod, indolocarbazole, irofulven, laniquidar, larotaxel, lenalidomide, lucanthone, lurtotecan, mafosfamide, mitozolomide, nafoxidine, nedaplatin, olaparib, ortataxel, PAC-1, pawpaw, pixantrone, proteasome inhibitors, rebeccamycin, resiquimod, rubitecan, SN-38, salinosporamide A, sapacitabine, Stanford V, swainsonine, talaporfin, tariquidar, tegafur-uracil, temodar, tesetaxel, triplatin tetranitrate, tris(2-chloroethyl)amine, troxacitabine, uramustine, vadimezan, vinflunine, ZD6126, and zosuquidar.

Further non-limiting examples of anti-cancer agents include natural products such as vinca alkaloids (e.g., vinblastine, vincristine, and vinorelbine), epidipodophyllotoxins (e.g., etoposide and teniposide), antibiotics (e.g., dactinomycin (actinomycin D), daunorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., a CDK 4/6 inhibitor such as ribociclib, abemaciclib, or palbociclib), seliciclib, UCN-01, P1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs, pyrimidine analogs (e.g., fluorouracil, floxuridine, and cytarabine), purine analogs and related inhibitors (e.g., mercaptopurine, thioguanine, pentostatin, and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTOR inhibitors (e.g., vistusertib, temsirolimus, everolimus, ridaforolimus, and sirolimus), KSP (Eg5) inhibitors (e.g., Array 520), DNA binding agents (e.g., Zalypsis®), PI3K inhibitors such as PI3K delta inhibitor (e.g., GS-1101 and TGR-1202), PI3K delta and gamma inhibitor (e.g., CAL-130), copanlisib, alpelisib and idelalisib; multi-kinase inhibitor (e.g., TG02 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., LY2127399), IKK inhibitors, p38MAPK inhibitors, anti-IL-6 (e.g., CNT0328), telomerase inhibitors (e.g., GRN 163L), aurora kinase inhibitors (e.g., MLN8237), cell surface monoclonal antibodies (e.g., anti-CD38 (HUMAX-CD38), anti-CS1 (e.g., elotuzumab), HSP90 inhibitors (e.g., 17 AAG and KOS 953), P13K/Akt inhibitors (e.g., perifosine), Akt inhibitors (e.g., GSK-2141795), PKC inhibitors (e.g., enzastaurin), FTIs (e.g., Zarnestra™), anti-CD138 (e.g., BT062), Torcl/2 specific kinase inhibitors (e.g., INK128), ER/UPR targeting agents (e.g., MKC-3946), cFMS inhibitors (e.g., ARRY-382), JAK1/2 inhibitors (e.g., CYT387), PARP inhibitors (e.g., olaparib and veliparib (ABT-888)), and BCL-2 antagonists.

In some embodiments, an anti-cancer agent is selected from mechlorethamine, camptothecin, ifosfamide, tamoxifen, raloxifene, gemcitabine, Navelbine®, sorafenib, or any analog or derivative variant of the foregoing.

In some embodiments, an anti-cancer agent is an ALK inhibitor. Non-limiting examples of ALK inhibitors include ceritinib, TAE-684 (NVP-TAE694), PF02341066 (crizotinib or 1066), alectinib; brigatinib; entrectinib; ensartinib (X-396); lorlatinib; ASP3026; CEP-37440; 4SC-203; TL-398; PLB1003; TSR-011; CT-707; TPX-0005, and AP26113. Additional examples of ALK kinase inhibitors are described in examples 3-39 of WO05016894.

In some embodiments, an anti-cancer agent is an inhibitor of a member downstream of a Receptor Tyrosine Kinase (RTK)/Growth Factor Receptor (e.g., a SHP2 inhibitor (e.g., SHP099, TNO155, RMC-4550, RMC-4630, JAB-3068), another SOS1 inhibitor (e.g., BI-1701963), a Raf inhibitor, a MEK inhibitor, an ERK inhibitor, a PI3K inhibitor, a PTEN inhibitor, an AKT inhibitor, or an mTOR inhibitor (e.g., mTORC1 inhibitor or mTORC2 inhibitor). In some embodiments, the anti-cancer agent is JAB-3312. In some embodiments, an anti-cancer agent is a Ras inhibitor (e.g., AMG 510, MRTX1257, LY349946, MRTX849, ARS-3248 (JNJ-74699157), or ARS-1620), or a Ras vaccine, or another therapeutic modality designed to directly or indirectly decrease the oncogenic activity of Ras.

In some embodiments, the Ras protein is wild-type. In some embodiments, the cancer comprises a Ras mutation. In some embodiments, a mutation is selected from:

(a) the following K-Ras mutants: G12D, G12V, G12C, G13D, G12R, G12A, Q61H, G12S, A146T, G13C, Q61L, Q61R, K117N, A146V, G12F, Q61K, L19F, Q22K, V14I, A59T, A146P, G13R, G12L, or G13V, and combinations thereof;

(b) the following H-Ras mutants: Q61R, G13R, Q61K, G12S, Q61L, G12D,
G13V, G13D, G12C, K117N, A59T, G12V, G13C, Q61H, G13S, A18V, D119N, G13N, A146T, A66T, G12A, A146V, G12N, or G12R, and combinations thereof; and (c) the following N-Ras mutants: Q61R, Q61K, G12D, Q61L, Q61H, G13R,
G13D, G12S, G12C, G12V, G12A, G13V, G12R, P185S, G13C, A146T, G60E, Q61P, A59D, E132K, E49K, T50I, A146V, or A59T, and combinations thereof; or a combination of any of the foregoing (e.g., both K-Ras G12C and K-Ras G13C). In some embodiments, the cancer comprises a Ras mutation selected from the group consisting of G12C, G13C, G12A, G12D, G13D, G12S, G13S, G12V and G13V.

In some embodiments, a therapeutic agent that may be combined with a compound of the present disclosure is an inhibitor of the MAP kinase (MAPK) pathway (or "MAPK inhibitor"). MAPK inhibitors include, but are not limited to, one or more MAPK inhibitor described in Cancers (Basel) 2015 September; 7(3): 1758-1784. For example, the MAPK inhibitor may be selected from one or more of trametinib, binimetinib, selumetinib, cobimetinib, LErafAON (NeoPharm), ISIS 5132; vemurafenib, pimasertib, TAK733, R04987655 (CH4987655); CI-1040; PD-0325901; CH5126766; MAP855; AZD6244; refametinib (RDEA 119/BAY 86-9766); GDC-0973/XL581; AZD8330 (ARRY-424704/ARRY-704); RO5126766 (Roche, described in PLoS One. 2014 Nov. 25; 9(11)); and GSK1120212 (or JTP-74057, described in Clin Cancer Res. 2011 Mar. 1; 17(5):989-1000).

In some embodiments, an anti-cancer agent is a disrupter or inhibitor of the RAS-RAF-ERK or PI3K-AKT-TOR or PI3K-AKT signaling pathways. The PI3K/AKT inhibitor may include, but is not limited to, one or more PI3K/AKT inhibitor described in Cancers (Basel) 2015 September; 7(3): 1758-1784. For example, the PI3K/AKT inhibitor may be selected from one or more of NVP-BEZ235; BGT226; XL765/SAR245409; SF1126; GDC-0980; PI-103; PF-04691502; PKI-587; GSK2126458.

In some embodiments, an anti-cancer agent is a PD-1 or PD-L1 antagonist.

In some embodiments, additional therapeutic agents include EGFR inhibitors, IGF-1R inhibitors, MEK inhibitors, PI3K inhibitors, AKT inhibitors, TOR inhibitors, MCL-1 inhibitors, BCL-2 inhibitors, SHP2 inhibitors, proteasome inhibitors, and immune therapies.

IGF-1R inhibitors include linsitinib, or a pharmaceutically acceptable salt thereof.

EGFR inhibitors include, but are not limited to, small molecule antagonists, antibody inhibitors, or specific antisense nucleotide or siRNA. Useful antibody inhibitors of EGFR include cetuximab (Erbitux®), panitumumab (Vectibix®), zalutumumab, nimotuzumab, and matuzumab. Further antibody-based EGFR inhibitors include any anti-EGFR antibody or antibody fragment that can partially or completely block EGFR activation by its natural ligand. Non-limiting examples of antibody-based EGFR inhibitors include those described in Modjtahedi et al., Br. J. Cancer 1993, 67:247-253; Teramoto et al., Cancer 1996, 77:639-645; Goldstein et al., Clin. Cancer Res. 1995, 1:1311-1318; Huang et al., 1999, Cancer Res. 15:59(8):1935-40; and Yang et al., Cancer Res. 1999, 59:1236-1243. The EGFR inhibitor can be monoclonal antibody Mab E7.6.3 (Yang, 1999 supra), or Mab C225 (ATCC Accession No. HB-8508), or an antibody or antibody fragment having the binding specificity thereof.

Small molecule antagonists of EGFR include gefitinib (Iressa®), erlotinib (Tarceva®), and lapatinib (TykerB®). See, e.g., Yan et al., Pharmacogenetics and Pharmacogenomics In Oncology Therapeutic Antibody Development, BioTechniques 2005, 39(4):565-8; and Paez et al., EGFR Mutations In Lung Cancer Correlation With Clinical Response To Gefitinib Therapy, Science 2004, 304(5676):1497-500. Further non-limiting examples of small molecule EGFR inhibitors include any of the EGFR inhibitors described in the following patent publications, and all pharmaceutically acceptable salts of such EGFR inhibitors: EP 0520722; EP 0566226; WO96/33980; U.S. Pat. No. 5,747,498; WO96/30347; EP 0787772; WO97/30034; WO97/30044; WO97/38994; WO97/49688; EP 837063; WO98/02434; WO97/38983; WO95/19774; WO95/19970; WO97/13771; WO98/02437; WO98/02438; WO97/32881; DE 19629652; WO98/33798; WO97/32880; WO97/32880; EP 682027; WO97/02266; WO97/27199; WO98/07726; WO97/34895; WO96/31510; WO98/14449; WO98/14450; WO98/14451; WO95/09847; WO97/19065; WO98/17662; U.S. Pat. Nos. 5,789,427; 5,650,415; 5,656,643; WO99/35146; WO99/35132; WO99/07701; and WO92/20642. Additional non-limiting examples of small molecule EGFR inhibitors include any of the EGFR inhibitors described in Traxler et al., Exp. Opin. Ther. Patents 1998, 8(12):1599-1625. In some embodiments, an EGFR inhibitor is osimertinib.

MEK inhibitors include, but are not limited to, pimasertib, selumetinib, cobimetinib (Cotellic®), trametinib (Mekinist®), and binimetinib (Mektovi®). In some embodiments, a MEK inhibitor targets a MEK mutation that is a Class I MEK1 mutation selected from D67N; P124L; P124S; and L177V. In some embodiments, the MEK mutation is a Class II MEK1 mutation selected from DE51-Q58; DF53-Q58; E203K; L177M; C121S; F53L; K57E; Q56P; and K57N.

PI3K inhibitors include, but are not limited to, wortmannin; 17-hydroxywortmannin analogs described in WO06/044453; 4-[2-(1H-Indazol-4-yl)-6-[[4-(methylsulfonyl)piperazin-1-yl]methyl]thieno[3,2-d]pyrimidin-4-yl]morpholine (also known as pictilisib or GDC-0941 and described in WO09/036082 and WO09/055730); 2-methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in WO06/122806); (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one (described in WO08/070740); LY294002 (2-(4-morpholinyl)-8-phenyl-4H-1-benzopyran-4-one (available from Axon Medchem); PI 103 hydrochloride (3-[4-(4-morpholinylpyrido-[3',2':4,5]furo[3,2-d]pyrimidin-2-yl] phenol hydrochloride (available from Axon Medchem); PIK 75 (2-methyl-5-nitro-2-[(6-bromoimidazo [1,2-a]pyridin-3-yl)methylene]-1-methylhydrazide-benzenesulfonic acid, monohydrochloride) (available from Axon Medchem); PIK 90 (N-(7,8-dimethoxy-2,3-dihydro-imidazo [1,2-c]quinazolin-5-yl)-nicotinamide (available from Axon Medchem); AS-252424 (5-[1-[5-(4-fluoro-2-hydroxy-phenyl)-furan-2-yl]-meth-(Z)-ylidene]-thiazolidine-2,4-dione (available from Axon Medchem); TGX-221 (7-methyl-2-(4-morpholinyl)-9-[1-(phenylamino)ethyl]-4H-pyrido-[1,2-a] pyrimidin-4-one (available from Axon Medchem); XL-765; and XL-147. Other PI3K inhibitors include demethoxyviridin, perifosine, CAL101, PX-866, BEZ235, SF1126, INK1117, IPI-145, BKM120, XL147, XL765, Palomid 529, GSK1059615, ZSTK474, PWT33597, IC87114, TGI 00-115, CAL263, PI-103, GNE-477, CUDC-907, and AEZS-136.

AKT inhibitors include, but are not limited to, Akt-1-1 (inhibits Akt1) (Barnett et al., Biochem. J. 2005, 385(Pt. 2): 399-408); Akt-1-1,2 (inhibits Ak1 and 2) (Barnett et al., Biochem. J. 2005, 385(Pt. 2): 399-408); API-59CJ-Ome (e.g., Jin et al., Br. J. Cancer 2004, 91:1808-12); 1-H-imidazo[4,5-c]pyridinyl compounds (e.g., WO 05/011700); indole-3-carbinol and derivatives thereof (e.g., U.S. Pat. No. 6,656,963; Sarkar and Li J Nutr. 2004, 134(12 Suppl): 3493S-3498S); perifosine (e.g., interferes with Akt membrane localization; Dasmahapatra et al. Clin. Cancer Res. 2004, 10(15):5242-52); phosphatidylinositol ether lipid analogues (e.g., Gills and Dennis Expert. Opin. Investig. Drugs 2004, 13:787-97); and triciribine (TCN or API-2 or NCI identifier: NSC 154020; Yang et al., Cancer Res. 2004, 64:4394-9).

mTOR inhibitors include, but are not limited to, ATP-competitive mTORC1/mTORC2 inhibitors, e.g., PI-103, PP242, PP30; Torin 1; FKBP12 enhancers; 4H-1-benzopyran-4-one derivatives; and rapamycin (also known as sirolimus) and derivatives thereof, including: temsirolimus (Torisel®); everolimus (Afinitor®; WO94/09010); ridaforolimus (also known as deforolimus or AP23573); rapalogs, e.g., as disclosed in WO98/02441 and WO01/14387, e.g., AP23464 and AP23841; 40-(2-hydroxyethyl) rapamycin; 40-[3-hydroxy(hydroxymethyl)methylpropanoate]-rapamycin (also known as CC1779); 40-epi-(tetrazolyt)-rapamycin (also called ABT578); 32-deoxorapamycin; 16-pentynyloxy-32(S)-dihydrorapanycin; derivatives disclosed in WO05/005434; derivatives disclosed in U.S. Pat. Nos. 5,258,389, 5,118,677, 5,118,678, 5,100,883, 5,151,413, 5,120,842, and 5,256,790, and in WO94/090101, WO92/05179, WO93/111130, WO94/02136, WO94/02485, WO95/14023, WO94/02136, WO95/16691, WO96/41807, WO96/41807, and WO2018204416; and phosphorus-containing rapamycin derivatives (e.g., WO05/016252). In some embodiments, the mTOR inhibitor is a bisteric inhibitor (see, e.g., WO2018204416, WO2019212990 and WO2019212991), such as RMC-5552.

BRAF inhibitors that may be used in combination with compounds of the present disclosure include, for example, vemurafenib, dabrafenib, and encorafenib. A BRAF may comprise a Class 3 BRAF mutation. In some embodiments, the Class 3 BRAF mutation is selected from one or more of the following amino acid substitutions in human BRAF: D287H; P367R; V459L; G466V; G466E; G466A; S467L; G469E; N581S; N581I; D594N; D594G; D594A; D594H; F595L; G596D; G596R and A762E.

MCL-1 inhibitors include, but are not limited to, AMG-176, MIK665, and S63845. The myeloid cell leukemia-1 (MCL-1) protein is one of the key anti-apoptotic members of the B-cell lymphoma-2 (BCL-2) protein family. Over-expression of MCL-1 has been closely related to tumor progression as well as to resistance, not only to traditional chemotherapies but also to targeted therapeutics including BCL-2 inhibitors such as ABT-263.

In some embodiments, the additional therapeutic agent is a SHP2 inhibitor. SHP2 is a non-receptor protein tyrosine phosphatase encoded by the PTPN11 gene that contributes to multiple cellular functions including proliferation, differentiation, cell cycle maintenance and migration. SHP2 has two N-terminal Src homology 2 domains (N—SH2 and C—SH2), a catalytic domain (PTP), and a C-terminal tail. The two SH2 domains control the subcellular localization and functional regulation of SHP2. The molecule exists in an inactive, self-inhibited conformation stabilized by a binding network involving residues from both the N—SH2 and PTP domains. Stimulation by, for example, cytokines or growth factors acting through receptor tyrosine kinases (RTKs) leads to exposure of the catalytic site resulting in enzymatic activation of SHP2.

SHP2 is involved in signaling through the RAS-mitogen-activated protein kinase (MAPK), the JAK-STAT or the phosphoinositol 3-kinase-AKT pathways. Mutations in the PTPN11 gene and subsequently in SHP2 have been identified in several human developmental diseases, such as Noonan Syndrome and Leopard Syndrome, as well as human cancers, such as juvenile myelomonocytic leukemia, neuroblastoma, melanoma, acute myeloid leukemia and cancers of the breast, lung and colon. Some of these mutations destabilize the auto-inhibited conformation of SHP2 and promote autoactivation or enhanced growth factor driven activation of SHP2. SHP2, therefore, represents a highly attractive target for the development of novel therapies for the treatment of various diseases including cancer. A SHP2 inhibitor (e.g., RMC-4550 or SHP099) in combination with a RAS pathway inhibitor (e.g., a MEK inhibitor) have been shown to inhibit the proliferation of multiple cancer cell lines in vitro (e.g., pancreas, lung, ovarian and breast cancer). Thus, combination therapy involving a SHP2 inhibitor with a RAS pathway inhibitor could be a general strategy for preventing tumor resistance in a wide range of malignancies, and may form the basis of a triple combination inhibitor with a SOS1 inhibitor.

Non-limiting examples of such SHP2 inhibitors that are known in the art, include: Chen et al. Mol Pharmacol. 2006, 70, 562; Sarver et al., J. Med. Chem. 2017, 62, 1793; Xie et al., J. Med. Chem. 2017, 60, 113734; and Igbe et al., Oncotarget, 2017, 8, 113734; and PCT applications: WO2015107493; WO2015107494; WO201507495; WO2016203404; WO2016203405; WO2016203406; WO2011022440; WO2017156397; WO2017079723; WO2017211303; WO2012041524; WO2017211303; WO2019051084; WO2017211303; US20160030594; US20110281942; WO2010011666; WO2014113584; WO2014176488; WO2017100279; WO2019051469; U.S. Pat. No. 8,637,684; WO2007117699; WO2015003094; WO2005094314; WO2008124815; WO2009049098; WO2009135000; WO2016191328; WO2016196591; WO2017078499; WO2017210134; WO2018013597; WO2018129402; WO2018130928; WO20181309928; WO2018136264; WO2018136265; WO2018160731; WO2018172984; and WO2010121212, each of which is incorporated herein by reference.

In some embodiments, a SHP2 inhibitor binds in the active site. In some embodiments, a SHP2 inhibitor is a mixed-type irreversible inhibitor. In some embodiments, a SHP2 inhibitor binds an allosteric site e.g., a non-covalent allosteric inhibitor. In some embodiments, a SHP2 inhibitor is a covalent SHP2 inhibitor, such as an inhibitor that targets the cysteine residue (C333) that lies outside the phosphatase's active site. In some embodiments a SHP2 inhibitor is a reversible inhibitor. In some embodiments, a SHP2 inhibitor is an irreversible inhibitor. In some embodiments, the SHP2 inhibitor is SHP099. In some embodiments, the SHP2 inhibitor is TNO155. In some embodiments, the SHP2 inhibitor is RMC-4550. In some embodiments, the SHP2 inhibitor is RCM-4630. In some embodiments, the SHP2 inhibitor is JAB-3068.

Proteasome inhibitors include, but are not limited to, carfilzomib (Kyprolis®), bortezomib (Velcade®), and oprozomib.

Immune therapies include, but are not limited to, monoclonal antibodies, immunomodulatory imides (IMiDs), GITR agonists, genetically engineered T-cells (e.g., CAR-T cells), bispecific antibodies (e.g., BiTEs), and anti-PD-1, anti-PDL-1, anti-CTLA4, anti-LAG1, and anti-OX40 agents).

Immunomodulatory agents (IMiDs) are a class of immunomodulatory drugs (drugs that adjust immune responses) containing an imide group. The IMiD class includes thalidomide and its analogues (lenalidomide, pomalidomide, and apremilast).

Exemplary anti-PD-1 antibodies and methods for their use are described by Goldberg et al., Blood 2007, 110(1):186-192; Thompson et al., Clin. Cancer Res. 2007, 13(6):1757-1761; and WO06/121168 A1), as well as described elsewhere herein.

GITR agonists include, but are not limited to, GITR fusion proteins and anti-GITR antibodies (e.g., bivalent anti-GITR antibodies), such as, a GITR fusion protein described in U.S. Pat. Nos. 6,111,090, 8,586,023, WO2010/003118 and WO2011/090754; or an anti-GITR antibody described, e.g., in U.S. Pat. No. 7,025,962, EP 1947183, U.S. Pat. Nos. 7,812,135, 8,388,967, 8,591,886, 7,618,632, EP 1866339, and WO2011/028683, WO2013/039954, WO05/007190, WO07/133822, WO05/055808, WO99/40196, WO01/03720, WO99/20758, WO06/083289, WO05/115451, and WO2011/051726.

Another example of a therapeutic agent that may be used in combination with the compounds of the present disclosure is an anti-angiogenic agent. Anti-angiogenic agents are inclusive of, but not limited to, in vitro synthetically prepared chemical compositions, antibodies, antigen binding regions, radionuclides, and combinations and conjugates thereof. An anti-angiogenic agent can be an agonist, antagonist, allosteric modulator, toxin or, more generally, may act to inhibit or stimulate its target (e.g., receptor or enzyme activation or inhibition), and thereby promote cell death or arrest cell growth. In some embodiments, the one or more additional therapies include an anti-angiogenic agent.

Anti-angiogenic agents can be MMP-2 (matrix-metalloproteinase 2) inhibitors, MMP-9 (matrix-metalloprotienase 9) inhibitors, and COX-II (cyclooxygenase 11) inhibitors. Non-limiting examples of anti-angiogenic agents include rapamycin, temsirolimus (CCI-779), everolimus (RAD001), sorafenib, sunitinib, and bevacizumab. Examples of useful COX-II inhibitors include alecoxib, valdecoxib, and rofecoxib. Examples of useful matrix metalloproteinase inhibitors are described in WO96/33172, WO96/27583, WO98/07697, WO98/03516, WO98/34918, WO98/34915, WO98/33768, WO98/30566, WO90/05719, WO99/52910, WO99/52889, WO99/29667, WO99007675, EP0606046, EP0780386, EP1786785, EP1181017, EP0818442, EP1004578, and US20090012085, and U.S. Pat. Nos. 5,863,949 and 5,861,510. In some embodiments, MMP-2 and MMP-9 inhibitors are those that have little or no activity inhibiting MMP-1. In some embodiments, MMP-2 and MMP-9 inhibitors are those that selectively inhibit MMP-2 or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors are AG-3340, RO 32-3555, and RS 13-0830.

Further exemplary anti-angiogenic agents include KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as Vectibix® (panitumumab), erlotinib (Tarceva®), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). Other anti-angiogenic agents include Campath, IL-8, B-FGF, Tek antagonists (US2003/0162712; U.S. Pat. No. 6,413,932), anti-TWEAK agents (e.g., specifically binding antibodies or antigen binding regions, or soluble TWEAK receptor antagonists; see U.S. Pat. No. 6,727,225), ADAM distintegrin domain to antagonize the binding of integrin to its ligands (US 2002/0042368), specifically binding anti-eph receptor or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto). Additional anti-angiogenic agents include: SD-7784 (Pfizer, USA); cilengitide (Merck KGaA, Germany, EPO 0770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol (EntreMed, USA); TLC ELL-12 (Elan, Ireland); anecortave acetate (Alcon, USA); alpha-D148 Mab (Amgen, USA); CEP-7055 (Cephalon, USA); anti-Vn Mab (Crucell, Netherlands), DACantiangiogenic (ConjuChem, Canada); Angiocidin (InKine Pharmaceutical, USA); KM-2550 (Kyowa Hakko, Japan); SU-0879 (Pfizer, USA); CGP-79787 (Novartis, Switzerland, EP 0970070); ARGENT technology (Ariad, USA); YIGSR-Stealth (Johnson & Johnson, USA); fibrinogen-E fragment (BioActa, UK); angiogenic inhibitor (Trigen, UK); TBC-1635 (Encysive Pharmaceuticals, USA); SC-236 (Pfizer, USA); ABT-567 (Abbott, USA); Metastatin (EntreMed, USA); maspin (Sosei, Japan); 2-methoxyestradiol (Oncology Sciences Corporation, USA); ER-68203-00 (IV AX, USA); BeneFin (Lane Labs, USA); Tz-93 (Tsumura, Japan); TAN-1120 (Takeda, Japan); FR-111142 (Fujisawa, Japan, JP 02233610); platelet factor 4 (RepliGen, USA, EP 407122); vascular endothelial growth factor antagonist (Borean, Denmark); bevacizumab (pINN) (Genentech, USA); angiogenic inhibitors (SUGEN, USA); XL 784 (Exelixis, USA); XL 647 (Exelixis, USA); MAb, alpha5beta3 integrin, second generation (Applied Molecular Evolution, USA and MedImmune, USA); enzastaurin hydrochloride (Lilly, USA); CEP 7055 (Cephalon, USA and Sanofi-Synthelabo, France); BC 1 (Genoa Institute of Cancer Research, Italy); rBPI 21 and BPI-derived antiangiogenic (XOMA, USA); PI 88 (Progen, Australia); cilengitide (Merck KGaA, German; Munich Technical University, Germany, Scripps Clinic and Research Foundation, USA); AVE 8062 (Ajinomoto, Japan); AS 1404 (Cancer Research Laboratory, New Zealand); SG 292, (Telios, USA); Endostatin (Boston Childrens Hospital, USA); ATN 161 (Attenuon, USA); 2-methoxyestradiol (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProIX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenic, (EntreMed, USA); urokinase plasminogen activator inhibitor, (Dendreon, USA); oglufanide (pINN), (Melmotte, USA); HIF-lalfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol; anginex (Maastricht University, Netherlands, and Minnesota University, USA); ABT 510 (Abbott, USA); AAL 993 (Novartis, Switzerland); VEGI (ProteomTech, USA); tumor necrosis factor-alpha inhibitors; SU 11248 (Pfizer, USA and SUGEN USA); ABT 518, (Abbott, USA); YH16 (Yantai Rongchang, China); S-3APG (Boston Childrens Hospital, USA and EntreMed, USA); MAb, KDR (ImClone Systems, USA); MAb, alpha5 beta (Protein Design, USA); KDR kinase inhibitor (Celltech Group, UK, and Johnson & Johnson, USA); GFB 116 (South Florida University, USA and Yale University, USA); CS 706 (Sankyo, Japan); combretastatin A4 prodrug (Arizona State University, USA); chondroitinase AC (IBEX, Canada); BAY RES 2690 (Bayer, Germany); AGM 1470 (Harvard University, USA, Takeda, Japan, and TAP, USA); AG 13925 (Agouron, USA); Tetrathiomolybdate (University of Michigan, USA); GCS 100 (Wayne State University, USA) CV 247 (Ivy Medical, UK); CKD 732 (Chong Kun Dang, South Korea); irsogladine, (Nippon Shinyaku, Japan); RG 13577 (Aventis, France); WX 360 (Wilex, Germany); squalamine, (Genaera, USA); RPI 4610 (Sirna, USA); heparanase inhibitors (InSight, Israel); KL 3106 (Kolon, South Korea); Honokiol (Emory University, USA); ZK CDK (Schering AG, Germany); ZK Angio (Schering AG, Germany); ZK 229561 (Novartis, Switzerland, and Schering AG, Germany); XMP 300 (XOMA, USA); VGA 1102 (Taisho, Japan); VE-cadherin-2 antagonists (ImClone Systems, USA); Vasostatin (National Institutes of Health, USA); Flk-1 (ImClone Systems, USA); TZ 93 (Tsumura, Japan); TumStatin (Beth Israel Hospital, USA); truncated soluble FLT 1 (vascular endothelial growth factor receptor 1) (Merck & Co, USA); Tie-2 ligands (Regeneron, USA); and thrombospondin 1 inhibitor (Allegheny Health, Education and Research Foundation, USA).

Further examples of therapeutic agents that may be used in combination with the compounds of the present disclosure include agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor, c-Met.

Another example of a therapeutic agent that may be used in combination with the compounds of the present disclosure is an autophagy inhibitor. Autophagy inhibitors include, but are not limited to chloroquine, 3-methyladenine, hydroxychloroquine (Plaquenil™) bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used. In some embodiments, the one or more additional therapies include an autophagy inhibitor.

Another example of a therapeutic agent that may be used in combination with compounds of the present disclosure is an anti-neoplastic agent. In some embodiments, the one or more additional therapies include an anti-neoplastic agent. Non-limiting examples of anti-neoplastic agents include acemannan, aclarubicin, aldesleukin, alemtuzumab, alitretinoin, altretamine, amifostine, aminolevulinic acid, amrubicin, amsacrine, anagrelide, anastrozole, ancer, ancestim, arglabin, arsenic trioxide, BAM-002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburiembodiment, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, virulizin, zinostatin stimalamer, or zoledronic acid; abarelix; AE 941 (Aeterna), ambamustine, antisense oligonucleotide, bcl-2 (Genta), APC 8015 (Dendreon), decitabine, dexaminoglutethimide, diaziquone, EL 532 (Elan), EM 800 (Endorecherche), eniluracil, etanidazole, fenretinide, filgrastim SDO1 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techni clone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Additional examples of therapeutic agents that may be used in combination with compounds of the present disclosure include ipilimumab (Yervoy®); tremelimumab; galiximab; nivolumab, also known as BMS-936558 (Opdivo®); pembrolizumab (Keytruda®); avelumab (Bavencio®); AMP224; BMS-936559; MPDL3280A, also known as RG7446; MEDI-570; AMG557; MGA271; IMP321; BMS-663513; PF-05082566; CDX-1127; anti-OX40 (Providence Health Services); huMAbOX40L; atacicept; CP-870893; lucatumumab; dacetuzumab; muromonab-CD3; ipilumumab; MEDI4736 (Imfinzi®); MSB0010718C; AMP 224; adalimumab (Humira®); ado-trastuzumab emtansine (Kadcyla®); aflibercept (Eylea®); alemtuzumab (Campath®); basiliximab (Simulect®); belimumab (Benlysta®); basiliximab (Simulect®); belimumab (Benlysta®); brentuximab vedotin (Adcetris®); canakinumab (Ilaris®); certolizumab pegol (Cimzia®); daclizumab (Zenapax®); daratumumab (Darzalex®); denosumab (Prolia®); eculizumab (Soliris®); efalizumab (Raptiva®); gemtuzumab ozogamicin (Mylotarg®); golimumab (Simponi®); ibritumomab tiuxetan (Zevalin®); infliximab (Remicade®); motavizumab (Numax®); natalizumab (Tysabri®); obinutuzumab (Gazyva®); ofatumumab (Arzerra®); omalizumab (Xolair®); palivizumab (Synagis®); pertuzumab (Perjeta®); pertuzumab (Perjeta®); ranibizumab (Lucentis®); raxibacumab (Abthrax®); tocilizumab (Actemra®); tositumomab; tositumomab-i-131; tositumomab and tositumomab-i-131 (Bexxar®); ustekinumab (Stelara®); AMG 102; AMG 386; AMG 479; AMG 655; AMG 706; AMG 745; and AMG 951.

In some embodiments, an additional compound used in combination therapy with a compound of the present disclosure is selected from the group consisting of a CDK4/6 inhibitor (e.g., abemaciclib, palbociclib, or ribociclib), a KRAS:GDP G12C inhibitor (e.g., AMG 510, MRTX 1257) or other mutant Ras:GDP inhibitor, a KRAS:GTP G12C inhibitor or other mutant Ras:GTP inhibitor, a MEK inhibitor (e.g., refametinib, selumetinib, trametinib, or cobimetinib), a SHP2 inhibitor (e.g., TNO155, RMC-4630), an ERK inhibitor, and an RTK inhibitor (e.g., an EGFR inhibitor).

In some embodiments, an additional compound used in combination therapy with a compound of the present disclosure is selected from the group consisting of ABT-737, AT-7519, carfilzomib, cobimetinib, danusertib, dasatinib, doxorubicin, GSK-343, JQ1, MLN-7243, NVP-ADW742, paclitaxel, palbociclib and volasertib. In some embodiments, an additional compound used in combination therapy with a compound of the present disclosure is selected from the group consisting of neratinib, acetinib and reversine.

The compounds described herein can be used in combination with the agents disclosed herein or other suitable agents, depending on the condition being treated. Hence, in some embodiments the one or more compounds of the disclosure will be co-administered with other therapies as described herein. When used in combination therapy, the compounds described herein may be administered with the second agent simultaneously or separately. This administration in combination can include simultaneous administration of the two agents in the same dosage form, simultaneous administration in separate dosage forms, and separate administration. That is, a compound described herein and any of the agents described herein can be formulated together in the same dosage form and administered simultaneously. Alternatively, a compound of the present disclosure and any of the therapies described herein can be simultaneously administered, wherein both the agents are present in separate formulations. In another alternative, a compound of the present disclosure can be administered and followed by any of the therapies described herein, or vice versa. In some embodiments of the separate administration protocol, a compound of the present disclosure and any of the therapies described herein are administered a few minutes apart, or a few hours apart, or a few days apart.

In some embodiments, a combination therapeutic regimen employs two therapeutic agents, one compound of the present disclosure and a second selected from the therapeutic agents described herein. In some embodiments, a combination therapeutic regimen employs three therapeutic agents, one compound of the present disclosure and two selected from the therapeutic agents described herein. In some embodiments, a combination therapeutic regimen employs four or more therapeutic agents, one compound of the present disclosure and three selected from the therapeutic agents described herein.

In some embodiments of any of the methods described herein, the first therapy (e.g., a compound of the disclosure) and one or more additional therapies are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours, up to 24 hours, or up to 1-7, 1-14, 1-21 or 1-30 days before or after the one or more additional therapies.

In this section, all references are incorporated by reference for the agents described, whether explicitly stated as such or not.

6. Kits

Another aspect of the present disclosure provides kits comprising the compound of any one of the formulae described above or pharmaceutical compositions comprising the compound of any one of the formulae described above of the present disclosure. A kit may include, in addition to the compound of any one of the formulae described above, of the present disclosure or pharmaceutical composition thereof, diagnostic or therapeutic agents.

A kit may also include instructions for use in a diagnostic or therapeutic method. In some embodiments, the kit includes the compound of any one of the formulae described above, or a pharmaceutical composition thereof and a diagnostic agent. In other embodiments, the kit includes the compound of any one of the formulae described above, or a pharmaceutical composition thereof.

In yet another embodiment, the present disclosure comprises kits that are suitable for use in performing the methods of treatment described herein. In one embodiment, the kit contains a first dosage form comprising one or more of the compounds of the present disclosure in quantities sufficient to carry out the methods of the present disclosure. In another embodiment, the kit comprises one or more compounds of the present disclosure in quantities sufficient to carry out the methods of the present disclosure and a container for the dosage and a container for the dosage.

7. Preparation

The compounds of any one of the formulae described above, may be prepared by the general and specific methods described below, using the common general knowledge of one skilled in the art of synthetic organic chemistry. Such common general knowledge can be found in standard reference books such as *Comprehensive Organic Chemistry*, Ed. Barton and Ollis, Elsevier; *Comprehensive Organic Transformations: A Guide to Functional Group Preparations*, Larock, John Wiley and Sons; and *Compendium of Organic Synthetic Methods*, Vol. I-XII (published by Wiley-Interscience). The starting materials used herein are commercially available or may be prepared by routine methods known in the art.

In the preparation of the compounds of any one of the formulae described above, it is noted that some of the preparation methods described herein may require protection of remote functionality (e.g., primary amine, secondary amine, carboxyl in any one of the formulae described above precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see Greene, *Protective Groups in Organic Synthesis*, John Wiley & Sons, New York, 1991.

For example, certain compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly used in peptide synthesis (such as N-t-butoxycarbonyl (Boc), benzyloxycarbonyl (Cbz), and 9-fluorenylmethylenoxycarbonyl (Fmoc) for amines, and lower alkyl or benzyl esters for carboxylic acids) which are generally not chemically reactive under the reaction conditions described and can typically be removed without chemically altering other functionality in the any one of the formulae described above compounds.

The Schemes described below are intended to provide a general description of the methodology employed in the preparation of the compounds of the present disclosure. Some of the compounds of the present present disclosure may contain single or multiple chiral centers with the stereochemical designation (R) or (S). It will be apparent to one skilled in the art that all of the synthetic transformations can be conducted in a similar manner whether the materials are enantioenriched or racemic. Moreover, the resolution to the desired optically active material may take place at any desired point in the sequence using well known methods such as described herein and in the chemistry literature.

EXAMPLES

Abbreviations

Ar Argon

DAST Diethylaminosulfur trifluoride

DCM Dichloromethane

DIEA N,N-Diisopropylethylamine

DMF N,N-dimethylformamide

DMF-DMA N,N-dimethylformamide dimethyl acetal

DMSO Dimethyl sulfoxide

Dppf 1,1'-Bis(diphenylphosphino)ferrocene

EA Ethyl acetate

EtOH Ethanol

EtOAc Ethyl acetate

HATU N-[(Dimethylamino)-1H-1,2,3-triazolo-[4,5-b]pyridin-1-ylmethylene]-N methylmethanaminium hexafluorophosphate N-oxide HPLC High performance liquid chromatography i-PrOH Isopropyl alcohol LC-MS Liquid chromatography-mass spectrometry MeOH Methanol $Pd(dppf)Cl_2$ Dichloro[1,1'-bis(diphenylphosphino)ferrocene]palladium $Pd(PPh_3)_4$ Tetrakis(triphenylphosphine)Palladium PE Petroleum ether TEA Triethylamine THF Tetrahydrofuran Tf Triflate Ts Tosyl Xantphos 4,5-Bis(diphenylphosphino)-9,9-dimethylxanthene

Synthetic Example 1. Synthetic Processes to Prepare Intermediates

Intermediate 1

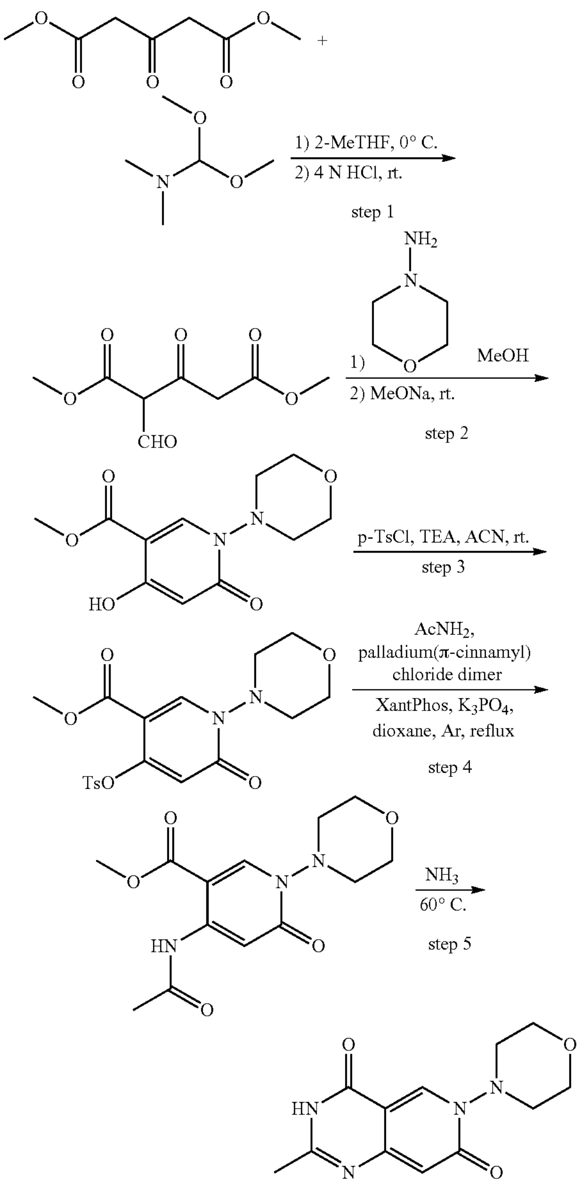

inetermediate 1

Step 1:

To a stirred solution of 2-MeTHF (75 mL) was added dimethyl 3-oxopentanedioate (10 g, 57.4 mmol) and DMF-DMA (6.8 g, 57.4 mmol) at 4° C. The mixture was stirred for 3 hours. The reaction mixture was warmed to room temperature, and aqueous hydrochloric acid (4 N, 26 mL) was slowly added. After stirring 3 hours at room temperature, the organic layer was separated, washed with water (20 mL), brine (20 mL), dried over $Na_2SO_4$, filtered and concentrated in vacuo to give dimethyl 2-formyl-3-oxo-pentanedioate (11 g, 95% yield) as a light yellow liquid, which was used directly without further purification. LC-MS: m/z 202.9 $[M+H]^+$.

Step 2:

A mixture of dimethyl 2-formyl-3-oxo-pentanedioate (2.3 g, 11.5 mmol), morpholin-4-amine (1.1 g, 10.4 mmol) in MeOH (15 mL) was stirred at room temperature for 12 hours. MeONa (647.9 mg, 12.0 mmol) was added to the mixture and stirred for 6 hours. The mixture was quenched with $H_2O$ (15 mL), acidified with aq. HCl (1 N) to pH 1-2. The resulting solid was filtered, washed with MeOH and $H_2O$ (1:1, V:V), and dried in vacuo to give methyl 4-hydroxy-1-morpholino-6-oxo-pyridine-3-carboxylate (2 g, 75% yield) as a white solid. LC-MS: m/z 254.9 $[M+H]^+$.

Step 3:

To a stirred solution of methyl 4-hydroxy-1-morpholino-6-oxo-pyridine-3-carboxylate (2.0 g, 7.9 mmol) and TEA (1.2 g, 11.8 mmol) in $CH_3CN$ (50 mL) was added 4-methylbenzenesulfonyl chloride (1.5 g, 7.9 mmol). The mixture was stirred at room temperature for 1 hour. The resulting solid was filtered and washed with $CH_3CN$ to give methyl 1-morpholino-6-oxo-4-(p-tolylsulfonyloxy)pyridine-3-carboxylate (2.6 g, 81% yield). LC-MS: m/z 408.8 $[M+H]^+$.

Step 4:

A mixture of methyl 1-morpholino-6-oxo-4-(p-tolylsulfonyloxy)pyridine-3-carboxylate (2.0 g, 5.0 mmol), acetamide (590.1 mg, 10 mmol), palladium (π-cinnamyl) chloride dimer (129.4 mg, 249.7 μmol), XantPhos (289.2 mg, 499.5 μmol) and $K_3PO_4$ (2.7 g, 12.5 mmol) in dioxane (50 mL) was stirred at 100° C. for 12 hours. The mixture was purified by flash column chromatography to give methyl 4-acetamido-1-morpholino-6-oxo-pyridine-3-carboxylate (1.0 g, 68% yield). LC-MS: m/z 295.9 $[M+H]^+$.

Step 5:

A mixture of methyl 4-acetamido-1-morpholino-6-oxo-pyridine-3-carboxylate (295 mg, 1.0 mmol) and a solution of $NH_3$ in MeOH (7 M, 5 mL) was heated to 60° C. for 16 hours. The mixture was concentrated and filtered to give 2-methyl-6-morpholino-3H-pyrido[4,3-d]pyrimidine-4,7-dione (200 mg, 76% yield), which was used to the next step without further purification. LC-MS: m/z 262.9 $[M+H]^+$.

Additional intermediates of the present disclosure were prepared by using the corresponding derivatives in analogy to the representative procedures described for intermediate 1. Selected compounds and their corresponding characterization data are presented in Table below.

| ID | Structure | LC-MS: m/z $[M + H]^+$ |
|---|---|---|
| Intermediate 2 | 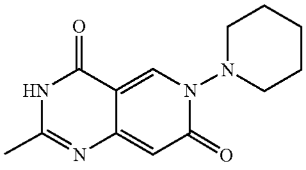 [SMILES: Cc1nc2cc(=O)n(N3CCCCC3)cc2c(=O)[nH]1] | 260.9 |

-continued
| ID | Structure | LC-MS: m/z [M + H]$^+$ |
|---|---|---|
| Intermediate 3 | 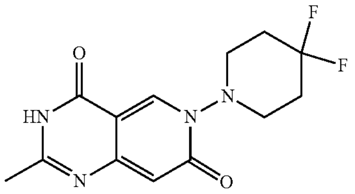 [SMILES: Cc1nc2cc(=O)n(N3CCC(F)(F)CC3)cc2c(=O)[nH]1] | 296.9 |
| Intermediate 4 | 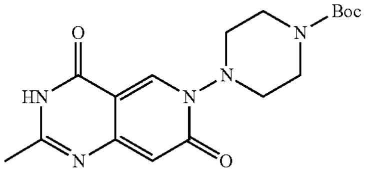 [SMILES: Cc1nc2cc(=O)n(N3CCN(C(=O)OC(C)(C)C)CC3)cc2c(=O)[nH]1] | 361.9 |
| Intermediate 5 | 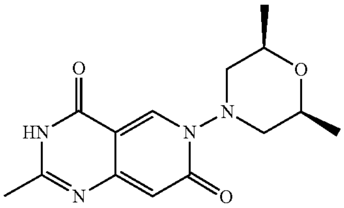 | 290.8 |
| Intermediate 6 | 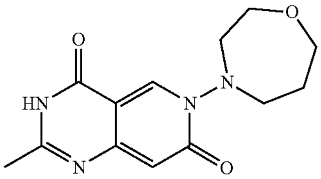 [SMILES: Cc1nc2cc(=O)n(N3CCCOCC3)cc2c(=O)[nH]1] | 276.9 |
| Intermediate 7 | 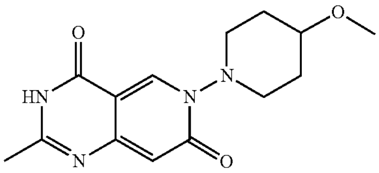 | 290.8 |
| Intermediate 8 | 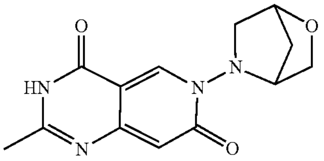 [SMILES: Cc1nc2cc(=O)n(N3CC4CC3CO4)cc2c(=O)[nH]1] | 274.9 |
| Intermediate 9 | 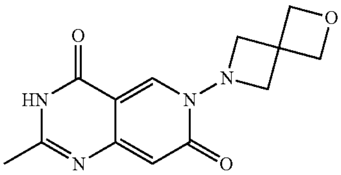 [SMILES: Cc1nc2cc(=O)n(N3CC4(COC4)C3)cc2c(=O)[nH]1] | 274.8 |

Intermediate 10

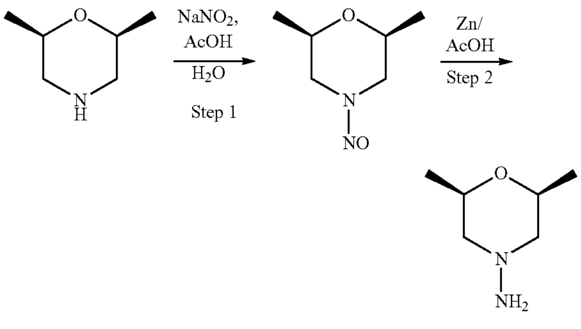

Step 1:

To a solution of (2S,6R)-2,6-dimethylmorpholine (2.0 g, 17.4 mmol) in water (25 mL) was added sodium nitrite (1.8 g, 26.1 mmol) and acetic acid (1.4 g, 22.5 mmol) at 0° C. The mixture was stirred at 20° C. for 2 hours. The mixture was diluted with $CH_2Cl_2$ (80 mL) and then washed with aq. $NaHCO_3$(30 mL). The organic layer was dried over $Na_2SO_4$, filtered and concentrated to afford (2S,6R)-2,6-dimethyl-4-nitroso-morpholine (2.5 g, 99% yield) as yellow oil.

Step 2:

To a solution of (2S,6R)-2,6-dimethyl-4-nitroso-morpholine (2.5 g, 17.4 mmol) in $CH_3OH$ (25 mL) was added acetic acid (3.1 g, 52.1 mmol) and zinc (3.4 g, 52.1 mmol) at 0° C. The mixture was stirred at 20° C. for 4 hours. The mixture was filtered, and the filtrate was concentrated to afford (2S,6R)-2,6-dimethylmorpholin-4-amine (7 g) as a white solid.

The following compounds have been prepared in analogy to the representative procedures described for intermediate 10.

| ID | Structure | LC-MS: m/z [M + H]$^+$ |
|---|---|---|
| Intermediate 11 | 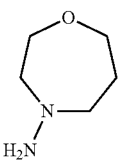 | 116.8 |
| Intermediate 12 | 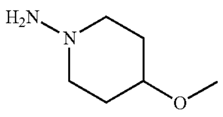 | 130.9 |
| Intermediate 13 | 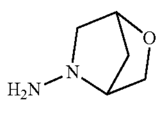 | 114.8 |
| Intermediate 14 | 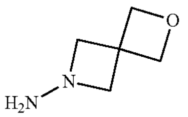 | 114.7 |

Intermediate 15

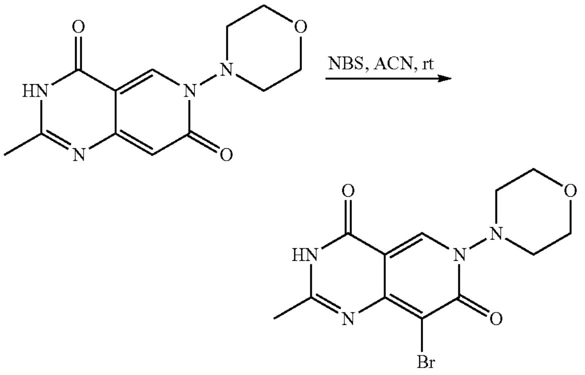

A mixture of 2-methyl-6-morpholino-3H-pyrido[4,3-d]pyrimidine-4,7-dione (26.2 mg, 99.9 μmol) and 1-bromopyrrolidine-2,5-dione (17.8 mg, 99.9 μmol) in $CH_3CN$ (2 mL) was stirred at room temperature for 3 hours. The reaction mixture was concentrated and washed with MeOH (5 mL) to give 8-bromo-2-methyl-6-morpholinopyrido[4,3-d]pyrimidine-4,7(3H,6H)-dione (25 mg). LC-MS: m/z 341.7 [M+H]$^+$.

Intermediate 16

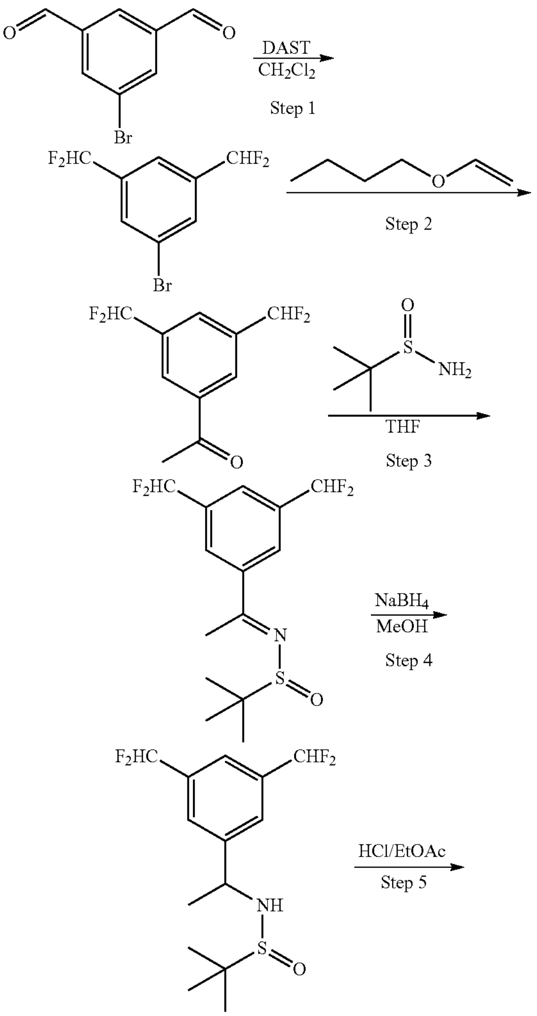

-continued

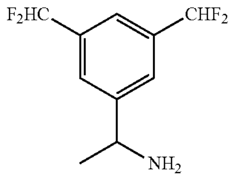

Step 1:

To a solution of 5-bromobenzene-1,3-dicarbaldehyde (5 g, 23.5 mmol) in $CH_2Cl_2$ (70 mL) was added DAST (22.7 g, 140.8 mmol) at 0° C. slowly. The mixture was stirred at 20° C. for 8 hours. The solution was poured into ice (120 mL) and saturated sodium bicarbonate (100 mL) was added. The mixture was extracted with $CH_2Cl_2$ (3×200 mL). The organic layer was combined, dried over $Na_2SO_4$, filtered, concentrated and purified by column chromatography on silica gel to afford 1-bromo-3,5-bis(difluoromethyl)benzene (3.8 g, 63% yield) as colorless oil.

Step 2:

To a solution of 1-vinyloxybutane (779.3 mg, 7.7 mmol), 1-bromo-3,5-bis(difluoromethyl)benzene (1 g, 3.9 mmol), $Pd(OAc)_2$ (87.3 mg, 389.1 μmol), potassium phosphate (1.6 g, 7.7 mmol) and dppf (431.4 mg, 778.1 μmol) in n-BuOH (15 mL) was added LiOTf (606.9 mg, 3.9 mmol). The mixture was degassed with a stream of N2 for three times. The mixture was stirred at 110° C. for 16 hours. The mixture was purified by column chromatography on silica gel to afford colorless oil. Then the oil was dissolved in EtOAc (5 mL) and HCl/EtOAc (5 mL) was added. The mixture was stirred at 20° C. for 1 hour. The mixture was concentrated and purified by column chromatography on silica gel to afford 1-[3,5-bis(difluoromethyl)phenyl]ethanone (260 mg, 30% yield) as a white solid.

Step 3:

To a solution of 1-[3,5-bis(difluoromethyl)phenyl]ethanone (260 mg, 1.2 mmol) and 2-methylpropane-2-sulfinamide (286.2 mg, 2.4 mmol) in THF (8 mL) was added $Ti(OEt)_4$ (538.7 mg, 2.4 mmol). The mixture was stirred at 80° C. for 16 hours. The reaction mixture was diluted with THF (50 mL) and then quenched with water. The mixture was filtered and the filtrate was dried over $Na_2SO_4$, filtered and concentrated to afford N-[1-[3,5-bis(difluoromethyl)phenyl]ethylidene]-2-methyl-propane-2-sulfinamide (400 mg) as a yellow solid which was used for next step directly without further purification.

Step 4:

To a solution of N-[1-[3,5-bis(difluoromethyl)phenyl]ethylidene]-2-methyl-propane-2-sulfinamide (400 mg, 1.2 mmol) in THF (8 mL) was added $NaBH_4$ (140.4 mg, 3.7 mmol). The mixture was stirred at 0° C. for 2 hours. The reaction mixture was quenched with water. The mixture was extracted with EtOAc (2×50 mL). The combined organic layer was dried over $Na_2SO_4$, filtered and concentrated to afford N-[1-[3,5-bis(difluoromethyl)phenyl]ethyl]-2-methyl-propane-2-sulfinamide (400 mg, 99% yield) as a yellow solid.

Step 5:

A solution of N-[1-[3,5-bis(difluoromethyl)phenyl]ethyl]-2-methyl-propane-2-sulfinamide (400 mg, 1.2 mmol) in HCl/EtOAc (8 mL, 4 N) was stirred at 20° C. for 16 hours. The reaction mixture was concentrated. The residue was suspended in EtOAc (50 mL) and washed with aq. $NaHCO_3$ (25 mL). The organic layer was dried over $Na_2SO_4$, filtered and concentrated to afford 1-[3,5-bis(difluoromethyl)phenyl]ethanamine (150 mg, 55% yield) as oil.

Intermediate 17

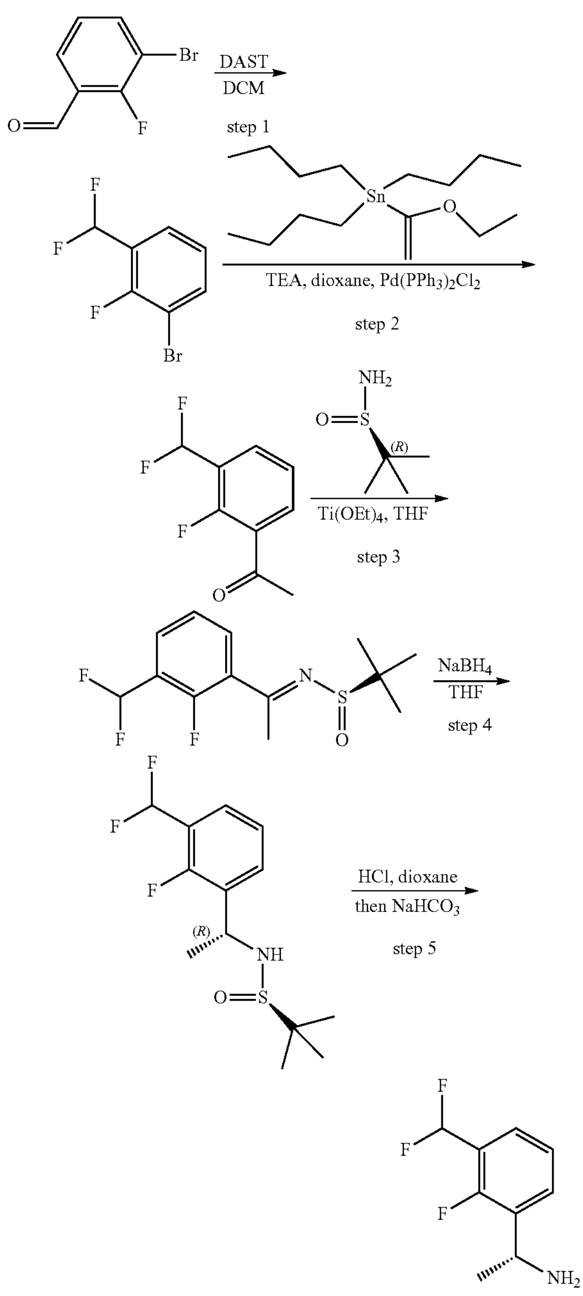

Step 1:

To a solution of 3-bromo-2-fluorobenzaldehyde (200 g, 956 mmol) in dichloromethane (3000 mL) under N2 was added DAST (308 g, 1912 mmol) at 0° C., and the mixture was stirred for 1 h at 0° C. The mixture was warmed to room temperature and stirred for 1 h. The reaction was carefully quenched with saturated sodium bicarbonate solution. The reaction mixture was then diluted with ethyl acetate (3000 mL) and the organic layer was washed with saturated sodium bicarbonate solution and brine then concentrated to dryness and purified by chromatography (0-50% ethyl acetate in PE over 20 minutes) to provide 1-bromo-3-(difluoromethyl)-2-fluorobenzene (135 g, 61% yield) as oil.

Step 2:

1-bromo-3-(difluoromethyl)-2-fluorobenzene (125 g, 556 mmol) was dissolved in anhydrous 1,4-dioxane (1.2 L). Triethylamine (140 mL, 1389 mmol) and tributyl(1-ethoxyvinyl)tin (241 g, 667 mmol) were added and the resulting solution was purged with argon for 15 min. Bis(triphenylphosphine)palladium(II)chloride (3.9 g, 5.6 mmol) was added. The reaction mixture was heated to 100° C. in an autoclave for 16 h. After complete conversion of the starting material, the reaction mixture was cooled to room temperature and treated with 1 N HCl and stirred for additional 16 h. The aqueous layer was extracted with EtOAc. The combined organic layers were dried over $Na_2SO_4$, filtered and the solvent was removed under reduced pressure. The crude product was purified by flash chromatography ($SiO_2$, hexane/ethyl acetate 10:1) to afford 1-(3-(difluoromethyl)-2-fluorophenyl)ethanone (78 g, 76% yield). LC-MS: m/z 189.0 $[M+H]^+$.

Step 3:

1-(3-(difluoromethyl)-2-fluorophenyl)ethanone (70 g, 372 mmol) was dissolved in THF (1.0 L). (R)-(+)-2-methyl-2-propanesulfinamide (68.3 g, 564 mmol) and titanium tetraethoxide (257.5 g, 1129 mmol) were added at room temperature. The resulting reaction mixture was heated to 80° C. for 16 h. After complete conversion of the starting material, ice water and EtOAc were added and the aqueous layer was extracted with EtOAc. The organic layers were combined, dried over $Na_2SO_4$ and concentrated under reduced pressure to give (R,E)-N-(1-(3-(difluoromethyl)-2-fluorophenyl)ethylidene)-2-methylpropane-2-sulfinamide, which was used without further purification in the next step. LC-MS: m/z 292.0 $[M+H]^+$.

Step 4:

A solution of (R,E)-N-(1-(3-(difluoromethyl)-2-fluorophenyl)ethylidene)-2-methylpropane-2-sulfinamide (100 g, 343.6 mmol) was dissolved in THF (1.2 L) and cooled to 0° C. Sodium borohydride (12.7 g, 343.2 mmol) was added, and the resulting reaction mixture was stirred at room temperature for 6 h. After complete conversion of the starting material, ice water and EtOAc were added. The aqueous layer was extracted with EtOAc. combined, dried over $Na_2SO_4$ and concentrated under reduced pressure. The crude product was purified by chromatography (gradient elution: 33% ethyl acetate in petroleum ether) yielding isomer 1: (R)—N—((R)-1-(3-(difluoromethyl)-2-fluorophenyl)ethyl)-2-methylpropane-2-sulfinamide (65 g, 64% yield) as yellow oil. LC-MS: m/z 294.0 $[M+H]^+$; isomer 2: (R)—N—((S)-1-(3-(difluoromethyl)-2-fluorophenyl)ethyl)-2-methylpropane-2-sulfinamide as yellow oil. LC-MS: m/z 294.0 $[M+H]^+$.

Step 5:

A solution of (R)—N—((R)-1-(3-(difluoromethyl)-2-fluorophenyl)ethyl)-2-methylpropane-2-sulfinamide (65 g, 221.8 mmol) in EA (600 mL) was added 4N HCl in dioxane (300 mL) and stirred for 1.5 h at RT under N2. After completion of the reaction, the solution was removed in vacuum and the solid was collected and diluted with water. The mixture was adjusted pH=8 by aq. $NaHCO_3$ and extracted with EA (3×300 mL). The combined organic layers were concentrated to give (R)-1-(3-(difluoromethyl)-2-fluorophenyl)ethan-1-amine (31 g, 73% yield) as light yellow oil. LC-MS: m/z 191.1 $[M+H]^+$. ee value=99%, RT=0.88 min (column: Cellulose-SC, 4.6*100 mm, 5 μm).

(S)-1-(3-(difluoromethyl)-2-fluorophenyl)ethan-1-amine was prepared by same procedure using (R)—N—((S)-1-(3-(difluoromethyl)-2-fluorophenyl)ethyl)-2-methylpropane-2-sulfinamide as starting material. LC-MS: m/z 191.1 $[M+H]^+$. RT=1.12 min (column: Cellulose-SC, 4.6*100 mm, 5 μm).

Synthetic Example 2. Synthetic Processes to Prepare Exemplified Compounds

Synthetic Examples

Example 1

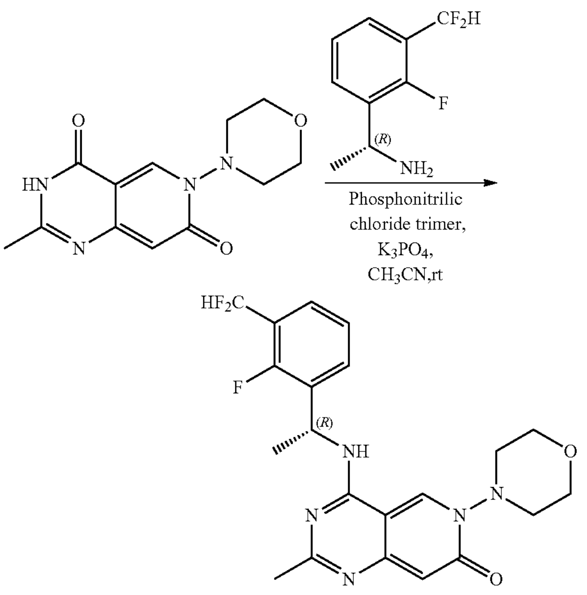

To a stirred solution of 2-methyl-6-morpholino-3H-pyrido[4,3-d]pyrimidine-4,7-dione (52.4 mg, 199.8 μmol) in $CH_3CN$ (10 mL) was added $K_3PO_4$ (105.9 mg, 499.5 μmol) and 2,2,4,4,6,6-hexachloro-1,3,5-triaza-2,4,6-triphosphacyclohexa-1,3,5-triene (69.5 mg, 199.8 μmol). The mixture was stirred at room temperature for 2 hours. (1R)-1-[3-(difluoromethyl)-2-fluoro-phenyl]ethanamine (37.8 mg, 199.8 μmol) was added and the mixture was stirred for 2 hours. The reaction mixture was concentrated and purified by prep-HPLC to give 4-[[(1R)-1-[3-(difluoromethyl)-2-fluoro-phenyl]ethyl]amino]-2-methyl-6-morpholino-pyrido[4,3-d]pyrimidin-7-one (20 mg, 24% yield). LC-MS: m/z 433.8 $[M+H]^+$.

The following compounds have been prepared in analogy to the representative procedures described for example 1.

| ID | Structure | LC-MS: m/z [M + H]+ |
|---|---|---|
| Example 2 | 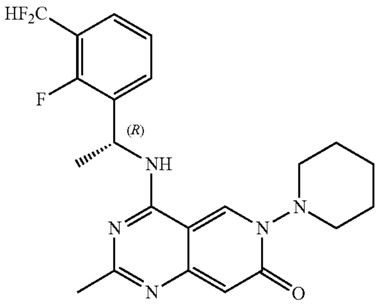 | 431.9 |
| Example 3 | 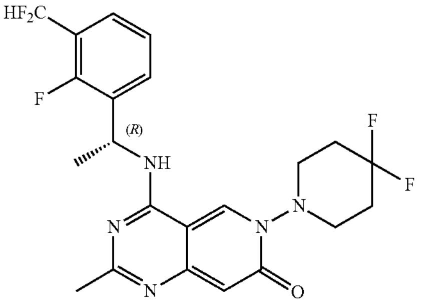 | 467.8 |
| Example 4 | 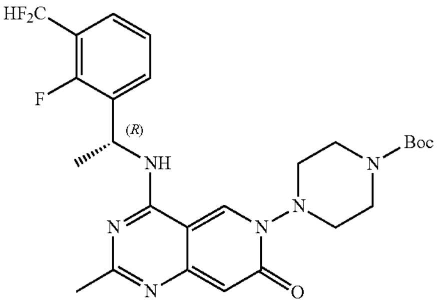 | 532.8 |
| Example 5 | 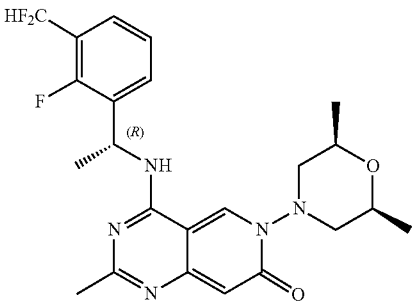 | 461.9 |
| Example 6 | 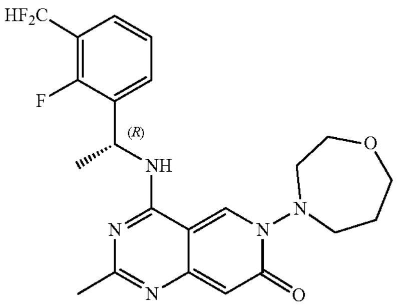 | 447.8 |

-continued
| ID | Structure | LC-MS: m/z [M + H]+ |
| --- | --- | --- |
| Example 7 | 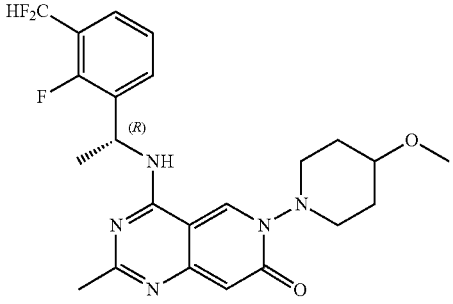 | 461.8 |
| Example 8 | 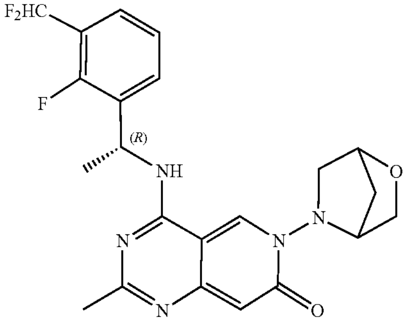 | 445.8 |
| Example 9 | 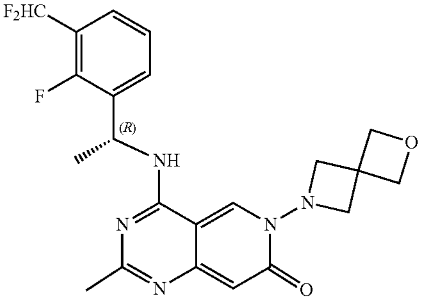 | 445.7 |
Example 10
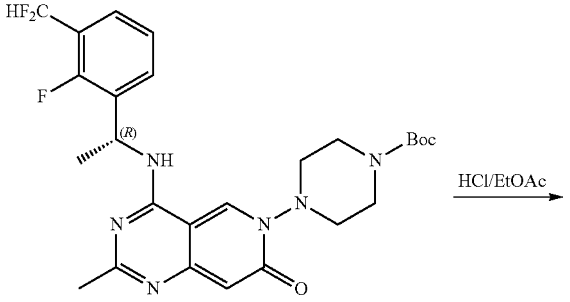
-continued
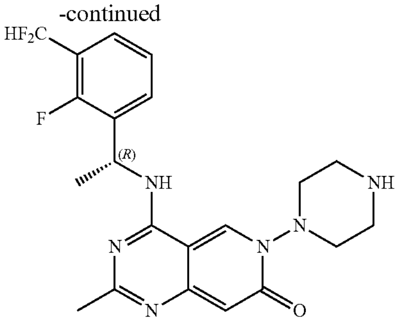
A solution of tert-butyl 4-[4-[[(1R)-1-[3-(difluoromethyl)-2-fluoro-phenyl]ethyl]amino]-2-methyl-7-oxo-pyrido[4,3-d]pyrimidin-6-yl]piperazine-1-carboxylate (500 mg, 938.8 μmol) in HCl/EtOAc (10 mL) (4 N) was stirred at 20° C. for 1.5 hours. The mixture was concentrated and purified by prep-HPLC to afford 4-[[(1R)-1-[3-(difluoromethyl)-2-fluoro-phenyl]ethyl]amino]-2-methyl-6-piperazin-1-yl-pyrido[4,3-d]pyrimidin-7-one (110 mg, 27% yield) as a light yellow solid. LC-MS: m/z 432.8 [M+H]$^+$.

Example 11

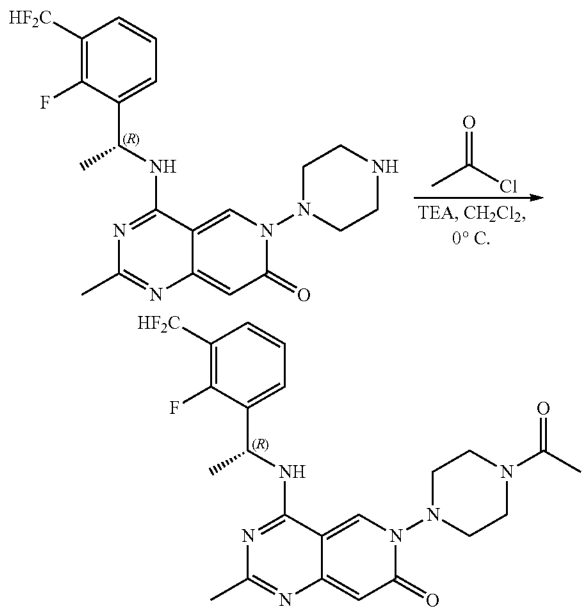

To a solution of 4-[[(1R)-1-[3-(difluoromethyl)-2-fluoro-phenyl]ethyl]amino]-2-methyl-6-piperazin-1-yl-pyrido[4,3-d]pyrimidin-7-one (60 mg, 127.9 μmol) in $CH_2Cl_2$ (4 mL) was added TEA (38.8 mg, 383.8 μmol) and acetyl chloride (10.0 mg, 127.9 μmol) at 0° C. The mixture was stirred at 0° C. for 2 hours. The mixture was diluted with $CH_2Cl_2$ (50 mL) and then washed with brine (20 mL). The organic layer was dried over $Na_2SO_4$, filtered, concentrated and purified by prep-HPLC to afford 6-(4-acetylpiperazin-1-yl)-4-[[(1R)-1-[3-(difluoromethyl)-2-fluoro-phenyl]ethyl]amino]-2-methyl-pyrido[4,3-d]pyrimidin-7-one (14.1 mg, 23% yield). LC-MS: m/z 474.8 [M+H]$^+$.

Example 12

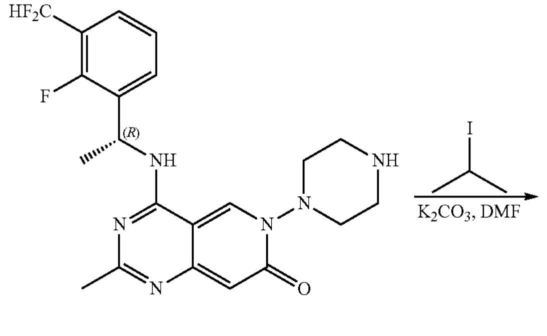

-continued

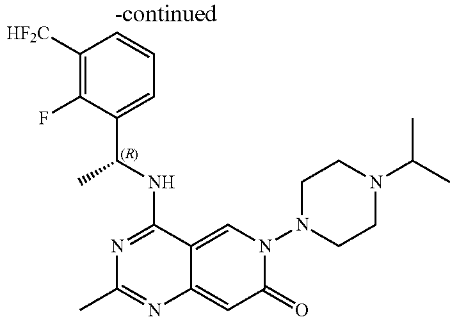

A solution of 2-iodopropane (39.9 mg, 234.8 μmol), potassium carbonate (40.6 mg, 293.5 μmol) and 4-[[(1R)-1-[3-(difluoromethyl)-2-fluoro-phenyl]ethyl]amino]-6-(4-isopropylpiperazin-1-yl)-2-methyl-pyrido[4,3-d]pyrimidin-7-one (60 mg, 117.4 μmol) in DMF (3 mL) was stirred at 40° C. for 16 hours. The mixture was diluted with EtOAc (100 mL) and then washed with brine (3×320 mL). The organic layer was dried over $Na_2SO_4$, filtered, concentrated and purified by column chromatography on silica gel to afford 4-[[(1R)-1-[3-(difluoromethyl)-2-fluoro-phenyl]ethyl]amino]-6-(4-isopropylpiperazin-1-yl)-2-methyl-pyrido[4,3-d]pyrimidin-7-one (1.9 mg, 3% yield) as a light yellow solid. LC-MS: m/z 474.9 [M+H]$^+$.

Example 13

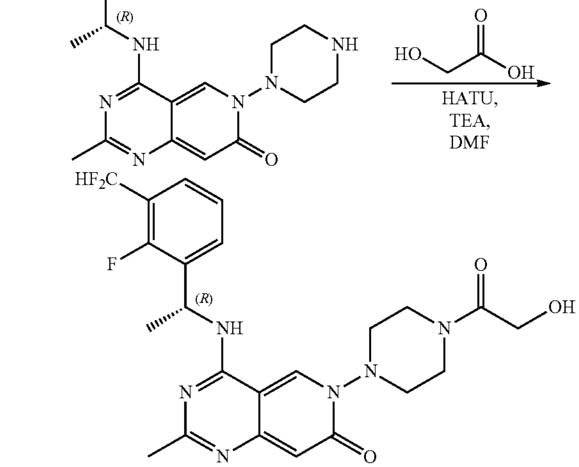

To a solution of 4-[[(1R)-1-[3-(difluoromethyl)-2-fluoro-phenyl]ethyl]amino]-2-methyl-6-piperazin-1-yl-pyrido[4,3-d]pyrimidin-7-one (60 mg, 127.9 μmol), TEA (38.8 mg, 383.9 μmol) and 2-hydroxyacetic acid (9.7 mg, 127.9 μmol) in DMF (3 mL) was added HATU (73.4 mg, 191.9 μmol). The mixture was stirred at 20° C. for 2 hours. The mixture was diluted with EtOAc (100 mL) and then washed with brine (3×20 mL). The organic layer was dried over $Na_2SO_4$, filtered, concentrated and purified by column chromatography on silica gel to afford 4-[[(1R)-1-[3-(difluoromethyl)-2-fluoro-phenyl]ethyl]amino]-6-[4-(2-hydroxyacetyl)piperazin-1-yl]-2-methyl-pyrido[4,3-d]pyrimidin-7-one (2.1 mg, 3% yield) as a light yellow solid. LC-MS: m/z 490.8 [M+H]$^+$.

The following compound has been prepared in analogy to the representative procedures described for example 13.

| ID | Structure | LC-MS: m/z [M + H]+ |
| --- | --- | --- |
| Example 14 | 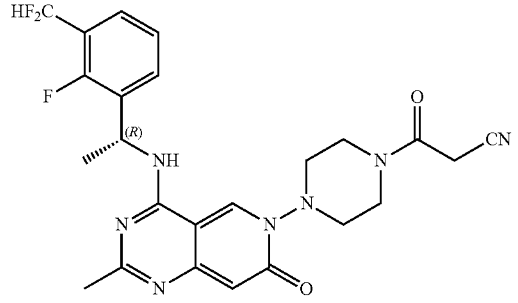 | 499.8 |

Example 15

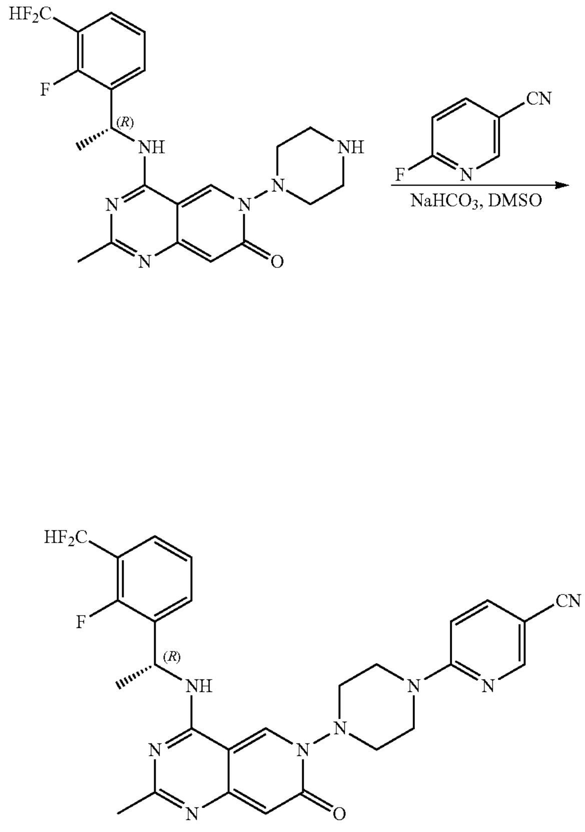

A solution of 6-fluoropyridine-3-carbonitrile (28.6 mg, 234.8 μmol), $NaHCO_3$(16.7 mg, 199.6 μmol) and 4-[[(1R)-1-[3-(difluoromethyl)-2-fluoro-phenyl]ethyl]amino]-2-methyl-6-piperazin-1-yl-pyrido[4,3-d]pyrimidin-7-one (50.7 mg, 117.4 μmol) in DMSO (3 mL) was stirred at 100° C. for 6 hours. The mixture was diluted with EtOAc (100 mL) and then washed with brine (3×20 mL). The organic layer was dried over $Na_2SO_4$, filtered, concentrated and purified by column chromatography on silica gel to afford 6-[4-[4-[[(1R)-1-[3-(difluoromethyl)-2-fluoro-phenyl]ethyl] amino]-2-methyl-7-oxo-pyrido[4,3-d]pyrimidin-6-yl]piperazin-1-yl]pyridine-3-carbonitrile (2 mg, 3% yield) as a light yellow solid. LC-MS: m/z 534.8 $[M+H]^+$.

Example 16

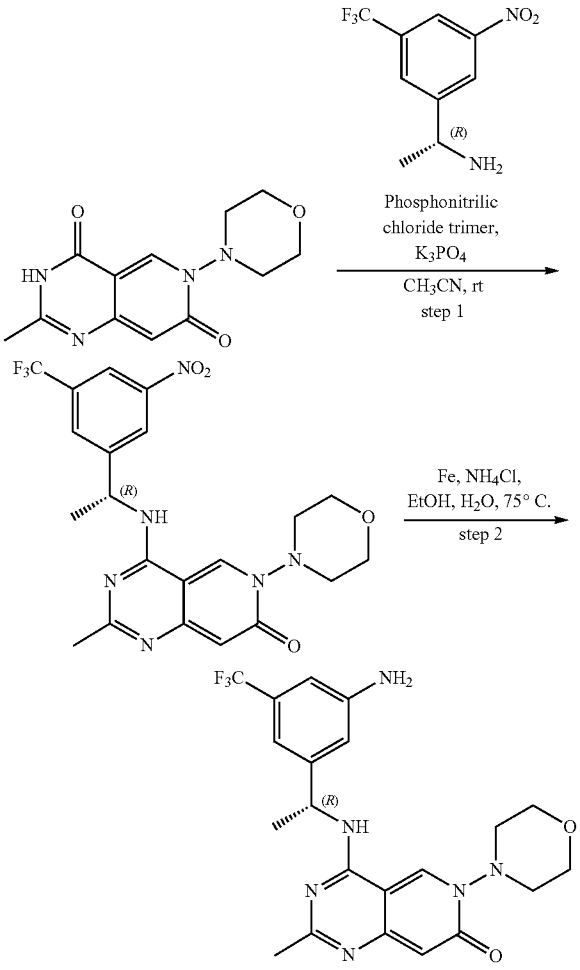

Step 1:

To a stirred solution of 2-methyl-6-morpholino-3H-pyrido[4,3-d]pyrimidine-4,7-dione (100 mg, 381.3 μmol) and $K_3PO_4$ (202.1 mg, 953.2 μmol) in $CH_3CN$ (15 mL) was added phosphonitrilic chloride trimer (132.7 mg, 381.3 μmol). The mixture was stirred at room temperature for 2 hours. (1R)-1-[3-nitro-5-(trifluoromethyl)phenyl]

ethanamine (89.3 mg, 381.3 μmol) was added. The mixture was stirred for 2 hours. The reaction mixture was concentrated and purified by flash column chromatography to give 2-methyl-6-morpholino-4-[[(1R)-1-[3-nitro-5-(trifluoromethyl)phenyl]ethyl]amino]pyrido[4,3-d]pyrimidin-7-one (50 mg, 27% yield). LC-MS: m/z 478.8 $[M+H]^+$.

Step 2:

A mixture of 2-methyl-6-morpholino-4-[[(1R)-1-[3-nitro-5-(trifluoromethyl)phenyl]ethyl]amino]pyrido[4,3-d]pyrimidin-7-one (10 mg, 20.9 μmol), iron (5.8 mg, 104.5 μmol) and $NH_4Cl$ (11.2 mg, 209.0 μmol) in EtOH (2 mL) and $H_2O$ (2 mL) was stirred at 75° C. for 3 hours. The reaction mixture was concentrated and purified by prep-HPLC to give 4-[[(1R)-1-[3-amino-5-(trifluoromethyl)phenyl]ethyl]amino]-2-methyl-6-morpholino-pyrido[4,3-d]pyrimidin-7-one (2 mg, 21% yield). LC-MS: m/z 448.8 $[M+H]^+$.

Example 17

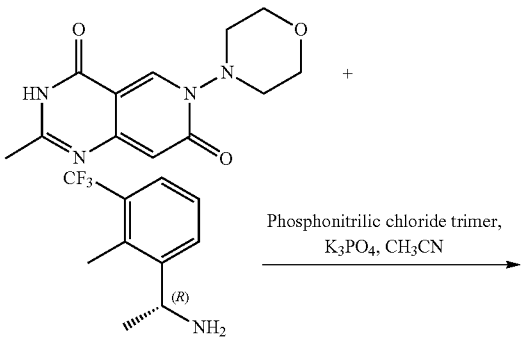

-continued

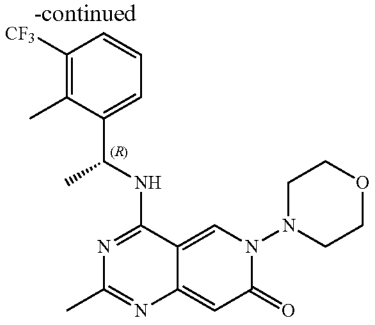

A mixture of 2-methyl-6-morpholinopyrido[4,3-d]pyrimidine-4,7(3H,6H)-dione (52.4 mg, 0.2 mmol), $K_3PO_4$ (106 mg, 0.5 mmol) and phosphonitrilic chloride trimer (70 mg, 0.2 mmol) in $CH_3CN$ (10 mL) was stirred at room temperature for 3 hours. (R)-1-(2-methyl-3-(trifluoromethyl)phenyl)ethan-1-amine (45 mg, 0.22 mmol) was added. The mixture was stirred at 80° C. for 2 hours. The solvent was removed. DCM (100 mL) and water (20 mL) was added. The mixture was stirred for 20 min. The organic phase was dried over $Na_2SO_4$, filtered, concentrated and purified by prep-HPLC to give (R)-2-methyl-4-((1-(2-methyl-3-(trifluoromethyl)phenyl)ethyl)amino)-6-morpholinopyrido[4,3-d]pyrimidin-7(6H)-one (15 mg). LC-MS: m/z 447.8 $[M+H]^+$.

The following compounds have been prepared in analogy to the representative procedures described for example 17.

| ID | Structure | LC-MS: m/z $[M + H]^+$ |
|---|---|---|
| Example 18 | 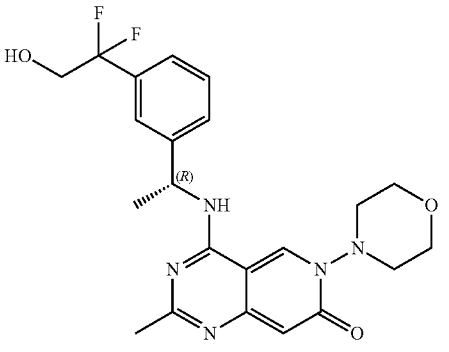 | 445.8 |
| Example 19 | 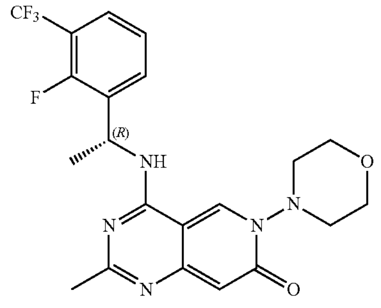 | 451.8 |

-continued
| ID | Structure | LC-MS: m/z $[M + H]^+$ |
|---|---|---|
| Example 20 | 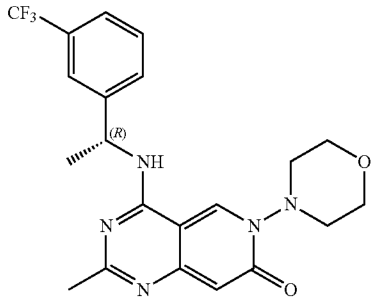 | 433.8 |
| Example 21 | 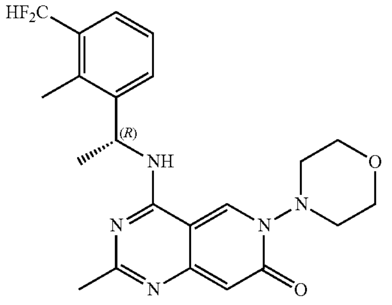 | 429.8 |
| Example 22 | 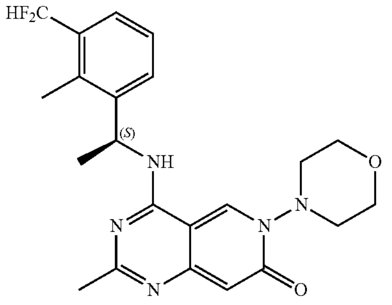 | 429.8 |
| Example 23 | 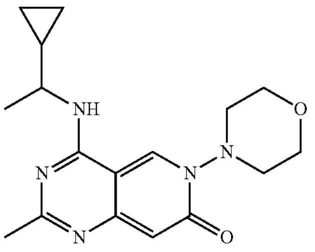 [SMILES: Cc1nc(NC(C)C2CC2)c2cn(N3CCOCC3)c(=O)cc2n1] | 329.9 |
| Example 24 | 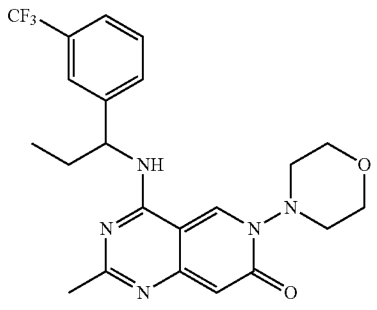 [SMILES: CCC(Nc1nc(C)nc2cc(=O)n(N3CCOCC3)cc12)c1cccc(C(F)(F)F)c1] | 447.8 |

-continued
| ID | Structure | LC-MS: m/z [M + H]$^+$ |
|---|---|---|
| Example 25 | 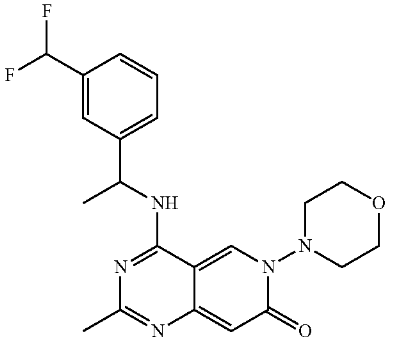 [SMILES: Cc1nc(NC(C)c2cccc(C(F)F)c2)c2cn(N3CCOCC3)c(=O)cc2n1] | 415.8 |
| Example 26 | 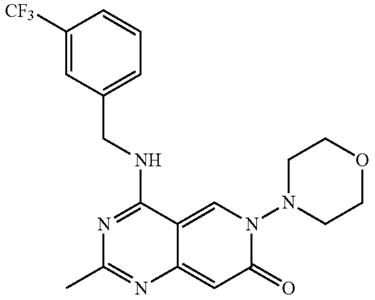 [SMILES: Cc1nc(NCc2cccc(C(F)(F)F)c2)c2cn(N3CCOCC3)c(=O)cc2n1] | 419.8 |
| Example 27 | 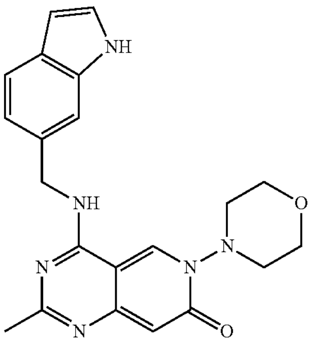 [SMILES: Cc1nc(NCc2ccc3cc[nH]c3c2)c2cn(N3CCOCC3)c(=O)cc2n1] | 390.8 |
| Example 28 | 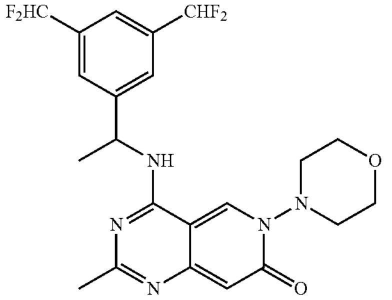 [SMILES: Cc1nc(NC(C)c2cc(C(F)F)cc(C(F)F)c2)c2cn(N3CCOCC3)c(=O)cc2n1] | 465.8 |

Example 29

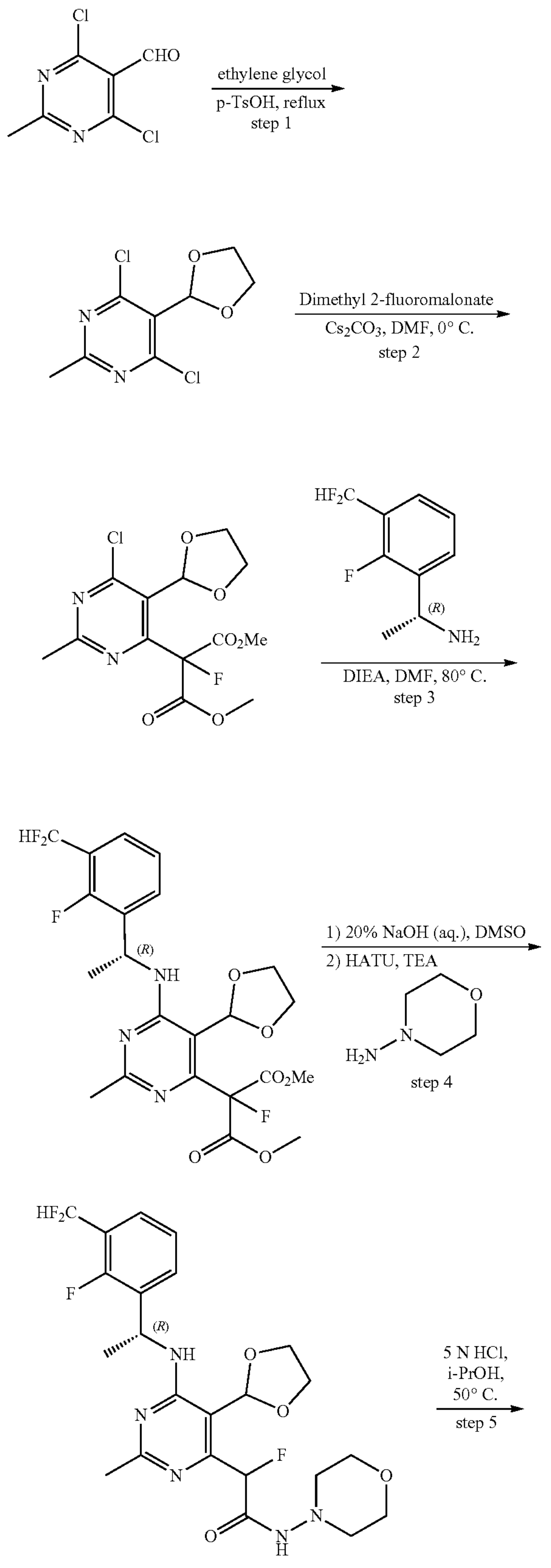

-continued

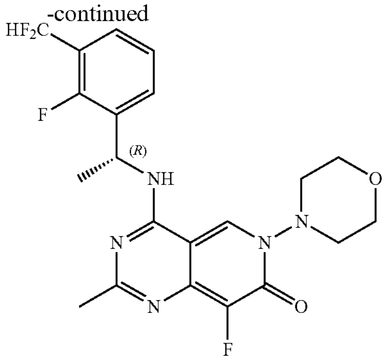

Step 1:

To a stirred solution of 4,6-dichloro-2-methylpyrimidine-5-carbaldehyde (5.0 g, 26 mmol) in toluene (150 mL) was added ethylene glycol (8.0 g, 131.0 mmol) and TsOH (0.5 g, 2.5 mmol). The reaction mixture was refluxed in a water segregator until full conversion of the starting material is observed. The solvent was evaporated under reduced pressure. The residue was diluted with DCM (150 mL) and washed with an aqueous sodium bicarbonate solution. Organic layers are combined, dried over $Na_2SO_4$, concentrated under reduced pressure and purified by flash column chromatography to give 4,6-dichloro-5-(1,3-dioxolan-2-yl)-2-methylpyrimidine (4.0 g). LC-MS: m/z 457.2 $[M+H]^+$.

Step 2:

A mixture of 4,6-dichloro-5-(1,3-dioxolan-2-yl)-2-methylpyrimidine (1.5 g, 6.4 mmol), dimethyl 2-fluoromalonate (960 mg, 6.4 mmol) and $Cs_2CO_3$ (2.1 g, 6.4 mmol) in DMF was stirred at 0° C. for 1 h. The mixture was diluted with EtOAc (200 mL) and $H_2O$ (30 mL). The mixture was stirred at rt for 10 min. The organic phase was washed with water (3x200 mL), dried over $Na_2SO_4$, filtered and concentrated to give the crude product, which was purified by column chromatography to give dimethyl 2-(6-chloro-5-(1,3-dioxolan-2-yl)-2-methylpyrimidin-4-yl)-2-fluoromalonate (1.2 g). LC-MS: m/z 348.8 $[M+H]^+$.

Step 3:

A mixture of dimethyl 2-(6-chloro-5-(1,3-dioxolan-2-yl)-2-methylpyrimidin-4-yl)-2-fluoromalonate (370 mg, 1.1 mmol), (R)-1-(3-(difluoromethyl)-2-fluorophenyl)ethan-1-amine (200 mg, 1.1 mmol) and DIEA (410 mg, 3.2 mmol) in DMF was stirred at 80° C. for 5 h. The mixture was diluted with EtOAc (100 mL) and $H_2O$ (20 mL). The mixture was stirred at rt for 10 min. The organic phase was washed with water (3x200 mL), dried over $Na_2SO_4$, filtered and concentrated to give the crude product, which was purified by column chromatography to give dimethyl (R)-2-(6-((1-(3-(difluoromethyl)-2-fluorophenyl)ethyl)amino)-5-(1,3-dioxolan-2-yl)-2-methylpyrimidin-4-yl)-2-fluoromalonate (400 mg). LC-MS: m/z 501.8 $[M+H]^+$.

Step 4:

Dimethyl (R)-2-(6-((1-(3-(difluoromethyl)-2-fluorophenyl)ethyl)amino)-5-(1,3-dioxolan-2-yl)-2-methylpyrimidin-4-yl)-2-fluoromalonate (320 mg, 0.6 mmol) was dissolved in DMSO (5 mL). An aqueous sodium hydroxide solution (20%, 384 mg) is added and the resulting mixture was stirred for 1 h until complete conversion of the starting material is observed. Triethylamine (130 mg, 1.3 mmol), morpholin-4-amine (85 mg, 0.8 mmol) and HATU (360 mg, 1.5 mmol) were added and the resulting mixture was stirred for 1 h. Water is added and the mixture was diluted with DCM. The aqueous layer was extracted with DCM. The organic layers were combined and dried with magnesium sulfate, filtered and concentrated to give the crude product, which was purified by column chromatography to give 2-(6-(((R)-1-(3-(difluoromethyl)-2-fluorophenyl)ethyl)amino)-5-(1,3-dioxolan-2-yl)-2-methylpyrimidin-4-yl)-2-fluoro-N-morpholinoacetamide (260 mg). LC-MS: m/z 513.8 $[M+H]^+$.

Step 5:

2-(6-(((R)-1-(3-(difluoromethyl)-2-fluorophenyl)ethyl)amino)-5-(1,3-dioxolan-2-yl)-2-methylpyrimidin-4-yl)-2-fluoro-N-morpholinoacetamide (50 mg, 0.1 mmol) was dissolved in 2-propanol (2 mL). An aqueous 5 N HCl solution (100 μL, 0.5 mmol) was added and the resulting mixture stirred for 1 hour at 50° C. until complete conversion of the starting material is observed. The solvent was removed to give the crude product, which was purified by prep-HPLC to give (R)-4-((1-(3-(difluoromethyl)-2-fluorophenyl)ethyl)amino)-8-fluoro-2-methyl-6-morpholinopyrido[4,3-d]pyrimidin-7 (6H)-one (20 mg). LC-MS: m/z 451.8 $[M+H]^+$.

The following compounds have been prepared in analogy to the representative procedures described for example 29.

| ID | Structure | LC-MS: m/z $[M + H]^+$ |
|---|---|---|
| Example 30 | 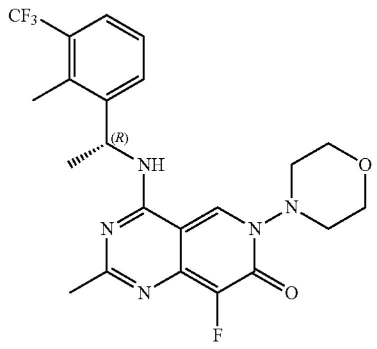 | 465.8 |
| Example 31 | 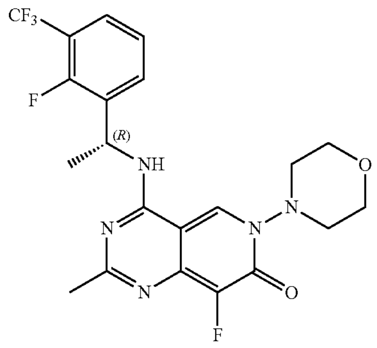 | 469.7 |
| Example 32 | 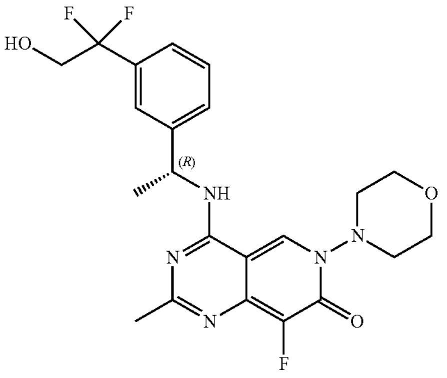 | 463.8 |

-continued

| ID | Structure | LC-MS: m/z $[M + H]^+$ |
| --- | --- | --- |
| Example 33 | 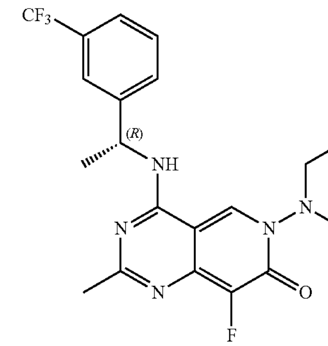 | 451.8 |

Example 34

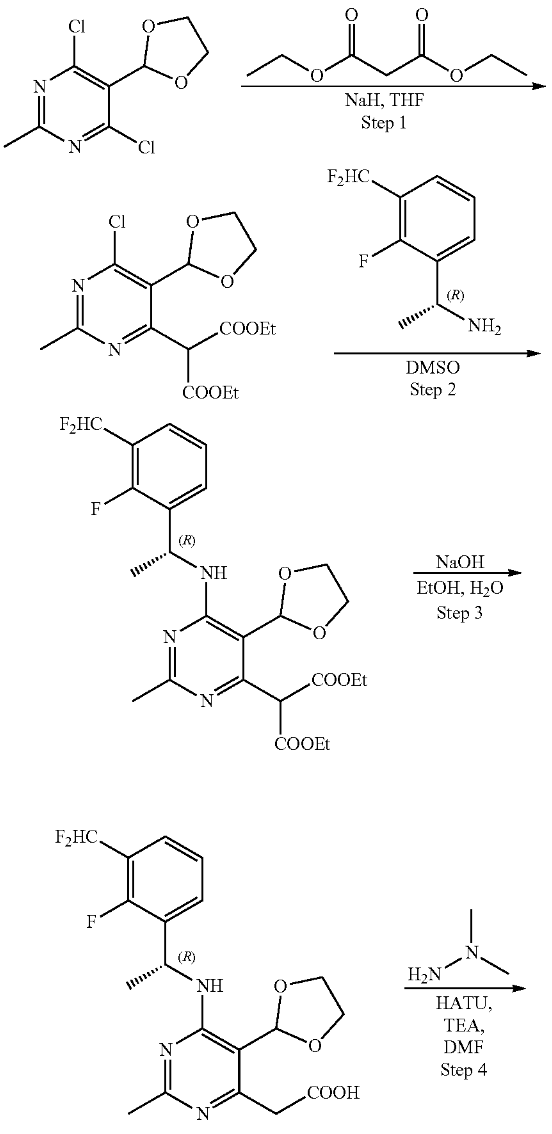

-continued

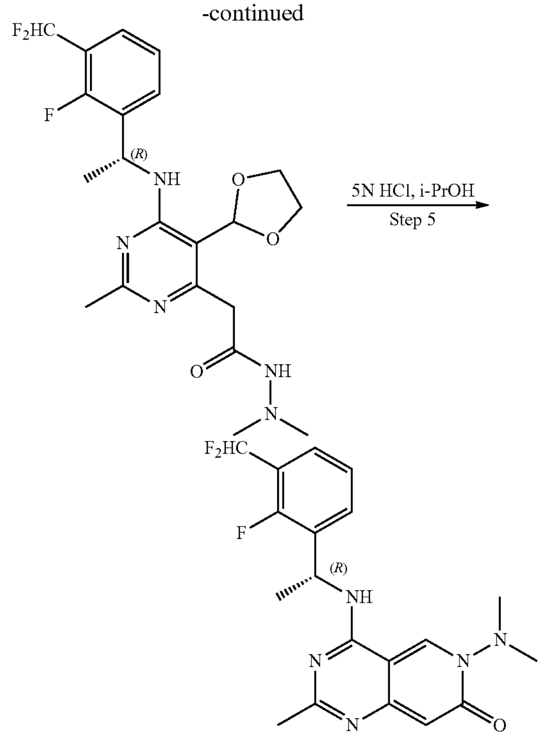

Step 1:

To a solution of diethyl propanedioate (613.2 mg, 3.8 mmol) in THF (15 mL) was added NaH (122.2 mg, 2.5 mmol, 48%) at 0° C. The mixture was stirred at 0° C. for 0.5 hour. Then 4,6-dichloro-5-(1,3-dioxolan-2-yl)-2-methyl-pyrimidine (600 mg, 2.5 mmol) was added. The mixture was stirred at 20° C. for 10 hours. The reaction mixture was quenched with aq. $NH_4Cl$ (20 mL). The mixture was extracted with EtOAc (3x35 mL). The combined organic layer was dried over $Na_2SO_4$, filtered, concentrated and purified by column chromatography on silica gel to afford diethyl 2-[6-chloro-5-(1,3-dioxolan-2-yl)-2-methyl-pyrimidin-4-yl]propanedioate (220 mg, 24% yield) as a light yellow solid.

Step 2:

To a solution of diethyl 2-[6-chloro-5-(1,3-dioxolan-2-yl)-2-methyl-pyrimidin-4-yl]propanedioate (220 mg, 613.2 μmol) and CsF (186.3 mg, 1.23 mmol) in DMSO (6 mL) was added (1R)-1-[3-(difluoromethyl)-2-fluoro-phenyl]ethanamine (116 mg, 613.2 μmol). The mixture was stirred at 120° C. for 5 hours. The mixture was diluted with EtOAc (60 mL) and then washed with brine (4×20 mL). The organic layer was dried over $Na_2SO_4$, filtered, concentrated and purified by column chromatography on silica gel to afford diethyl 2-[6-[[(1R)-1-[3-(difluoromethyl)-2-fluoro-phenyl]ethyl]amino]-5-(1,3-dioxolan-2-yl)-2-methyl-pyrimidin-4-yl]propanedioate (110 mg, 35% yield) as a light yellow solid.

Step 3:

To a solution of diethyl 2-[6-[[(1R)-1-[3-(difluoromethyl)-2-fluoro-phenyl]ethyl]amino]-5-(1,3-dioxolan-2-yl)-2-methyl-pyrimidin-4-yl]propanedioate (70 mg, 136.8 μmol) in water (0.5 mL) and ethanol (2 mL) was added sodium hydroxide (82.1 mg, 410.5 μmol, 20%). The mixture was stirred at 100° C. for 2 hours. The mixture was concentrated. $CH_3OH$ (4 mL) was added and the mixture was filtered. The filtrate was concentrated to afford (R)-2-(6-((1-(3-(difluoromethyl)-2-fluorophenyl)ethyl)amino)-5-(1,3-dioxolan-2-yl)-2-methylpyrimidin-4-yl)acetic acid (100 mg) as a yellow solid which was used for next step directly without further purification.

Step 4:

To a solution of (R)-2-(6-((1-(3-(difluoromethyl)-2-fluorophenyl)ethyl)amino)-5-(1,3-dioxolan-2-yl)-2-methylpyrimidin-4-yl)acetic acid (30 mg, 69 μmol) TEA (17.8 mg, 138.1 μmol) and HATU (52.8 mg, 138.1 μmol) in DMF (1.5 mL) was added isopropyl hydrazine (15.3 mg, 138.1 μmol). The mixture was stirred at 20° C. for 0.5 hour. The mixture was diluted with EtOAc (60 mL) and then washed with brine (20 mL). The organic layer was dried over $Na_2SO_4$, filtered, concentrated and purified by column chromatography on silica gel to afford 2-[6-1[[(1R)-1-[3-(difluoromethyl)-2-fluoro-phenyl]ethyl]amino]-5-(1,3-dioxolan-2-yl)-2-methyl-pyrimidin-4-yl]-N',N'-dimethyl-acetohydrazide (10 mg) as a yellow solid.

Step 5:

To a solution of 2-[6-[[(1R)-1-[3-(difluoromethyl)-2-fluoro-phenyl]ethyl]amino]-5-(1,3-dioxolan-2-yl)-2-methyl-pyrimidin-4-yl]-N',N'-dimethyl-acetohydrazide (10 mg, 22 μmol) in i-PrOH (2 mL) was added HCl (5 N, 10 μL). The mixture was stirred at 50° C. for 1 hour. The mixture was concentrated and purified by prep-HPLC to afford 4-[[(1R)-1-[3-(difluoromethyl)-2-fluoro-phenyl]ethyl]amino]-6-(dimethylamino)-2-methyl-pyrido[4,3-d]pyrimidin-7-one (1.2 mg, 14% yield) as a light yellow solid. LC-MS: m/z 391.8 $[M+H]^+$.

The following compounds have been prepared in analogy to the representative procedures described for example 34.

| ID | Structure | LC-MS: m/z $[M + H]^+$ |
| --- | --- | --- |
| Example 35 | 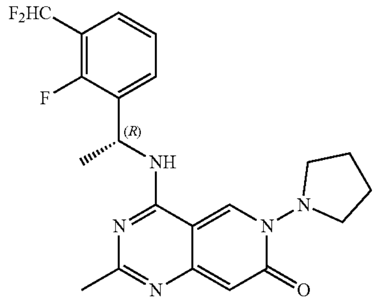 | 417.8 |
| Example 36 | 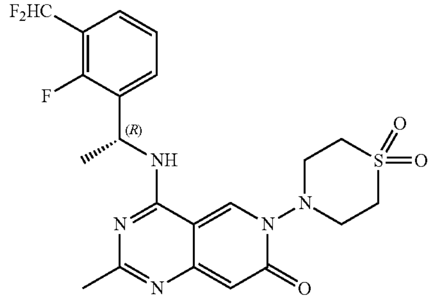 | 481.7 |
| Example 37 | 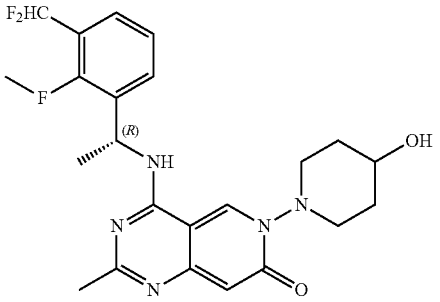 | 447.8 |

-continued
| ID | Structure | LC-MS: m/z [M + H]+ |
|---|---|---|
| Example 38 | 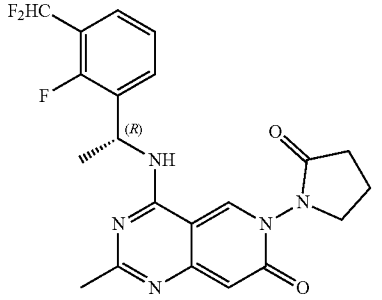 | 431.8 |
| Example 39 | 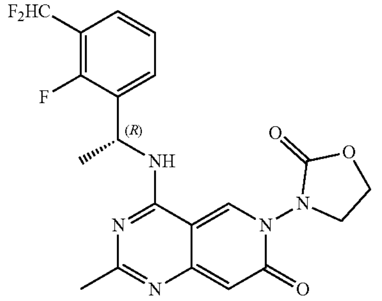 | 433.7 |
| Example 86 | 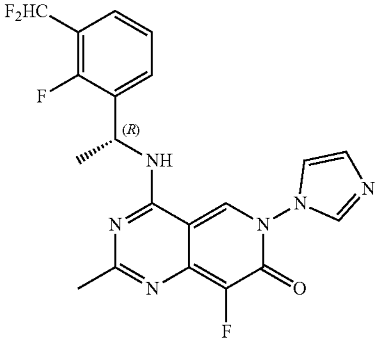 | 432.8 |
| Example 87 | 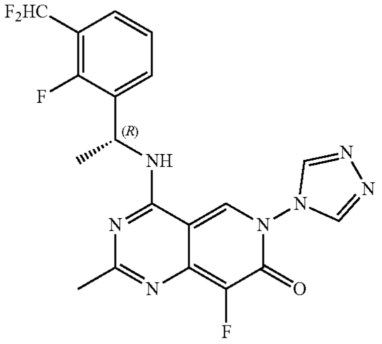 | 433.8 |

Example 40

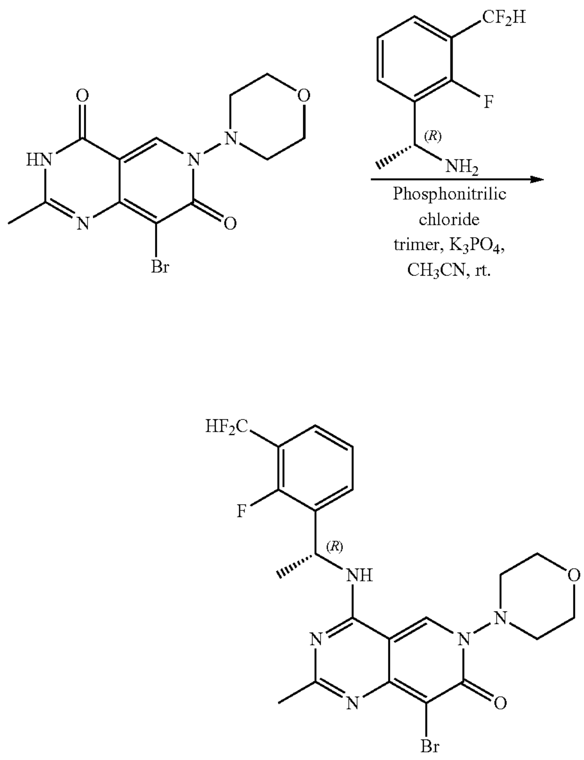

A mixture of 8-bromo-2-methyl-6-morpholino-3H-pyrido [4,3-d]pyrimidine-4,7-dione (25 mg, 73.3 μmol), 2,2,4,4,6,6-hexachloro-1,3,5-triaza-2,4,6triphosphacyclohexa-1,3,5-triene (25.5 mg, 73.3 μmol) and potassium phosphate (38.9 mg, 183.2 μmol) in $CH_3CN$ (8 mL) was stirred at room temperature for 3 hours. (1R)-1-[3-(difluoromethyl)-2-fluoro-phenyl]ethanamine (13.9 mg, 73.3 μmol) was added. The mixture was stirred for 3 hours. The reaction mixture was concentrated and purified by flash column chromatography to give 8-bromo-4-[[(1R)-1-[3-(difluoromethyl)-2-fluoro-phenyl]ethyl]amino]-2-methyl-6-morpholino-pyrido [4,3-d]pyrimidin-7-one (25 mg, 67% yield). LC-MS: m/z 511.7 $[M+H]^+$.

Example 41

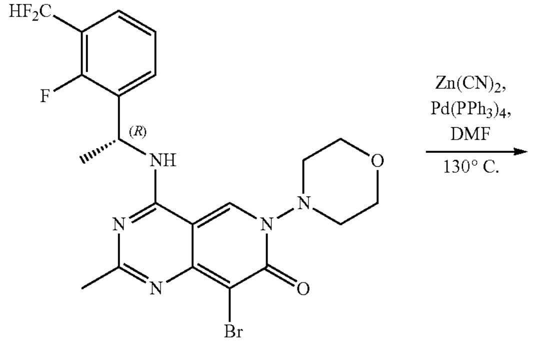

-continued

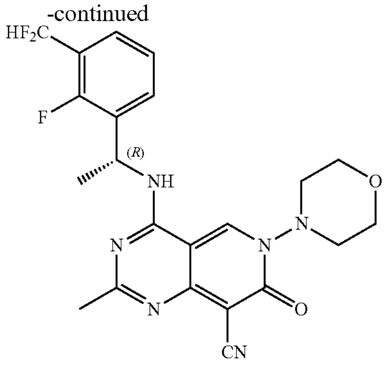

A mixture of zinc dicyanide (23.5 mg, 200 μmol) and 8-bromo-4-[[(1R)-1-[3-(difluoromethyl)-2-fluoro-phenyl] ethyl]amino]-2-methyl-6-morpholino-pyrido[4,3-d]pyrimidin-7-one (25.6 mg, 50 μmol) in DMF (3 mL) was stirred at 130° C. in a microwave reactor for 2 hours. The mixture was diluted with EA (100 mL) and water (15 mL). The organic phase was washed with brine (3×20 mL), dried over $Na_2SO_4$, filtered, concentrated and purified by prep-HPLC to give 4-[[(1R)-1-[3-(difluoromethyl)-2-fluoro-phenyl] ethyl]amino]-2-methyl-6-morpholino-7-oxo-pyrido[4,3-d] pyrimidine-8-carbonitrile (2 mg, 9% yield). LC-MS: m/z 458.8 $[M+H]^+$.

Example 42

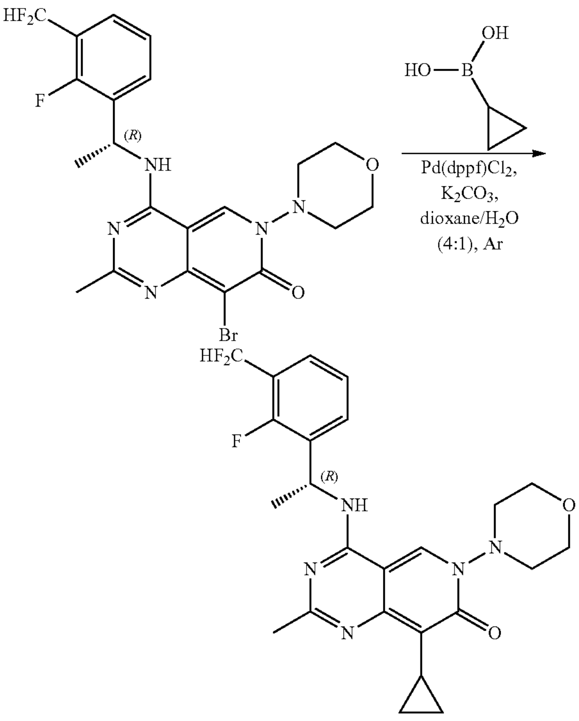

A mixture of 8-bromo-4-[[(1R)-1-[3-(difluoromethyl)-2-fluoro-phenyl]ethyl]amino]-2-methyl-6-morpholino-pyrido [4,3-d]pyrimidin-7-one (51.2 mg, 99.9 μmol), cyclopropylboronic acid (12.9 mg, 149.9 μmol), $Pd(dppf)Cl_2$ (8.2 mg, 10 μmol) and $K_2CO_3$ (27.6 mg, 199.9 μmol) in dioxane (8 mL) was stirred at 100° C. for 6 hours under Ar. The mixture was diluted with DCM (150 mL) and $H_2O$ (20 mL). The organic phase was dried over $Na_2SO_4$, filtered, concentrated and purified by prep-HPLC to give 8-cyclopropyl-4-[[(1R)-1-[3-(difluoromethyl)-2-fluoro-phenyl]ethyl]amino]-2-methyl-6-morpholino-pyrido[4,3-d]pyrimidin-7-one (7 mg, 15% yield). LC-MS: m/z 473.8 $[M+H]^+$.

Example 43

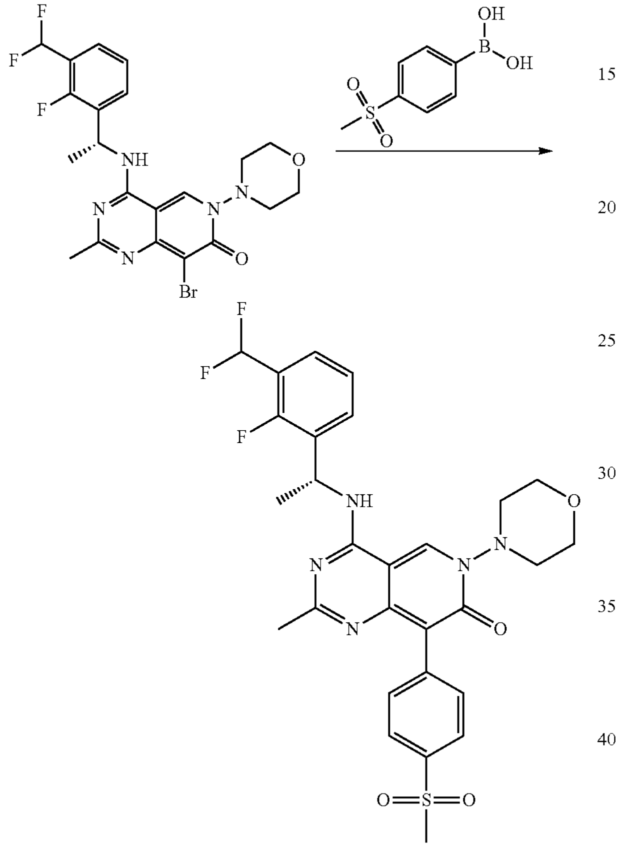

To a mixture of 8-bromo-4-[[(1R)-1-[3-(difluoromethyl)-2-fluoro-phenyl]ethyl]amino]-2-methyl-6-morpholino-pyrido[4,3-d]pyrimidin-7-one (30 mg, 58 μmol), (4-methylsulfonylphenyl)boronic acid (15 mg, 75 μmol) and cesium carbonate (60 mg, 184 μmol) in dioxane (2 mL) and water (0.5 mL) was added Pd(dppf)$Cl_2$-DCM (5 mg, 6 μmol) under nitrogen. The reaction was stirred at 100° C. for 1 hour. The mixture was diluted with water (50 mL) and extracted with EtOAc (3×30 mL). The combined organic layer was washed with brine (50 mL), dried over $Na_2SO_4$, filtered and concentrated. The residue was purified by flash chromatography on silica gel eluting with 0-8% MeOH in DCM to afford 4-[[(1R)-1-[3-(difluoromethyl)-2-fluoro-phenyl]ethyl]amino]-2-methyl-8-(4-methylsulfonylphenyl)-6-morpholino-pyrido[4,3-d]pyrimidin-7-one (2.1 mg, 6% yield) as a light yellow solid. LC-MS: m/z 587.6 $[M+H]^+$.

The following compounds have been prepared in analogy to the representative procedures described for example 42 and example 43.

| ID | Structure | LC-MS: m/z $[M + H]^+$ |
|---|---|---|
| Example 44 | 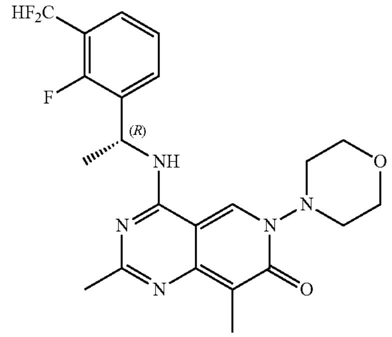 | 447.8 |
| Example 45 | 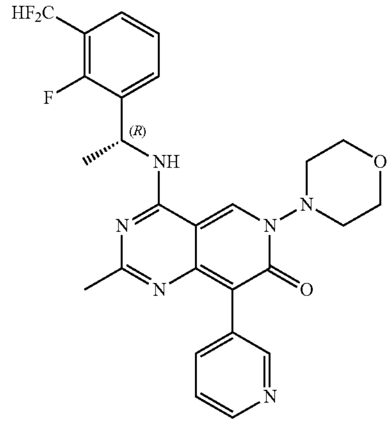 | 510.7 |
| Example 46 | 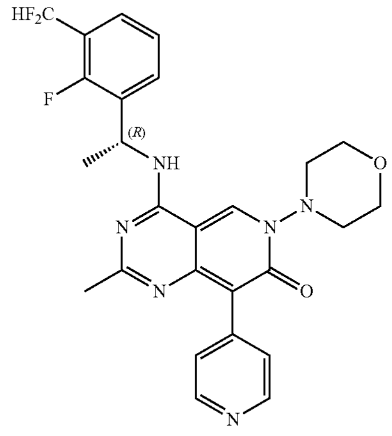 | 510.8 |

-continued
| ID | Structure | LC-MS: m/z [M + H]$^+$ |
|---|---|---|
| Example 47 | 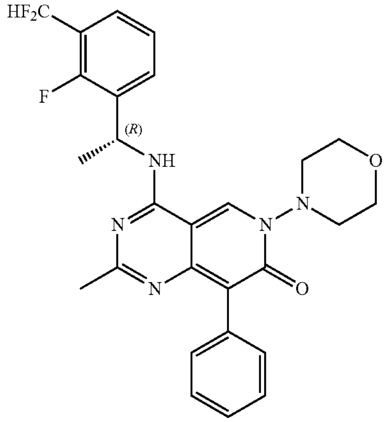 | 509.7 |
| Example 48 | 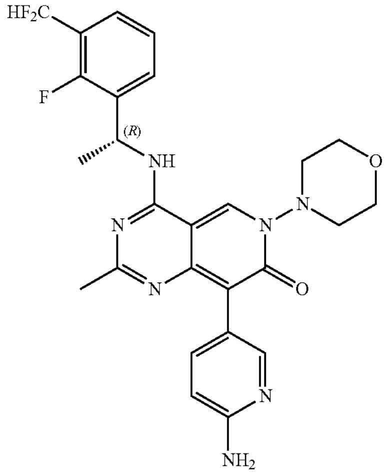 | 525.7 |
| Example 49 | 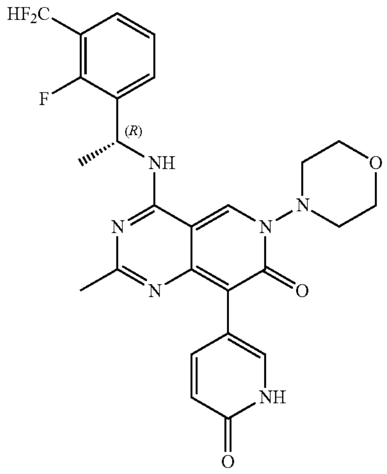 | 526.7 |
| Example 50 | 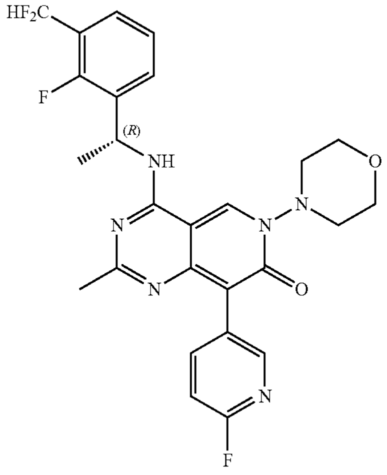 | 528.7 |
| Example 51 | 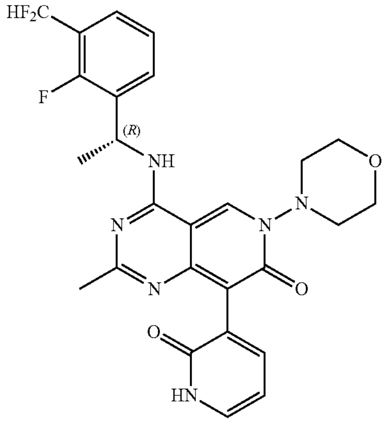 | 526.7 |
| Example 52 | 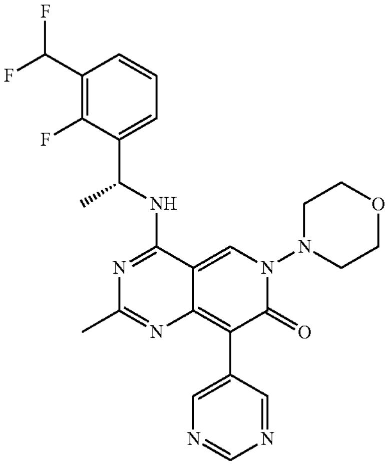 [SMILES: Cc1nc(N[C@H](C)c2cccc(C(F)F)c2F)c2cn(N3CCOCC3)c(=O)c(-c3cncnc3)c2n1] | 511.7 |

-continued
| ID | Structure | LC-MS: m/z [M + H]+ |
|---|---|---|
| Example 53 | 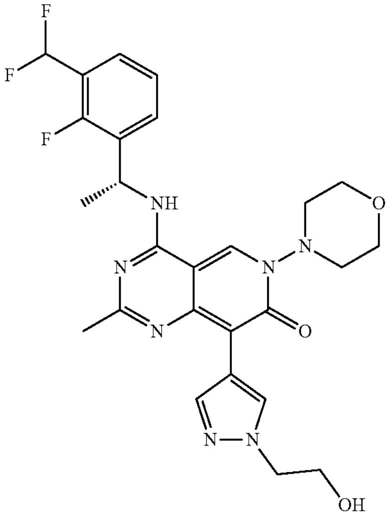 [SMILES: Cc1nc(N[C@H](C)c2cccc(C(F)F)c2F)c2cn(N3CCOCC3)c(=O)c(-c3cnn(CCO)c3)c2n1] | 543.7 |
| Example 54 | 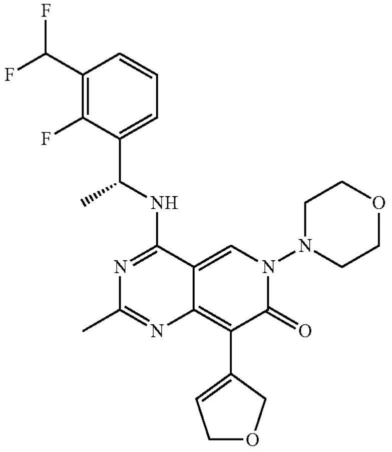 [SMILES: Cc1nc(N[C@H](C)c2cccc(C(F)F)c2F)c2cn(N3CCOCC3)c(=O)c(C3=CCOC3)c2n1] | 501.7 |
| Example 55 | 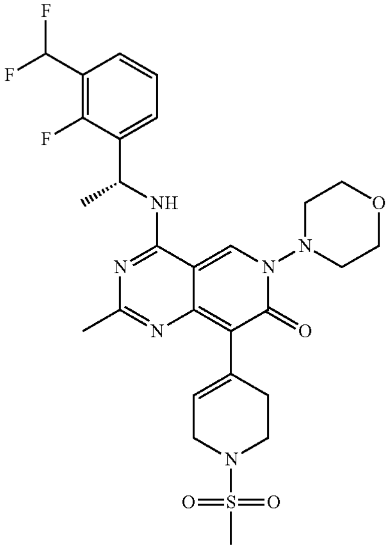 [SMILES: Cc1nc(N[C@H](C)c2cccc(C(F)F)c2F)c2cn(N3CCOCC3)c(=O)c(C3=CCN(S(C)(=O)=O)CC3)c2n1] | 592.7 |
-continued
| ID | Structure | LC-MS: m/z [M + H]+ |
|---|---|---|
| Example 56 | 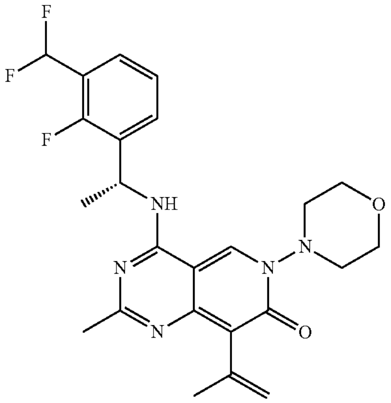 [SMILES: C=C(C)c1c(=O)n(N2CCOCC2)cc2c(N[C@H](C)c3cccc(C(F)F)c3F)nc(C)nc12] | 473.8 |
| Example 57 | 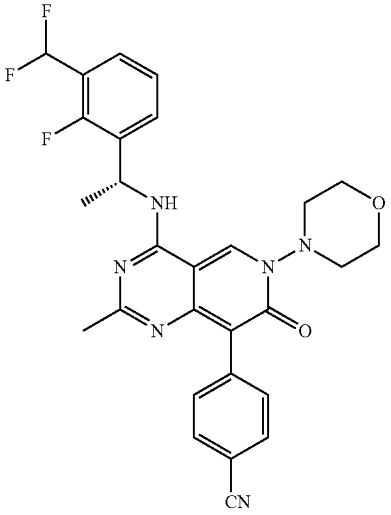 [SMILES: Cc1nc(N[C@H](C)c2cccc(C(F)F)c2F)c2cn(N3CCOCC3)c(=O)c(-c3ccc(C#N)cc3)c2n1] | 534.9 |
| Example 58 | 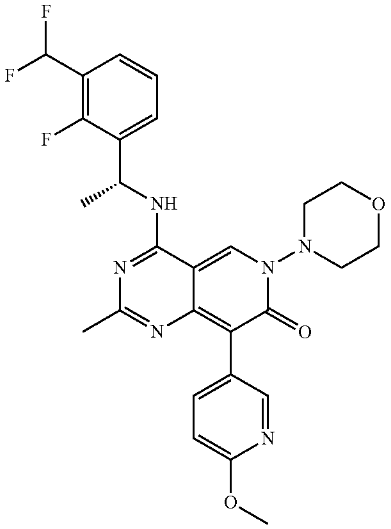 [SMILES: COc1ccc(-c2c(=O)n(N3CCOCC3)cc3c(N[C@H](C)c4cccc(C(F)F)c4F)nc(C)nc23)cn1] | 540.8 |

-continued
| ID | Structure | LC-MS: m/z [M + H]+ |
|---|---|---|
| Example 59 | 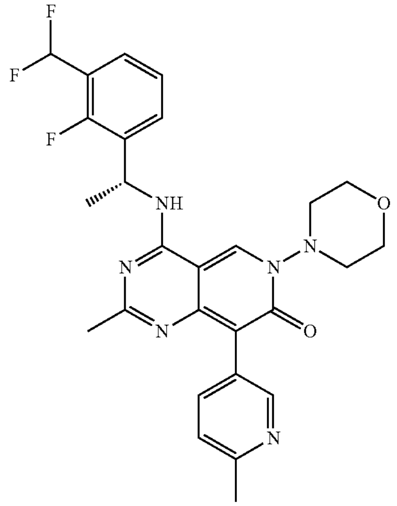 [SMILES: Cc1ccc(-c2c(=O)n(N3CCOCC3)cc3c(N[C@H](C)c4cccc(C(F)F)c4F)nc(C)nc23)cn1] | 524.8 |
| Example 60 | 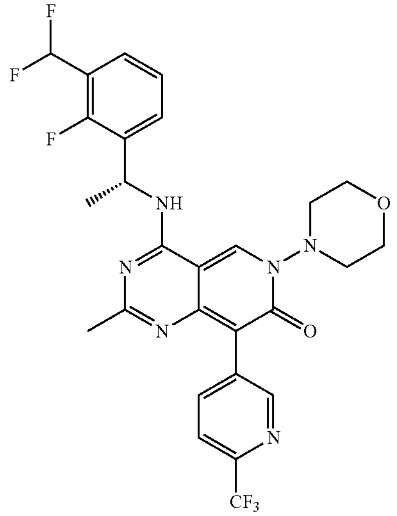 [SMILES: Cc1nc(N[C@H](C)c2cccc(C(F)F)c2F)c2cn(N3CCOCC3)c(=O)c(-c3ccc(C(F)(F)F)nc3)c2n1] | 578.9 |
| Example 61 | 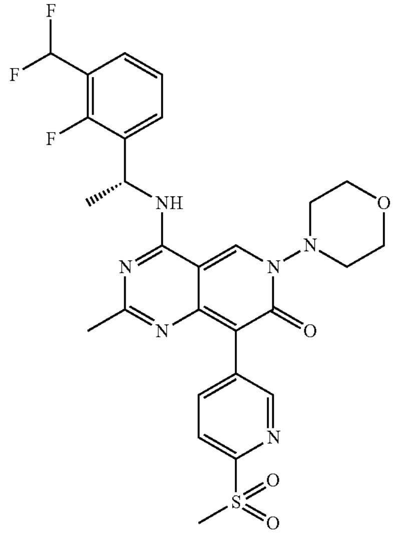 [SMILES: Cc1nc(N[C@H](C)c2cccc(C(F)F)c2F)c2cn(N3CCOCC3)c(=O)c(-c3ccc(S(C)(=O)=O)nc3)c2n1] | 588.9 |
-continued
| ID | Structure | LC-MS: m/z [M + H]+ |
|---|---|---|
| Example 62 | 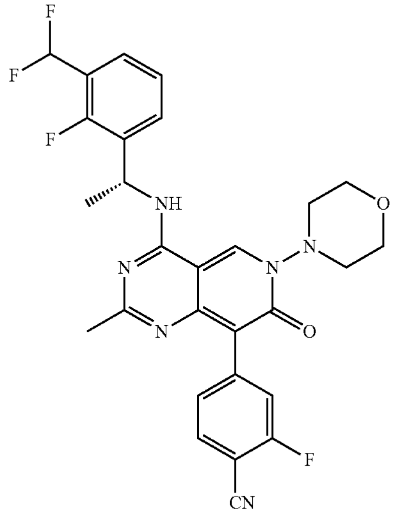 | 552.8 |
| Example 63 | 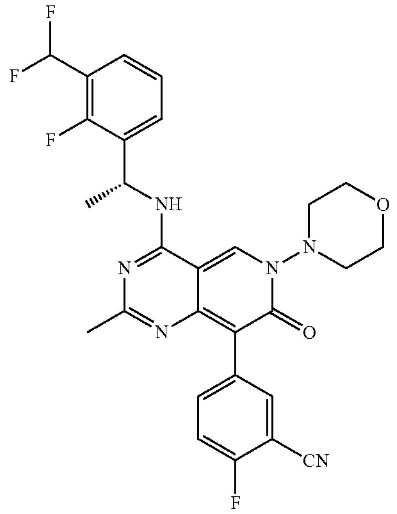 [SMILES: Cc1nc(N[C@H](C)c2cccc(C(F)F)c2F)c2cn(N3CCOCC3)c(=O)c(-c3ccc(F)c(C#N)c3)c2n1] | 552.8 |
| Example 64 | 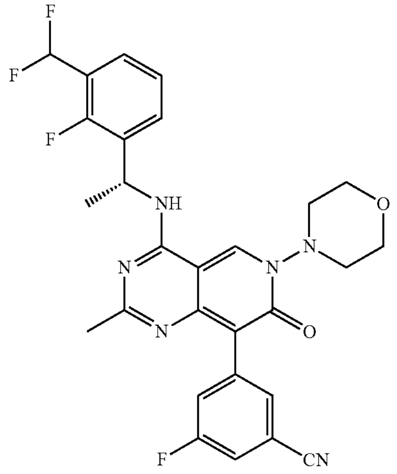 [SMILES: Cc1nc(N[C@H](C)c2cccc(C(F)F)c2F)c2cn(N3CCOCC3)c(=O)c(-c3cc(F)cc(C#N)c3)c2n1] | 552.8 |

-continued
| ID | Structure | LC-MS: m/z [M + H]$^+$ |
| --- | --- | --- |
| Example 65 | 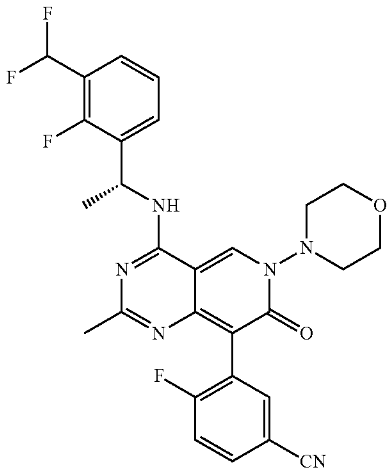 [SMILES: Cc1nc(N[C@H](C)c2cccc(C(F)F)c2F)c2cn(N3CCOCC3)c(=O)c(-c3cc(C#N)ccc3F)c2n1] | 552.8 |
| Example 66 | 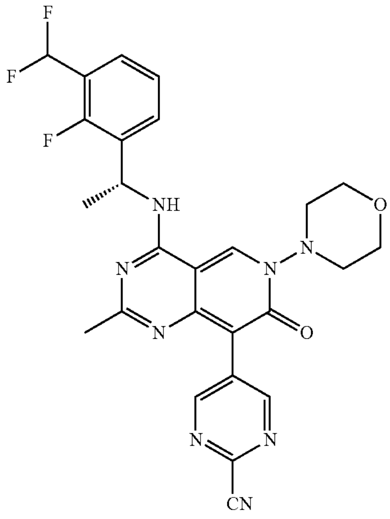 [SMILES: Cc1nc(N[C@H](C)c2cccc(C(F)F)c2F)c2cn(N3CCOCC3)c(=O)c(-c3cnc(C#N)nc3)c2n1] | 536.9 |
| Example 67 | 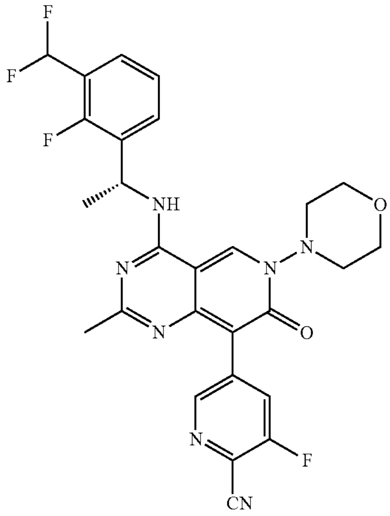 [SMILES: Cc1nc(N[C@H](C)c2cccc(C(F)F)c2F)c2cn(N3CCOCC3)c(=O)c(-c3cnc(C#N)c(F)c3)c2n1] | 553.8 |
-continued
| ID | Structure | LC-MS: m/z [M + H]$^+$ |
| --- | --- | --- |
| Example 68 | 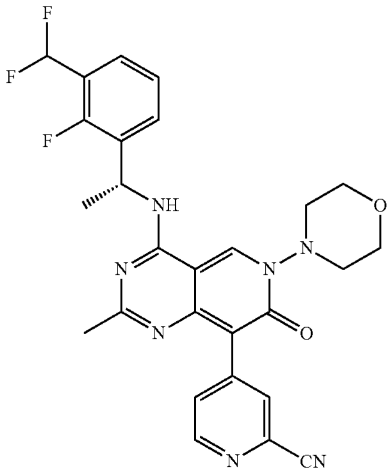 [SMILES: Cc1nc(N[C@H](C)c2cccc(C(F)F)c2F)c2cn(N3CCOCC3)c(=O)c(-c3ccnc(C#N)c3)c2n1] | 535.9 |
| Example 69 | 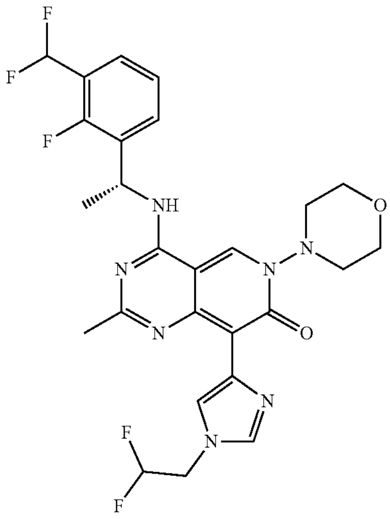 [SMILES: Cc1nc(N[C@H](C)c2cccc(C(F)F)c2F)c2cn(N3CCOCC3)c(=O)c(-c3cn(CC(F)F)cn3)c2n1] | 563.9 |
| Example 70 | 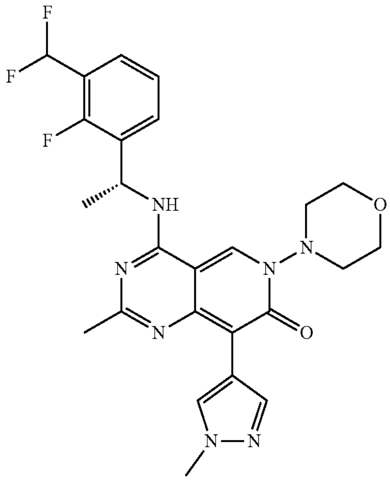 [SMILES: Cc1nc(N[C@H](C)c2cccc(C(F)F)c2F)c2cn(N3CCOCC3)c(=O)c(-c3cnn(C)c3)c2n1] | 513.9 |

-continued
| ID | Structure | LC-MS: m/z $[M + H]^+$ |
|---|---|---|
| Example 71 | 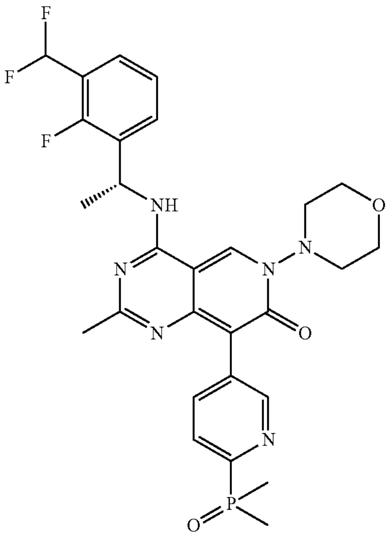 [SMILES: Cc1nc(N[C@H](C)c2cccc(C(F)F)c2F)c2cn(N3CCOCC3)c(=O)c(-c3ccc(P(C)(C)=O)nc3)c2n1] | 586.9 |
| Example 72 | 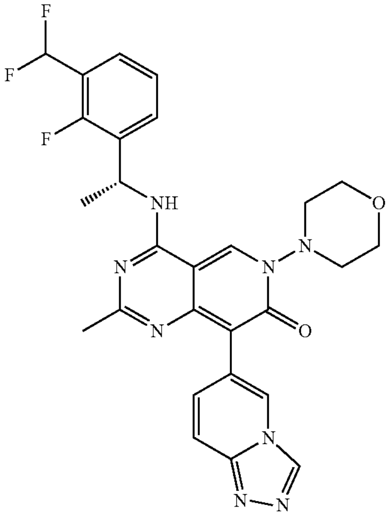 [SMILES: Cc1nc(N[C@H](C)c2cccc(C(F)F)c2F)c2cn(N3CCOCC3)c(=O)c(-c3ccc4nncn4c3)c2n1] | 550.8 |
| Example 73 | 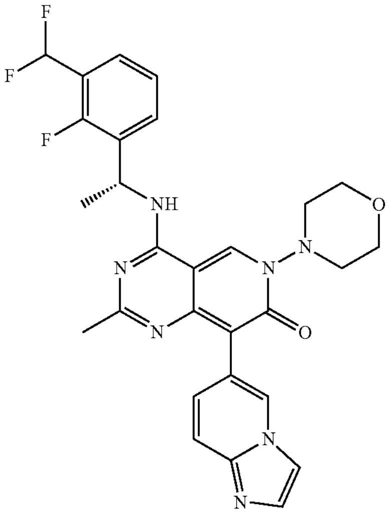 | 549.9 |
-continued
| ID | Structure | LC-MS: m/z $[M + H]^+$ |
|---|---|---|
| Example 78 | 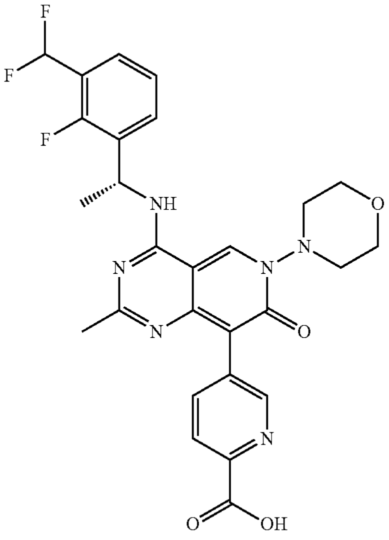 [SMILES: Cc1nc(N[C@H](C)c2cccc(C(F)F)c2F)c2cn(N3CCOCC3)c(=O)c(-c3ccc(C(=O)O)nc3)c2n1] | 554.8 |
| Example 79 | 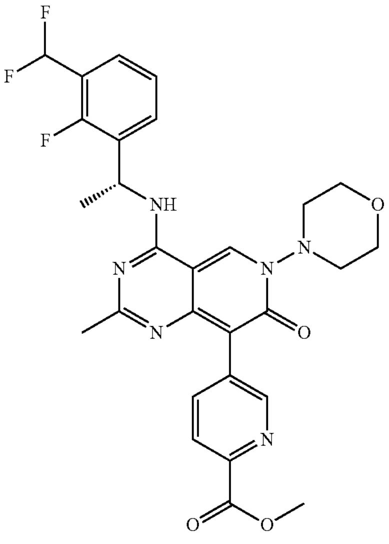 [SMILES: COC(=O)c1ccc(-c2c(=O)n(N3CCOCC3)cc3c(N[C@H](C)c4cccc(C(F)F)c4F)nc(C)nc23)cn1] | 568.9 |

-continued
| ID | Structure | LC-MS: m/z [M + H]+ |
|---|---|---|
| Example 80 | 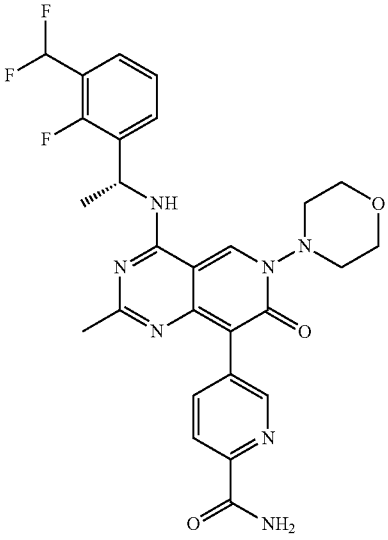 [SMILES: Cc1nc(N[C@H](C)c2cccc(C(F)F)c2F)c2cn(N3CCOCC3)c(=O)c(-c3ccc(C(N)=O)nc3)c2n1] | 553.9 |
| Example 81 | 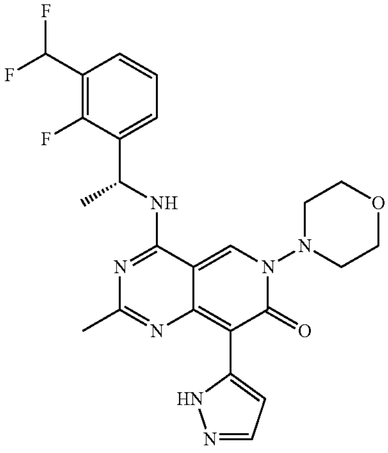 [SMILES: Cc1nc(N[C@H](C)c2cccc(C(F)F)c2F)c2cn(N3CCOCC3)c(=O)c(-c3ccn[nH]3)c2n1] | 499.9 |
| Example 84 | 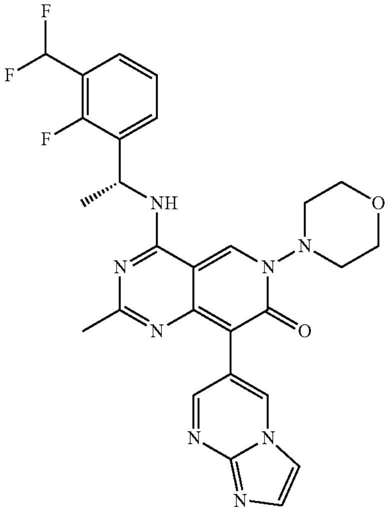 [SMILES: Cc1nc(N[C@H](C)c2cccc(C(F)F)c2F)c2cn(N3CCOCC3)c(=O)c(-c3cnc4nccn4c3)c2n1] | 550.9 |
| Example 85 | 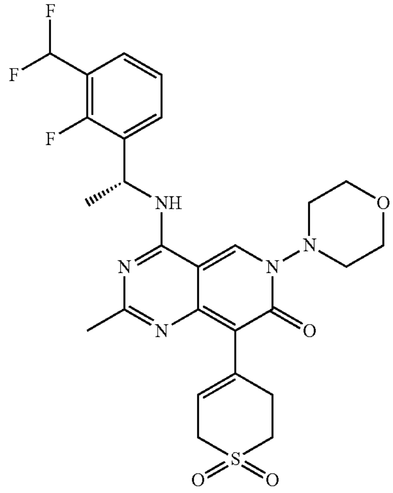 [SMILES: Cc1nc(N[C@H](C)c2cccc(C(F)F)c2F)c2cn(N3CCOCC3)c(=O)c(C3=CCS(=O)(=O)CC3)c2n1] | 563.9 |
Example 74
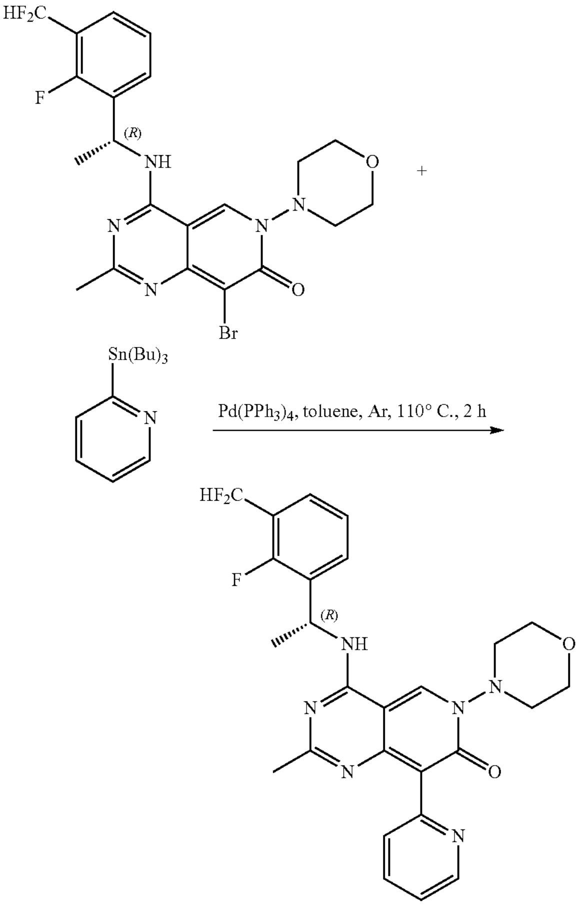
A mixture of 8-bromo-4-[[(1R)-1-[3-(difluoromethyl)-2-fluoro-phenyl]ethyl]amino]-2-methyl-6-morpholino-pyrido

[4,3-d]pyrimidin-7-one (30 mg, 59 t mol), 2-(tributylstannyl)pyridine (32 mg, 88 μmol) and $Pd(PPh_3)_4$(14 mg, 12 μmol) in toluene (6 mL) was stirred at 110° C. for 2 hours under Ar. The mixture was diluted with EA (150 mL) and $H_2O$ (20 mL). The organic phase was dried over $Na_2SO_4$, filtered, concentrated and purified by prep-HPLC to give (R)-4-((1-(3-(difluoromethyl)-2-fluorophenyl)ethyl)amino)-2-methyl-6-morpholino-8-(pyridin-2-yl)pyrido[4,3-d]pyrimidin-7(6H)-one (2.5 mg, 8% yield) as a yellow solid. LC-MS: m/z 510.7 $[M+H]^+$.

Example 75

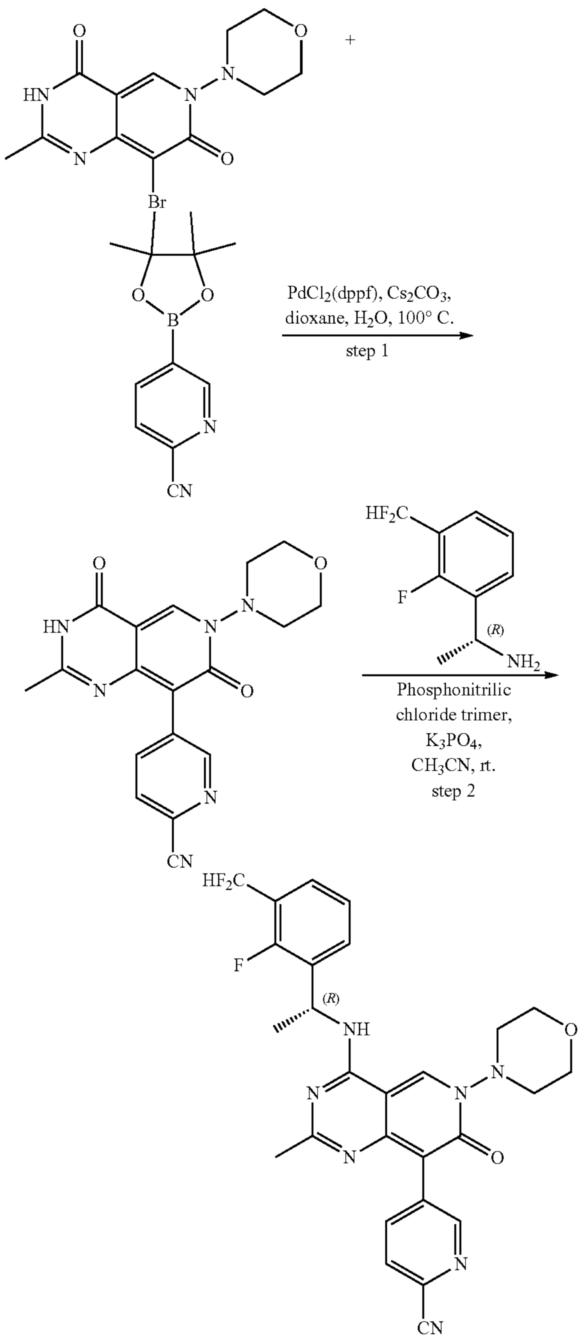

Step 1:

A mixture of 8-bromo-2-methyl-6-morpholinopyrido[4,3-d]pyrimidine-4,7(3H,6H)-dione (136.4 mg, 0.4 mmol), 5-(4,4,5,5-tetramethyl-1,3,2-dioxaborolan-2-yl)picolinonitrile (138.0 mg, 0.6 mmol), $Pd(dppf)Cl_2$ (74 mg, 0.1 mmol) and $Cs_2CO_3$ (260.0 mg, 0.8 mmol) in dioxane (10 mL) and water (2 mL) was stirred at 100° C. for 5 hours under Ar. The mixture was diluted with DCM (150 mL) and water (10 mL). The organic phase was dried over $Na_2SO_4$, filtered, concentrated and purified by flash column chromatography to give 5-(2-methyl-6-morpholino-4,7-dioxo-3,4,6,7-tetrahydropyrido[4,3-d]pyrimidin-8-yl)picolinonitrile (110 mg, 75% yield). LC-MS: m/z 364.8 $[M+H]^+$.

Step 2:

A mixture of 5-(2-methyl-6-morpholino-4,7-dioxo-3,4,6,7-tetrahydropyrido[4,3-d]pyrimidin-8-yl)picolinonitrile (36.4 mg, 0.1 mmol), $K_3PO_4$ (63.6 mg, 0.3 mmol) and phosphonitrilic chloride trimer (34.8 mg, 0.1 mmol) in $CH_3CN$ (10 mL) was stirred at room temperature for 3 hours. (R)-1-(3-(difluoromethyl)-2-fluorophenyl)ethan-1-amine (18.9 mg, 0.1 mmol) was added and the mixture was stirred at 80° C. for 2 hours. The solvent was removed. DCM (150 mL) and water (20 mL) was added. The mixture was stirred for 10 min. The organic phase was dried over $Na_2SO_4$, filtered, concentrated and purified by prep-HPLC to give (R)-5-(4-((1-(3-(difluoromethyl)-2-fluorophenyl)ethyl)amino)-2-methyl-6-morpholino-7-oxo-6,7-dihydropyrido[4,3-]pyrimidin-8-yl)picolinonitrile (15 mg, 28% yield). LC-MS: m/z 535.7 $[M+H]^+$.

The following compounds have been prepared in analogy to the representative procedures described for example 75.

| ID | Structure | LC-MS m/z $[M + H]^+$ |
|---|---|---|
| Example 76 | 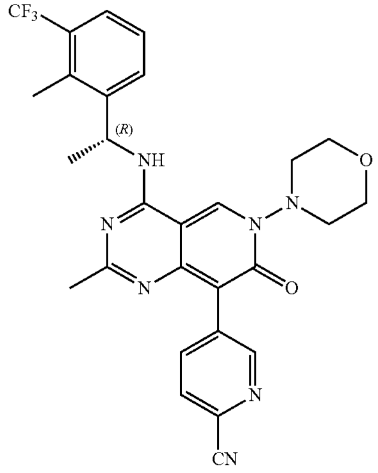 | 549.7 |

-continued

| ID | Structure | LC-MS m/z $[M + H]^+$ |
|---|---|---|
| Example 82 | 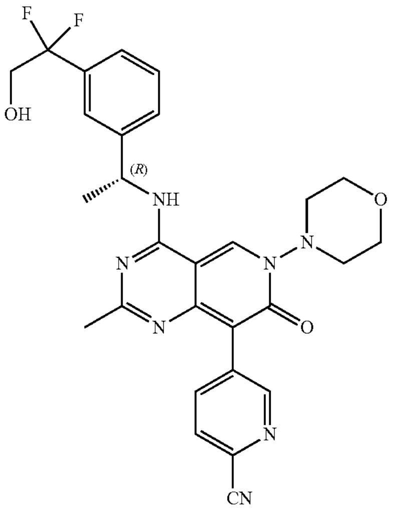 | 547.9 |
| Example 83 | 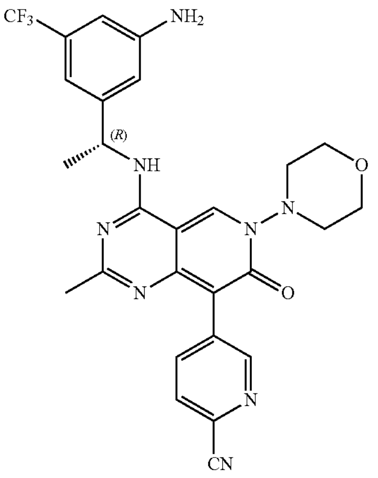 | 550.9 |

Example 77

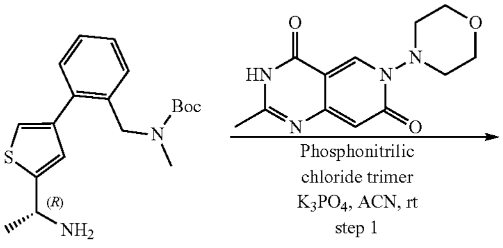

-continued

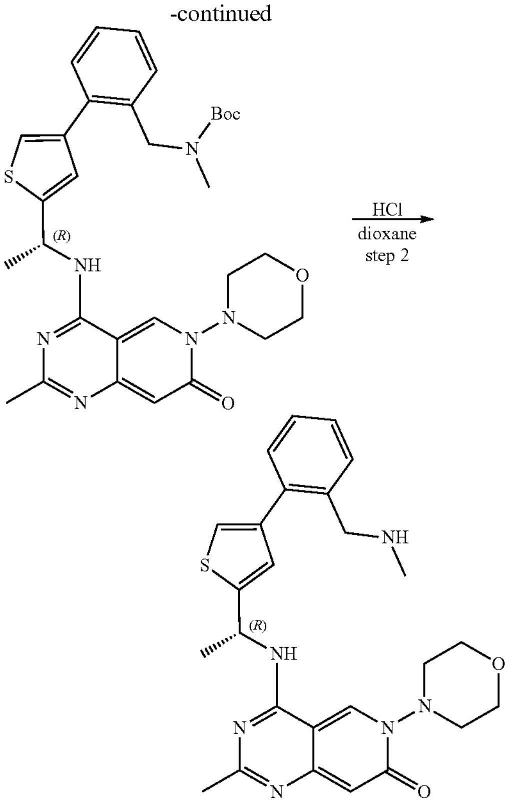

Step 1:

A mixture of 2-methyl-6-morpholino-3H-pyrido[4,3-d] pyrimidine-4,7-dione (16 mg, 61 μmol), phosphonitrilic chloride trimer (21.2 mg, 61 μmol) and $K_3PO_4$ (32.3 mg, 152.5 μmol) in $CH_3CN$ (3 mL) was stirred at room temperature for 3 hours. Tert-butyl N-[[2-[5-[(1R)-1-amino-ethyl]-3-thienyl]phenyl]methyl]-N-methyl-carbamate (23.3 mg, 67.1 μmol) was added. The mixture was stirred for 3 hours. The reaction mixture was concentrated and purified by prep-HPLC to give tert-butyl N-methyl-N-[[2-[5-[(1R)-1-[(2-methyl-6-morpholino-7-oxo-pyrido[4,3-d]pyrimidin-4-yl)amino]ethyl]-3-thienyl]phenyl]methyl]carbamate (5 mg, 14% yield). LC-MS: m/z 590.8 $[M+H]^+$.

Step 2:

To a stirred solution of tert-butyl N-methyl-N-[[2-[5-[(1R)-1-[(2-methyl-6-morpholino-7-oxo-pyrido[4,3-d]pyrimidin-4-yl)amino]ethyl]-3-thienyl]phenyl]methyl]carbamate (5 mg, 8.5 μmol) in dioxane (1 mL) was added 4 N HCl in dioxane (3 mL). The mixture was stirred at room temperature for 1 h. The reaction mixture was concentrated, basified by 1 N $NaHCO_3$(aq.), extracted with DCM (30 mL), dried over $Na_2SO_4$, filtered, concentrated and purified by prep-HPLC to give 2-methyl-4-[[(1R)-1-[4-[2-(methylaminomethyl)phenyl]-2-thienyl]ethyl]amino]-6-morpholino-pyrido[4,3-d]pyrimidin-7-one (1.5 mg, 36% yield). LC-MS: m/z 490.8 $[M+H]^+$.

Example 3. Biological Assays a. KRAS::SOS1 AlphaScreen Binding Assay

This assay is used to examine the potency with which compounds inhibit the protein protein interaction between SOS1 and KRAS G12D in a defined biochemical setting. Low $IC_{50}$ values of given compounds are indicative of high potency of the SOS1 inhibitor compounds in this assay setting.

Reagents:

GST-TEV-SOS1 (564-1049) and His-TEV-Avi-KRAS G12D (1-169) are purchased from Viva Biotech (Shanghai) Ltd.

GDP (Sigma, Cat. G7127)

AlphaLISA Glutathione Acceptor Beads (PerkinElmer, Cat. AL109C)

AlphaScreen Streptavidin Donor Beads (PerkinElmer, Cat. 6760002S)

Assay plates: ProxiPlate-384 Plus, White 384-shallow well Microplate (PerkinElmer, Cat. 6008280)

Assay Buffer:

PBS, pH 7.4 (Gibco, Cat. 10010023)

0.05% Tween 20 (Sigma, Cat. P7949—100 ML)

0.1% Bovine Serum Albumin (BSA) (Sigma, Cat. A1933—5 G)

Assay Protocol:

SOS1 inhibitor compounds are diluted to a final start concentration of 1 PM. Serial dilutions of compounds are made using Tecan D300e Digital Dispenser in 9 concentrations with serial 1:3 dilutions. 100 nL of compound solution is transferred to the 384-well assay plate per well, covering a range between 1 μM and 0.15 nM minimum in duplicate. 10 nM (final assay concentration) KRAS G12D, 5 nM (final assay concentration) SOS1 and 10 μM (final assay concentration) GDP are mixed in assay buffer, and 5 μL of KRAS::SOS1 GDP mix is added into the assay plate to the 100 nL of compound solution (final dilution in the assay 1:100, final DMSO concentration 1%). After a 30 min incubation, AlphaLISA Glutathione Acceptor Beads and AlphaScreen Streptavidin Donor Beads are mixed in assay buffer at a concentration of 5 g/mL (final assay concentration), and 5 μL of bead mix is added into the assay plate. Plates are kept at room temperature in a darkened incubator for 3 h. After a 3 h incubation, the signal is determined using Envision (PerkinElmer). The excitation wavelength is 680 nm, and emission 615 nm. $IC_{50}$ values are calculated and analyzed using GraphPad Prism.

Compound $IC_{50}$ Values in KRAS::SOS1 AlphaScreen Binding Assay

| Example # | KRAS::SOS1 $IC_{50}$ A: ≤0.015 μM B: ≤0.15 μM C: ≤1 μM D: >1 μM | Example # | KRAS::SOS1 $IC_{50}$ A: ≤0.015 μM B: ≤0.15 μM C: ≤1 μM D: >1 μM |
|---|---|---|---|
| Example 1 | A | Example 40 | A |
| Example 2 | A | Example 41 | B |
| Example 3 | A | Example 42 | A |
| Example 4 | B | Example 43 | A |
| Example 5 | A | Example 44 | A |
| Example 6 | A | Example 45 | A |
| Example 7 | A | Example 46 | A |
| Example 8 | A | Example 47 | A |
| Example 9 | A | Example 48 | A |
| Example 10 | A | Example 49 | A |
| Example 11 | A | Example 50 | A |
| Example 12 | A | Example 51 | A |
| Example 13 | A | Example 52 | A |
| Example 14 | A | Example 53 | A |
| Example 15 | B | Example 54 | A |
| Example 16 | B | Example 55 | A |
| Example 17 | A | Example 56 | A |
| Example 18 | A | Example 57 | A |
| Example 19 | A | Example 58 | A |
| Example 20 | A | Example 59 | A |
| Example 21 | A | Example 60 | B |
| Example 22 | C | Example 61 | A |
| Example 23 | D | Example 62 | B |
| Example 24 | B | Example 63 | B |

-continued

Compound $IC_{50}$ Values in KRAS::SOS1 AlphaScreen Binding Assay

| Example # | KRAS::SOS1 $IC_{50}$ A: ≤0.015 μM B: ≤0.15 μM C: ≤1 μM D: >1 μM | Example # | KRAS::SOS1 $IC_{50}$ A: ≤0.015 μM B: ≤0.15 μM C: ≤1 μM D: >1 μM |
|---|---|---|---|
| Example 25 | B | Example 64 | B |
| Example 26 | B | Example 65 | B |
| Example 27 | D | Example 66 | A |
| Example 28 | C | Example 67 | B |
| Example 29 | A | Example 68 | A |
| Example 30 | A | Example 69 | A |
| Example 31 | A | Example 70 | A |
| Example 32 | A | Example 71 | A |
| Example 33 | A | Example 72 | A |
| Example 34 | A | Example 73 | A |
| Example 35 | A | Example 74 | A |
| Example 36 | A | Example 75 | A |
| Example 37 | A | Example 76 | B |
| Example 38 | A | Example 77 | A |
| Example 39 | A | Example 78 | A |
| Example 79 | A | Example 80 | A |
| Example 81 | A | Example 82 | A |
| Example 83 | A | Example 84 | A |
| Example 85 | A | Example 86 | B |
| Example 87 | C | | |

b. Cell Proliferation Assay

The purpose of cell proliferation assay is to examine the potency with which compounds inhibit the SOS1-mediated proliferation of cancer cell lines in vitro in a defined cellular setting. Low $IC_{50}$ values are indicative of high potency of the compounds in this assay setting. It is observed that SOS1 inhibitor compounds demonstrate a potent inhibitory effect on the proliferation of KRAS mutant human cancer cell lines.

Cell proliferation assay is performed in three-dimensional (3D) ultra-low conditions with the human cell line NCI-H358, a human non-small cell lung cancer (NSCLC) cell line with a KRAS G12C mutation.

Materials Used:

96-well Clear Round Bottom Ultra-Low Attachment Microplate (Corning, Cat. 7007)

96-well Flat Clear Bottom White Polystyrene TC-treated Microplates (Corning, Cat. 3610)

RPMI-1640 Medium (Gibco, Cat. 22400105)

Fetal Bovine Serum (FBS) (Gibco, Cat. 10099141C)

0.25% Trypsin-EDTA (Gibco, Cat. 25200056)

Penicillin-Streptomycin (Gibco, Cat. 15140122)

CellTiter-Glo 3D Cell Viability Assay (Promega, Cat. G9683)

Assay Protocol:

NCI-H358 cells (ATCC, Cat. CRL-5807) are grown in cell culture flasks using RPMI medium supplemented with 10% FBS. Cells are incubated at 37° C. and 5% C02 in a humidified atmosphere, with sub-cultivation performed twice a week. Cells are trypsinized, counted and plated in 96-well ultra-low adhesion plates for 3D cell viability determination. The day after plating, serial dilutions of SOS1 inhibitor compounds are made using Tecan D300e Digital Dispenser to evaluate a concentration-dependent effect on cell viability. The concentration of the test compounds covers a range between 5 μM and 0.76 nM with serial 1:3 dilutions in 9 concentrations. 0.5 μL serial dilutions of the compounds are added in duplicates. 3 days later, the Cell-Titer-Glo 3D Cell Viability Assay is used to measure cell viability effects of SOS1 inhibitor compounds in 3D format.

Luminescent intensity is determined using Envision (PerkinElmer). Data is analyzed and $IC_{50}$ values are calculated using GraphPad Prism.

Compound $IC_{50}$ Values in H358 Cell Proliferation Assay

| Example # | anit-prolif. H358 $IC_{50}$ A: ≤0.1 μM B: ≤0.5 μM C: ≤1 μM D: >1 μM | Example # | anit-prolif. H358 $IC_{50}$ A: ≤0.1 μM B: ≤0.5 μM C: ≤1 μM D: >1 μM |
|---|---|---|---|
| Example 1 | A | Example 40 | A |
| Example 2 | A | Example 41 | B |
| Example 3 | B | Example 42 | B |
| Example 4 | B | Example 43 | A |
| Example 5 | B | Example 44 | A |
| Example 6 | A | Example 45 | A |
| Example 7 | B | Example 46 | A |
| Example 8 | B | Example 47 | B |
| Example 9 | B | Example 48 | B |
| Example 10 | D | Example 49 | C |
| Example 11 | C | Example 50 | B |
| Example 12 | B | Example 51 | D |
| Example 13 | C | Example 52 | A |
| Example 14 | C | Example 53 | A |
| Example 15 | A | Example 54 | B |
| Example 16 | B | Example 55 | B |
| Example 17 | A | Example 56 | B |
| Example 18 | C | Example 57 | A |
| Example 19 | B | Example 58 | A |
| Example 20 | A | Example 59 | A |
| Example 21 | A | Example 60 | A |
| Example 22 | D | Example 61 | A |
| Example 23 | — | Example 62 | B |
| Example 24 | B | Example 63 | C |
| Example 25 | B | Example 64 | C |
| Example 26 | — | Example 65 | B |
| Example 27 | — | Example 66 | A |
| Example 28 | — | Example 67 | A |
| Example 29 | A | Example 68 | B |

-continued

Compound $IC_{50}$ Values in H358 Cell Proliferation Assay

| Example # | anit-prolif. H358 $IC_{50}$ A: ≤0.1 μM B: ≤0.5 μM C: ≤1 μM D: >1 μM | Example # | anit-prolif. H358 $IC_{50}$ A: ≤0.1 μM B: ≤0.5 μM C: ≤1 μM D: >1 μM |
|---|---|---|---|
| Example 30 | A | Example 69 | A |
| Example 31 | A | Example 70 | B |
| Example 32 | A | Example 71 | B |
| Example 33 | B | Example 72 | B |
| Example 34 | B | Example 73 | A |
| Example 35 | B | Example 74 | B |
| Example 36 | B | Example 75 | A |
| Example 37 | B | Example 76 | B |
| Example 38 | C | Example 77 | B |
| Example 39 | B | Example 78 | |
| Example 79 | — | Example 80 | — |
| Example 81 | — | Example 82 | — |
| Example 83 | — | Example 84 | — |
| Example 85 | — | Example 86 | C |
| Example 87 | — | | |

Example 4. Biological Activity and Liver Microsomal Stability Comparison

Compound I-18 disclosed in WO2019/122129A1 was prepared. As shown in the table below, this compound has very poor stability in human liver microsomal assay and weaker activity in H358 cellular assay. Surprisingly, when the C—N bond between the tetrahydropyran ring and the bicyclic core in the compound I-18 was replaced with the N—N bond in the present compounds (compound 1-18 vs Examples 1, 17, 29, 30, 43, 53, and 61), the human liver microsomal stabilities of the present compounds were dramatically improved. Moreover, the present compounds' H358 cellular activities were significantly boosted as well.

| Example # | Human liver microsomal stability, $T_{1/2}$ (min)[a] | anit-prolif. H358 $IC_{50}$ (nM) |
|---|---|---|
| 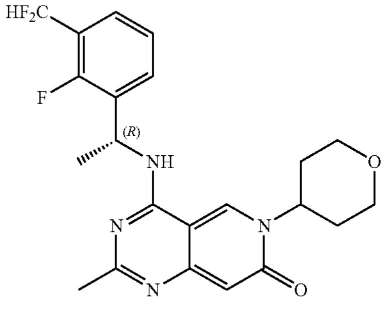 Comparative compound I-18 | 3 | 164 |

-continued
| Example # | Human liver microsomal stability, $T_{1/2}$ (min)[a] | anit-prolif. H358 $IC_{50}$ (nM) |
|---|---|---|
| 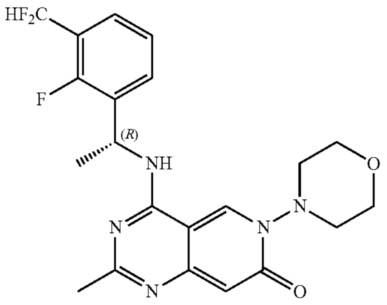 Example 1 | 84 | 40 |
| 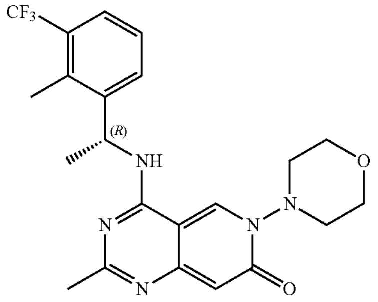 Example 17 | 110 | 23 |
| 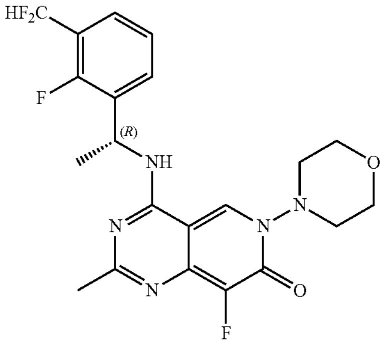 Example 29 | 140 | 49 |
| 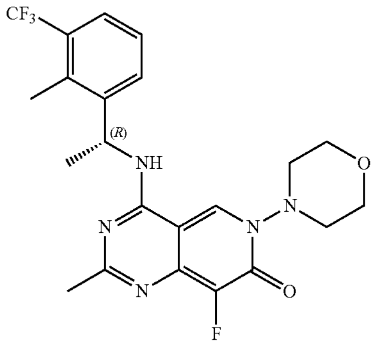 Example 30 | 190 | 28 |

-continued
| Example # | Human liver microsomal stability, $T_{1/2}$ (min)[a] | anit-prolif. H358 $IC_{50}$ (nM) |
| --- | --- | --- |
| 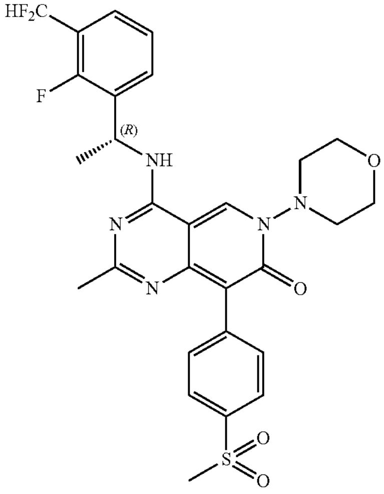 Example 43 | >1000 | 53 |
| 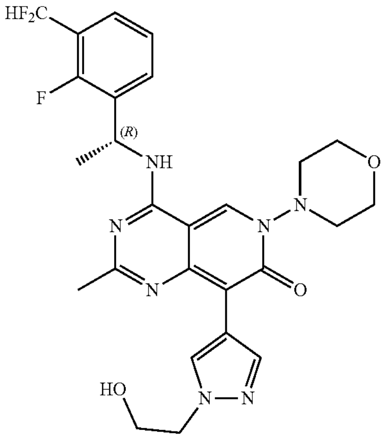 Example 53 | 44 | 60 |

-continued

| Example # | Human liver microsomal stability, $T_{1/2}$ (min)[a] | anit-prolif. H358 $IC_{50}$ (nM) |
|---|---|---|
| 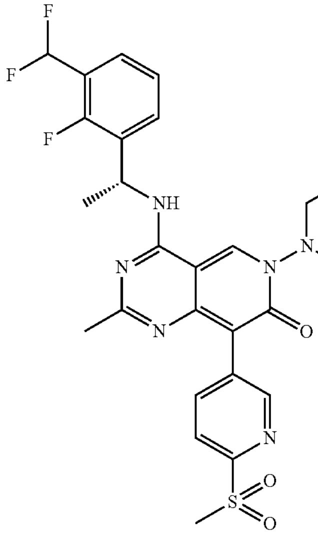 Example 61 | >1000 | 31 |

What is claimed is:

1. A compound of formula I:

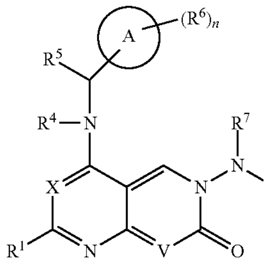

(I)

a pharmaceutically acceptable salt or a stereoisomer thereof, wherein:

ring A is 3-12 membered carbocyclyl, 3-12 membered heterocyclyl, 6-10 membered aryl, or 5-10 membered heteroaryl;

$R^1$ is hydrogen, halogen, $C_{1-6}$alkyl, or $C_{3-6}$cycloalkyl, wherein said $C_{1-6}$alkyl or $C_{3-6}$cycloalkyl represented by $R^1$ is optionally substituted by one to more groups selected from halogen and —OH;

V is N or $CR^2$; wherein $R^2$ is hydrogen, halogen, —CN, $C_{1-6}$alkyl, $C_{2-6}$alkenyl, $C_{2-6}$alkynyl, —$OR^{2a}$, —$NR^{2a}R^{2b}$, —$C(O)R^{2a}$, —$C(O)OR^{2a}$, —$C(O)NR^{2a}R^{2b}$, —$SO_2R^{2a}$, —$SO_2NR^{2a}R^{2b}$, —$P(O)R^{2a}R^{2b}$, —$NR^{2a}C(O)R^{2b}$, —$NR^{2a}C(O)OR^{2b}$, —$NR^{2a}SO_2R^{2b}$, —$NR^{2a}SO_2NR^{2b}R^{2c}$, 3-12 membered carbocyclyl, 3-12 membered heterocyclyl, 6-10 membered aryl, or 5-10 membered heteroaryl; wherein said $C_{1-6}$alkyl, $C_{2-6}$alkenyl, $C_{2-6}$alkynyl, 3-12 membered carbocyclyl, 3-12 membered heterocyclyl, 6-10 membered aryl, or 5-10 membered heteroaryl represented by $R^2$ is optionally substituted by one or more $R^{2d}$, wherein $R^{2a}$, $R^{2b}$, and $R^{2c}$ are independently selected from the group consisting of hydrogen, $C_{1-6}$alkyl, 3-12 membered carbocyclyl, 3-12 membered heterocyclyl, 6-10 membered aryl, and 5-10 membered heteroaryl; or $R^{2a}$ and $R^{2b}$ or $R^{2b}$ and $R^{2c}$ together with the N or P atom to which they are attached form 4-12 membered heterocyclyl or 5-10 membered heteroaryl; wherein said $C_{1-6}$alkyl, carbocyclyl, heterocyclyl, aryl, or heteroaryl represented by $R^{2a}$, $R^{2b}$, or $R^{2c}$ are optionally substituted with one or more $R^{2d}$; wherein $R^{2d}$, in each occurrence, is hydrogen, halogen, oxo, —CN, $C_{1-6}$alkyl, $C_{1-6}$haloalkyl, $C_{1-6}$hydroxyalkyl, —$OR^{2e}$, —$NR^{2e}R^{2f}$, —$C(O)R^{2e}$, —$C(O)OR^{2e}$, —$C(O)NR^{2e}R^{2f}$, —$SO_2R^{2e}$, —$SO_2NR^{2e}R^{2f}$, —$P(O)R^{2e}R^{2f}$, —$NR^{2e}C(O)R^{2f}$, —$NR^{2e}C(O)OR^{2f}$, —$NR^{2e}SO_2R^{2f}$, —$NR^{2e}SO_2NR^{2f}R^{2g}$, 3-12 membered carbocyclyl, 3-12 membered heterocyclyl, 6-10 membered aryl, or 5-10 membered heteroaryl;

$R^{2e}$, $R^{2f}$, and $R^{2g}$ are independently selected from the group consisting of hydrogen and $C_{1-6}$alkyl;

X is N or $CR^3$;

$R^3$ is hydrogen, halogen, or $C_{1-3}$alkyl;

$R^4$ is hydrogen or $C_{1-6}$alkyl;

$R^5$ is hydrogen, $C_{1-6}$alkyl, 3-6 membered monocyclic carbocyclyl, or 4-6 membered monocyclic heterocyclyl; wherein said $C_{1-6}$alkyl, 3-6 membered monocyclic carbocyclyl, or 4-6 membered monocyclic heterocyclyl represented by $R^5$ is optionally substituted with one or more groups selected from halogen and —OH;

$R^6$ is hydrogen, —OH, halogen, —CN, oxo, $C_{1-6}$alkyl, $C_{1-6}$alkoxy, —$SO_2R^{6a}$, —$SO_2NR^{6a}R^{6b}$, —$P(O)R^{6a}R^{6b}$, —$C(O)NR^{6a}R^{6b}$, —$NR^{6a}C(O)R^{6a}$, —$NR^{6a}C(O)NR^{6a}R^{6b}$, —$(CH_2)_sNR^{6a}R^{6b}$, —$O(CH_2)_tNR^{6a}R^{6b}$, 3-12 membered carbocyclyl, 3-12 membered heterocyclyl, 6-10 membered aryl, 5-10 membered heteroaryl; wherein said $C_{1-6}$alkyl, $C_{1-6}$alkoxy, 3-12 membered carbocyclyl, 3-12 membered heterocyclyl, 6-10 membered aryl, or 5-10 membered heteroaryl represented by $R^6$ is optionally substituted by one to more $R^{6c}$; wherein $R^{6a}$ and $R^{6b}$ are independently hydrogen or $C_{1-6}$alkyl, or $R^{6a}$ and $R^{6b}$ together with the N or P atom to which they are attached form 4-7 membered heterocyclyl;

s is an integral from 0 to 3;

t is an integral from 2 to 4;

$R^{6c}$, in each occurrence, is hydrogen, —OH, halogen, —CN, oxo, $C_{1-6}$alkyl, $C_{1-6}$alkoxy, $C_{3-6}$cycloalkyl, —$NR^{6a}R^{6b}$, —$SO_2R^{6a}$, —$SO_2NR^{6a}R^{6b}$, —C(O)$NR^{6a}R^{6b}$, —P(O)$R^{6a}R^{6b}$, —$NR^{6a}$C(O)$R^{6a}$, —$NR^{6a}$C(O)$NR^{6a}R^{6b}$, —$(CH_2)_sNR^{6a}R^{6b}$, or —$O(CH_2)_tNR^{6a}R^{6b}$; wherein said $C_{1-6}$alkyl or $C_{3-6}$cycloalkyl represented by $R^{6c}$ is optionally substituted with one to more groups selected from halogen, —OH and —$NR^{6a}R^{6b}$;

$R^7$ and $R^8$ are independently hydrogen, $C_{1-6}$alkyl, $C_{3-6}$alkenyl, $C_{3-6}$alkynyl, $C_{2-6}$alkoxy, 3-12 membered carbocyclyl, 3-12 membered heterocyclyl, 6-10 membered aryl, or 5-10 membered heteroaryl; wherein said $C_{1-6}$alkyl, $C_{3-6}$alkenyl, $C_{3-6}$alkynyl, $C_{2-6}$alkoxy, 3-12 membered carbocyclyl, 3-12 membered heterocyclyl, 6-10 membered aryl, or 5-10 membered heteroaryl represented by $R^7$ or $R^8$ is optionally substituted by one or more $R^{7a}$; or $R^7$ and $R^8$ together with the N atom to which they are attached form 4-12 membered heterocyclyl or 5-10 membered heteroaryl; wherein said 4-12 membered heterocyclyl or 5-10 membered heteroaryl is optionally substituted with one or more R *7b;*

$R^{7a}$ is hydrogen, halogen, —CN, $C_{1-6}$alkyl, —$OR^{7c}$, —$NR^{7c}R^{7d}$, —C(O)$R^{7c}$, —C(O)$OR^{7c}$, —C(O)$NR^{7c}R^{7d}$, —$SO_2R^{7c}$, —P(O)$R^{7c}R^{7d}$, —$SO_2NR^{7c}R^{7d}$, —$NR^{7c}$C(O)$R^{7d}$, —$NR^{7c}$C(O)$OR^{7d}$, —$NR^{7c}SO_2R^{7d}$, —$NR^{7c}SO_2NR^{7d}R^{7e}$, 3-12 membered carbocyclyl, 3-12 membered heterocyclyl, 6-10 membered aryl, or 5-10 membered heteroaryl, wherein said $C_{1-6}$alkyl, 3-12 membered carbocyclyl, 3-12 membered heterocyclyl, 6-10 membered aryl, or 5-10 membered heteroaryl represented by $R^{7a}$ is optionally substituted by one or more $R^{7f}$;

$R^{7b}$ is hydrogen, halogen, —CN, oxo, $C_{1-6}$alkyl, $C_{2-6}$alkenyl, $C_{2-6}$alkynyl, $C_{1-6}$alkoxy, —$OR^{7c}$, —$NR^{7c}R^{7d}$, —C(O)$R^{7c}$, —C(O)$OR^{7c}$, —C(O)$NR^{7c}R^{7d}$, —$SO_2R^{7c}$, —P(O)$R^{7c}R^{7d}$, —$SO_2NR^{7c}R^{7d}$, —$NR^{7c}$C(O)$R^{7d}$, —$NR^{7c}$C(O)$OR^{7d}$, —$NR^{7c}SO_2R^{7d}$, —$NR^{7c}SO_2NR^{7d}R^{7e}$, 3-12 membered carbocyclyl, 3-12 membered heterocyclyl, 6-10 membered aryl, or 5-10 membered heteroaryl, wherein $C_{1-6}$alkyl, $C_{2-6}$alkenyl, $C_{2-6}$alkynyl, $C_{1-6}$alkoxy, 3-12 membered carbocyclyl, 3-12 membered heterocyclyl, or 5-10 membered heteroaryl represented by $R^{7b}$ is optionally substituted by one or more $R^{7f}$;

$R^{7c}$, $R^{7d}$, and $R^{7e}$ are independently selected from the group consisting of hydrogen, $C_{1-6}$alkyl, 3-12 membered carbocyclyl, 4-12 membered heterocyclyl, 6-10 membered aryl, and 5-10 membered heteroaryl; or $R^{7c}$ and $R^{7d}$ together with the N or P atom to which they are attached form 4-12 membered heterocyclyl or 5-10 membered heteroaryl; wherein said $C_{1-6}$alkyl, carbocyclyl, heterocyclyl, aryl, or heteroaryl represented by $R^{7c}$, $R^{7d}$, or $R^{7e}$ is optionally substituted with one or more $R^{7f}$;

$R^{7f}$, in each occurrence, is hydrogen, halogen, —CN, or —OH; and n is 0, 1, 2, or 3;

wherein said heterocyclyl comprises 1-4 heteroatoms selected from O, N, and S; and said heteroaryl comprises 1-4 heteroatoms selected from O, N, and S.

2. The compound of claim 1 or a pharmaceutically acceptable salt or a stereoisomer thereof, wherein the compound is represented by Formula II:

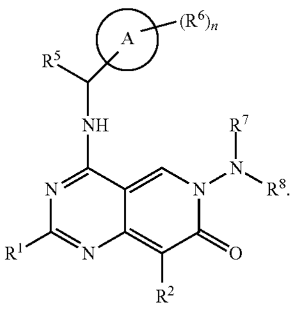

(II)

3. The compound of claim 2, or a pharmaceutically acceptable salt or a stereoisomer thereof, wherein ring A is 3-10 membered carbocyclyl, 4-10 membered heterocyclyl, 6-10 membered aryl, or 5-10 membered heteroaryl;

$R^1$ is hydrogen, $C_{1-4}$alkyl, or $C_{3-6}$cycloalkyl;

$R^2$ is hydrogen, halogen, —CN, $C_{1-4}$alkyl, $C_{2-4}$alkenyl, $C_{2-4}$alkynyl, —$OR^{2a}$, —$NR^{2a}R^{2b}$, —C(O)$R^{2a}$, —C(O)$OR^{2a}$, —C(O)$NR^{2a}R^{2b}$, —$NR^{2a}$C(O)$R^{2b}$, —$NR^{2a}$C(O)$OR^{2b}$, 3-6 membered monocyclic carbocyclyl, 3-6 membered monocyclic heterocyclyl, 6-10 membered aryl, or 5-10 membered heteroaryl; wherein said $C_{1-4}$alkyl, $C_{2-4}$alkenyl, $C_{2-4}$alkynyl, 3-6 membered monocyclic carbocyclyl, 3-6 membered monocyclic heterocyclyl, 6-10 membered aryl, or 5-10 membered heteroaryl represented by $R^2$ is optionally substituted by one to three $R^{2d}$; wherein $R^{2a}$ and $R^{2b}$ are independently selected from the group consisting of hydrogen, $C_{1-6}$alkyl, $C_{1-6}$haloalkyl, or $C_{1-6}$hydroxyalkyl; or $R^{2a}$ and $R^{2b}$ together with the N atom to which they are attached form 4-12 membered heterocyclyl or 5-10 membered heteroaryl;

$R^{2d}$, in each occurrence, is hydrogen, halogen, oxo, —CN, $C_{1-6}$alkyl, $C_{1-6}$haloalkyl, $C_{1-6}$hydroxyalkyl, —$OR^{2e}$, —$NR^{2e}R^{2f}$, —$SO_2R^{2e}$, —P(O)$R^{2e}R^{2f}$, $COOR^{2e}$, $CONR^{2e}R^{2f}$, 3-6 membered monocyclic carbocyclyl, 3-6 membered monocyclic heterocyclyl, 6-10 membered aryl, or 5-10 membered heteroaryl;

$R^{2e}$ and $R^{2f}$ are independently selected from the group consisting of hydrogen and $C_{1-6}$alkyl;

$R^5$ is hydrogen, $C_{1-4}$alkyl, 3-5 membered monocyclic carbocyclyl, or 4-5 membered monocyclic heterocyclyl;

$R^6$ is hydrogen, —OH, halogen, —CN, oxo, $C_{1-6}$alkyl, —$(CH_2)_sNR^{6a}R^{6b}$, 3-6 membered monocyclic carbocyclyl, 3-6 membered monocyclic heterocyclyl, 6-10 membered aryl, 5-10 membered heteroaryl; wherein said $C_{1-6}$alkyl, 3-6 membered monocyclic carbocyclyl, 3-6 membered monocyclic heterocyclyl, 6-10 membered aryl, or 5-10 membered heteroaryl represented by $R^6$ is optionally substituted by one to more $R^{6c}$; wherein $R^{6a}$ and $R^{6b}$ are independently hydrogen or $C_{1-4}$alkyl;

s is an integral from 0 to 2;

$R^{6c}$, in each occurrence, is hydrogen, —OH, halogen, —CN, oxo, $C_{1-6}$alkyl, —$NR^{6a}R^{6b}$, or —$(CH_2)NR^{6a}R^{6b}$; wherein said $C_{1-6}$alkyl represented by $R^{6c}$ is optionally substituted with one to more groups selected from halogen and —OH;

$R^7$ and $R^8$ are independently hydrogen, $C_{1-4}$alkyl, $C_{3-4}$alkenyl, $C_{3-4}$alkynyl, $C_{2-4}$alkoxy, 3-6 membered monocyclic carbocyclyl, 3-6 membered monocyclic heterocyclyl, 6-10 membered aryl, or 5-10 membered heteroaryl; wherein said $C_{1-4}$alkyl, $C_{3-4}$alkenyl, $C_{3-4}$alkynyl, $C_{2-4}$alkoxy, 3-6 membered monocyclic carbocyclyl, 3-6 membered monocyclic heterocyclyl, 6-10 membered aryl, or 5-10 membered heteroaryl represented by $R^7$ or $R^8$ is optionally substituted by one or more $R^{7a}$; or $R^7$ and $R^8$ together with the N atom to which they are attached form 4-12 membered heterocyclyl or 5-10 membered heteroaryl; wherein said 4-12 membered heterocyclyl or 5-10 membered heteroaryl is optionally substituted with one to three $R^{7b}$;

$R^{7a}$ is hydrogen, halogen, —CN, $C_{1-6}$alkyl, —$OR^{7c}$, or —$NR^{7c}R^{7d}$, $R^{7b}$ is hydrogen, halogen, —CN, oxo, $C_{1-6}$alkyl, $C_{1-6}$alkoxy, —$OR^{7c}$, —$NR^{7c}R^{7d}$, —$C(O)R^{7c}$, —$C(O)OR^{7c}$, —$SO_2R^{7c}$, or 5-10 membered heteroaryl, wherein $C_{1-6}$alkyl, $C_{1-6}$alkoxy, or 5-10 membered heteroaryl represented by $R^{7b}$ is optionally substituted by one or more $R^{7f}$;

$R^{7c}$ and $R^{7d}$ are independently selected from the group consisting of hydrogen, $C_{1-4}$alkyl, 3-6 membered monocyclic carbocyclyl, 4-8 membered heterocyclyl, 6-10 membered aryl, and 5-10 membered heteroaryl; or $R^{7c}$ and $R^{7d}$ together with the N atom to which they are attached form 4-8 membered heterocyclyl or 5-10 membered heteroaryl; wherein said $C_{1-4}$alkyl, 3-6 membered monocyclic carbocyclyl, 4-8 membered heterocyclyl, 6-10 membered aryl, or 5-10 membered heteroaryl represented by $R^{7c}$ or $R^{7d}$ is optionally substituted with one to three $R^{7f}$; and $R^{7f}$, in each occurrence, is hydrogen, halogen, —CN, or —OH.

4. The compound of claim 3 or a pharmaceutically acceptable salt or a stereoisomer thereof, wherein $R^2$ is hydrogen, halogen, —CN, $C_{1-4}$alkyl, $C_{2-4}$alkenyl, $C_{2-4}$alkynyl, 3-6 membered monocyclic carbocyclyl, 3-6 membered monocyclic heterocyclyl, 6-10 membered aryl, or 5-10 membered heteroaryl; wherein said $C_{1-4}$alkyl, $C_{2-4}$alkenyl, $C_{2-4}$alkynyl, 3-6 membered monocyclic carbocyclyl, 3-6 membered monocyclic heterocyclyl, 6-10 membered aryl, or 5-10 membered heteroaryl represented by $R^2$ is optionally substituted by one to three $R^{2d}$; wherein $R^{2d}$, in each occurrence, is hydrogen, halogen, oxo, —CN, $C_{1-6}$alkyl, $C_{1-6}$haloalkyl, $C_{1-6}$hydroxyalkyl, —$OR^{2e}$, —$NR^{2e}R^{2f}$, —$SO_2R^{2e}$, —$P(O)R^{2e}R^{2f}$, $COOR^{2e}$, $CONR^{2e}R^{2f}$, 3-6 membered monocyclic carbocyclyl, 3-6 membered monocyclic heterocyclyl, 6-10 membered aryl, or 5-10 membered heteroaryl; and $R^{2e}$ and $R^{2f}$ are independently selected from the group consisting of hydrogen and $C_{1-6}$alkyl.

5. The compound of claim 4 or a pharmaceutically acceptable salt or a stereoisomer thereof, wherein $R^7$ and $R^8$ are independently hydrogen, $C_{1-4}$alkyl, $C_{3-4}$alkenyl, $C_{3-4}$alkynyl; wherein said $C_{1-4}$alkyl, $C_{3-4}$alkenyl, $C_{3-4}$alkynyl represented by $R^7$ or $R^8$ is optionally substituted by one or more $R^{7a}$; or $R^7$ and $R^8$ together with the N atom to which they are attached form 4-12 membered heterocyclyl or 5 membered heteroaryl, each of which is optionally substituted with one to three $R^{7b}$;

$R^{7a}$ is hydrogen, halogen, —CN, $C_{1-6}$alkyl, —$OR^{7c}$, or —$NR^{7c}R^{7d}$;

$R^{7b}$ is hydrogen, halogen, —CN, oxo, —OH, $C_{1-6}$alkyl, $C_{1-6}$alkoxy, —$NR^{7c}R^{7d}$, —$C(O)R^{7c}$, —$C(O)OR^{7c}$, —$SO_2R^{7c}$, or 5-10 membered heteroaryl, wherein $C_{1-6}$alkyl, $C_{1-6}$alkoxy, or 5-10 membered heteroaryl represented by $R^{7b}$ is optionally substituted by one or more $R^{7f}$;

$R^{7c}$ and $R^{7d}$ are independently selected from the group consisting of hydrogen, $C_{1-4}$alkyl, 3-6 membered monocyclic carbocyclyl, 4-8 membered heterocyclyl, 6-10 membered aryl, and 5-10 membered heteroaryl; or $R^{7c}$ and $R^{7d}$ together with the N atom to which they are attached form 4-8 membered heterocyclyl or 5-10 membered heteroaryl; wherein said $C_{1-4}$alkyl, 3-6 membered monocyclic carbocyclyl, 4-8 membered heterocyclyl, 6-10 membered aryl, or 5-10 membered heteroaryl represented by $R^{7c}$ or $R^{7d}$ is optionally substituted with one to three $R^{7f}$; and $R^{7f}$, in each occurrence, is hydrogen, halogen, —CN, or -OH.

6. The compound of claim 5 or a pharmaceutically acceptable salt or a stereoisomer thereof, wherein i) ring A is 3-6 membered monocyclic cycloalkyl, 4-6 membered monocyclic heterocyclyl, phenyl, or 5-10 membered heteroaryl;

$R^6$ is hydrogen, —OH, halogen, —CN, $C_{1-6}$alkyl, or —$(CH_2)_sNR^{6a}R^{6b}$; wherein said $C_{1-6}$alkyl represented by $R^6$ is optionally substituted with one to more groups selected from halogen and —OH;

$R^{6a}$ and $R^{6b}$ are independently hydrogen or $C_{1-4}$alkyl; and s is 0, or 1; or ii) ring A is cyclopropyl, phenyl, thiophene, or indole.

7. The compound of claim 1 or a pharmaceutically acceptable salt or stereoisomer thereof, wherein the compound is represented by Formula (III-A) or (III-B):

(III-A)

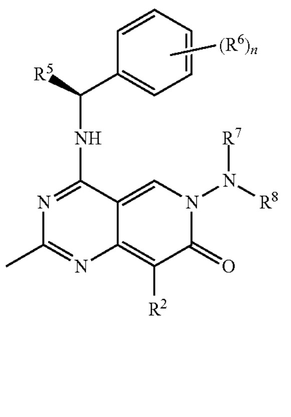

or

-continued (III-B)

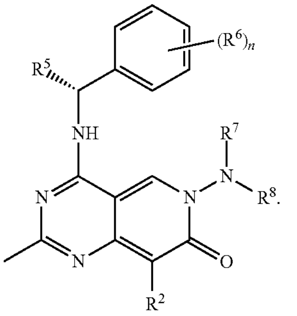

8. The compound of claim 7 or a pharmaceutically acceptable salt or a stereoisomer thereof, wherein $R^6$ is hydrogen, halogen, $C_{1-4}$alkyl, or —$(CH_2)NR^{6a}R^{6b}$; wherein said $C_{1-4}$alkyl represented by $R^6$ is optionally substituted with one to more groups selected from halogen and —OH; and $R^{6a}$ and $R^{6b}$ are independently hydrogen or $C_{1-4}$alkyl.

9. The compound of claim 8 or a pharmaceutically acceptable salt or a stereoisomer thereof, wherein $R^5$ is hydrogen, methyl, or ethyl.

10. The compound of claim 9 or a pharmaceutically acceptable salt or a stereoisomer thereof, wherein i) $R^2$ is hydrogen, halogen, —CN, $C_{1-4}$alkyl, $C_{2-4}$alkenyl, 3-6 membered monocyclic cycloalkyl, 5-6 membered monocyclic heterocyclyl, phenyl, or 5-10 membered heteroaryl; wherein said $C_{1-4}$alkyl, 3-6 membered monocyclic cycloalkyl, 5-6 membered monocyclic heterocyclyl, phenyl, or 5-10 membered heteroaryl represented by $R^2$ is optionally substituted by one to three $R^{2d}$;

$R^{2d}$, in each occurrence, is hydrogen, halogen, oxo, —CN, $C_{1-6}$alkyl, $C_{1-6}$haloalkyl, $C_{1-6}$hydroxyalkyl, —$OR^{2e}$, —$NR^{2e}R^{2f}$, —$SO_2R^{2e}$, —$P(O)R^{2e}R^{2f}$, $COOR^{2e}$, $CONR^{2e}R^{2f}$, 3-6 membered monocyclic carbocyclyl, 3-6 membered monocyclic heterocyclyl, phenyl, or 5-10 membered heteroaryl; and $R^{2e}$ and $R^{2f}$ are independently selected from the group consisting of hydrogen and $C_{1-6}$alkyl;

ii) $R^2$ is phenyl or 5-10 membered heteroaryl; wherein said phenyl or 5-10 membered heteroaryl is optionally substituted by one to three $R^{2d}$;

$R^{2d}$, in each occurrence, is hydrogen, halogen, —CN, $C_{1-6}$alkyl, $C_{1-6}$haloalkyl, $C_{1-6}$hydroxyalkyl, —$OR^{2e}$, —$NR^{2e}R^{2f}$, —$SO_2R^{2e}$, —$P(O)R^{2e}R^{2f}$, $COOR^{2e}$, $CONR^{2e}R^{2f}$, 3-6 membered monocyclic carbocyclyl, 3-6 membered monocyclic heterocyclyl, phenyl, or 5-10 membered heteroaryl; and $R^{2e}$ and $R^{2f}$ are independently selected from the group consisting of hydrogen and $C_{1-6}$alkyl;

iii) $R^2$ is phenyl, pyridyl, pyrimidyl, imidazolyl, pyrazolyl, imidazo[1,2-a]pyrimidine, imidazo[1,2-a]pyridine, or triazolo[4,3-a]pyridine, each of which is optionally substituted by one to three $R^{2d}$; wherein $R^{2d}$ is selected from the group consisting of hydrogen, halogen, —CN, —$CH_3$, —$CF_3$, —$NH_2$, —$S(O)_2Me$, —$OCH_3$, COOH, $CONH_2$, COOMe, —$P(O)(CH_3)_2$, —$CH_2CH_2OH$, and —$CH_2CHF_2$; or iv) $R^2$ is phenyl or pyridyl, each of which is optionally substituted by one to three $R^{2d}$; wherein $R^{2d}$ is selected from the group consisting of hydrogen, halogen, —CN, —$CH_3$, —$CF_3$, —$NH_2$, —$S(O)_2Me$, —$OCH_3$, COOH, $CONH_2$, COOMe, —$P(O)(CH_3)_2$, —$CH_2CH_2OH$, and —$CH_2CHF_2$.

11. The compound of claim 10 or a pharmaceutically acceptable salt or a stereoisomer thereof, wherein i) $R^7$ and $R^8$ together with the N atom to which they are attached form 5-10 membered heterocyclyl or 5 membered heteroaryl, each of which is optionally substituted with one to three groups selected from halogen, —CN, oxo, —OH, $C_{1-6}$alkyl, $C_{1-6}$alkoxy, —$C(O)R^{7c}$, —$C(O)OR^{7c}$, and pyridinyl optionally substituted with CN;

$R^{7c}$ is independently selected from the group consisting of hydrogen, $C_{1-4}$alkyl optionally substituted with —CN or —OH; or ii) $R^7$ and $R^8$ are independently hydrogen or $C_{1-4}$alkyl.

12. The compound of claim 11, or a pharmaceutically acceptable salt or a stereoisomer thereof, wherein $R^2$ is selected from the group consisting of H, F, Br, $CH_3$, -CN, 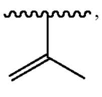 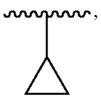

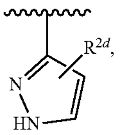 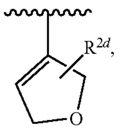 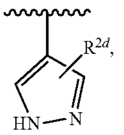 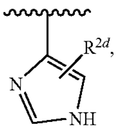

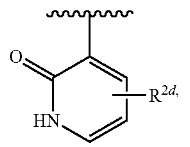 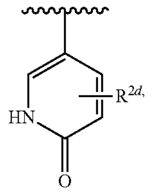 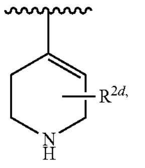

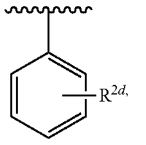 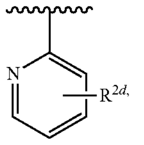 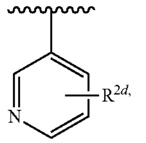

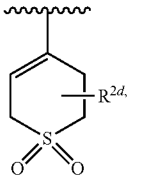 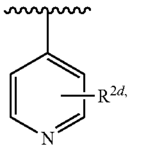 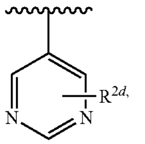

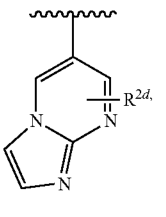 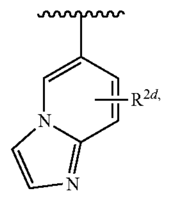 and 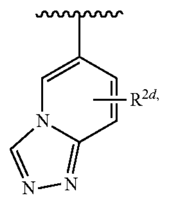

wherein $R^{2d}$ is selected from the group consisting of hydrogen, halogen, —CN, —$CH_3$, —$CF_3$, —$NH_2$, —$S(O)_2Me$, —$OCH_3$, COOH, $CONH_2$, COOMe, —$P(O)(CH_3)_2$, —$CH_2CH_2OH$, and —$CH_2CHF_2$.

13. The compound of claim 12 or a pharmaceutically acceptable salt or a stereoisomer thereof, wherein $R^7$ and $R^8$ together with the atom to which they are attached form a heterocyclyl selected from the group consisting of

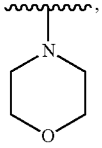, 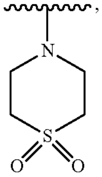, 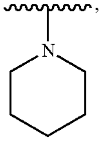, 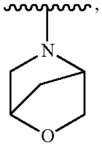,
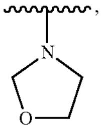, 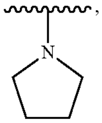, 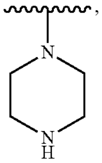, 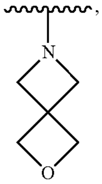,
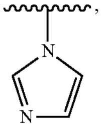, 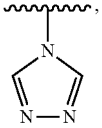, and 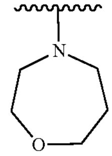,
each of which is optionally substituted with one to three groups selected from —F, —CN, oxo, —OH, methyl, isopropyl, methoxy, —C(O)$R^{7c}$, —C(O)O$R^{7c}$, and pyridinyl optionally substituted with CN.
14. A compound selected from the group consisting of
| ID | Structure |
|---|---|
| Example 1 | 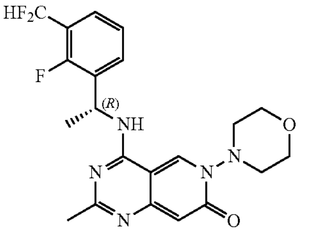 |
| Example 2 | 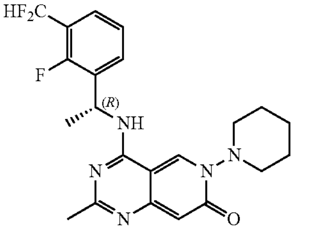 |
| Example 3 | 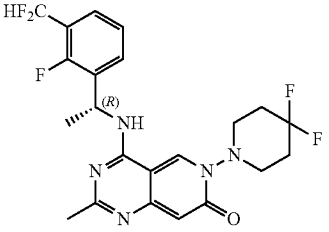 |
-continued
| ID | Structure |
|---|---|
| Example 4 | 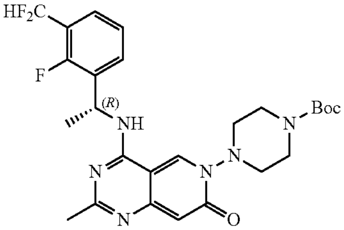 |
| Example 5 | 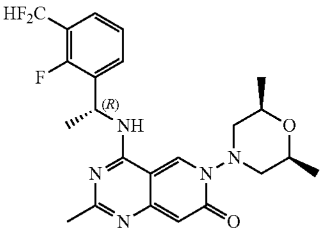 |
| Example 6 | 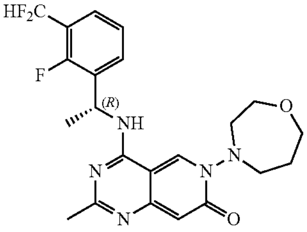 |
| Example 7 | 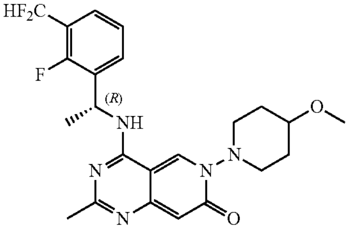 |
| Example 8 | 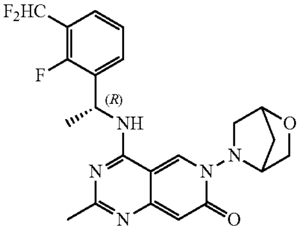 |
| Example 9 | 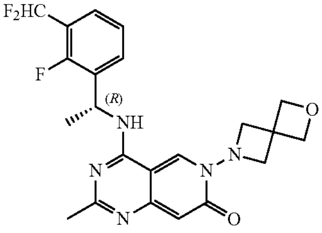 |

-continued
| ID | Structure |
| --- | --- |
| Example 10 | 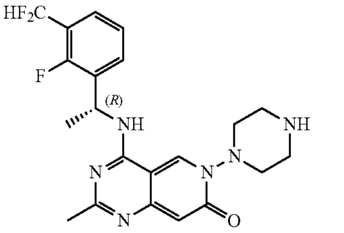 |
| Example 11 | 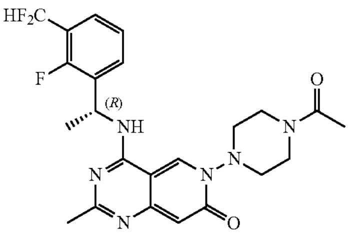 |
| Example 12 | 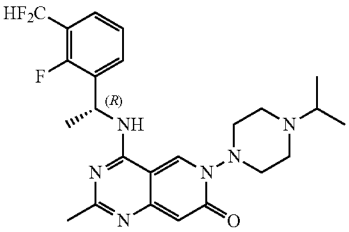 |
| Example 13 | 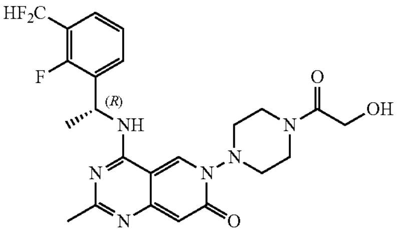 |
| Example 14 | 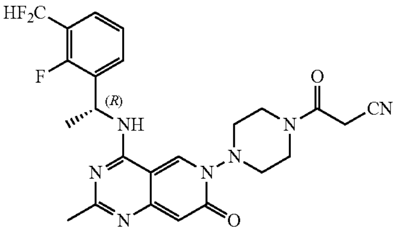 |
| Example 15 | 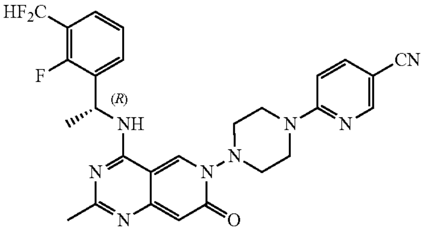 |
-continued
| ID | Structure |
| --- | --- |
| Example 16 | 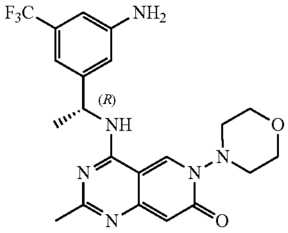 |
| Example 17 | 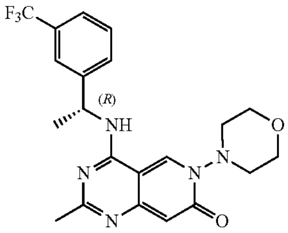 |
| Example 18 | 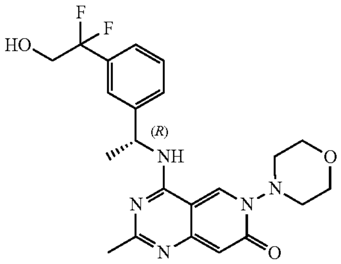 |
| Example 19 | 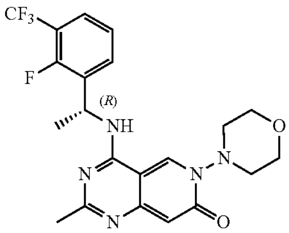 |
| Example 20 | 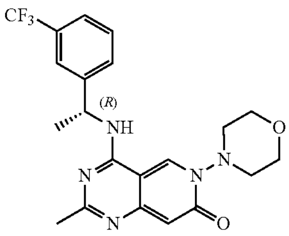 |
| Example 21 | 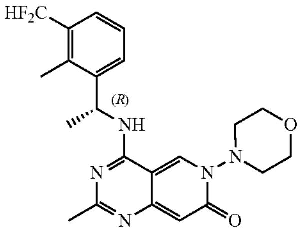 |

-continued
| ID | Structure |
|---|---|
| Example 22 | 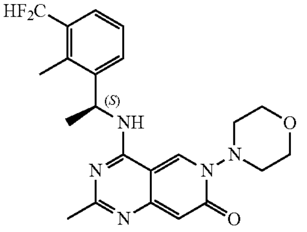 |
| Example 23 | 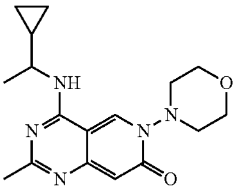 [SMILES: Cc1nc(NC(C)C2CC2)c2cn(N3CCOCC3)c(=O)cc2n1] |
| Example 24 | 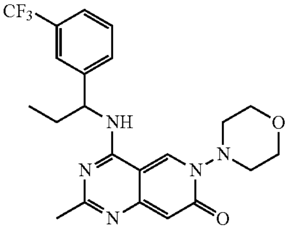 [SMILES: CCC(Nc1nc(C)nc2cc(=O)n(N3CCOCC3)cc12)c1cccc(C(F)(F)F)c1] |
| Example 25 | 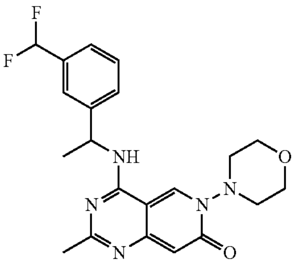 [SMILES: Cc1nc(NC(C)c2cccc(C(F)F)c2)c2cn(N3CCOCC3)c(=O)cc2n1] |
| Example 26 | 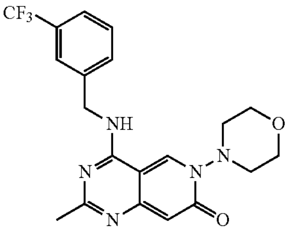 [SMILES: Cc1nc(NCc2cccc(C(F)(F)F)c2)c2cn(N3CCOCC3)c(=O)cc2n1] |
| Example 27 | 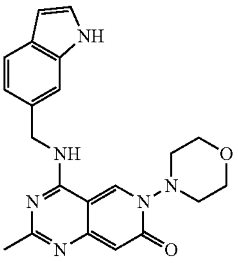 [SMILES: Cc1nc(NCc2ccc3cc[nH]c3c2)c2cn(N3CCOCC3)c(=O)cc2n1] |
-continued
| ID | Structure |
|---|---|
| Example 28 | 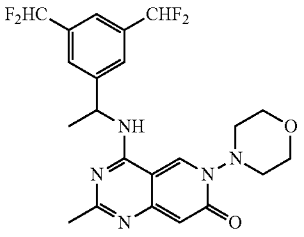 [SMILES: Cc1nc(NC(C)c2cc(C(F)F)cc(C(F)F)c2)c2cn(N3CCOCC3)c(=O)cc2n1] |
| Example 29 | 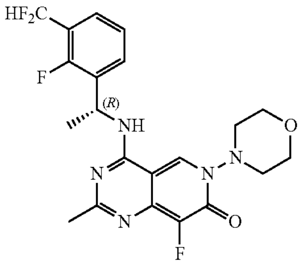 |
| Example 30 | 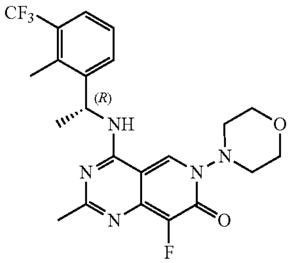 |
| Example 31 | 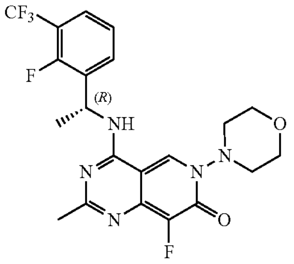 |
| Example 32 | 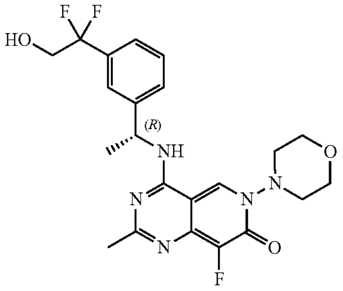 |
| Example 33 | 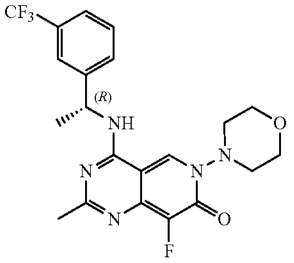 |

-continued
| ID | Structure |
|---|---|
| Example 34 | 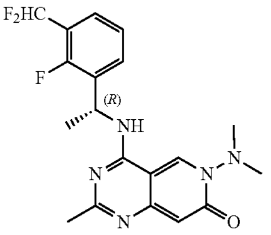 |
| Example 35 | 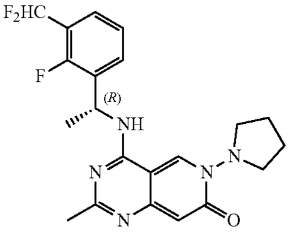 |
| Example 36 | 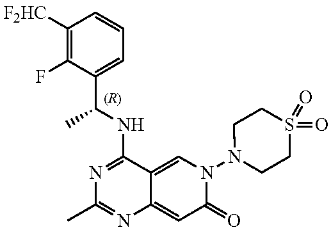 |
| Example 37 | 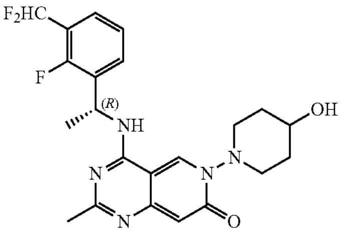 |
| Example 38 | 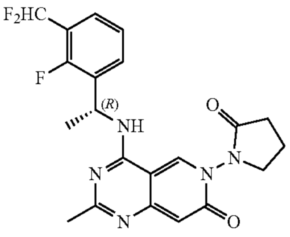 |
| Example 39 | 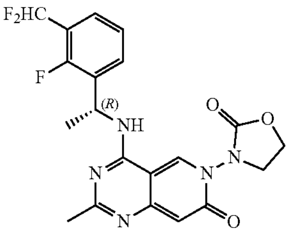 |
-continued
| ID | Structure |
|---|---|
| Example 40 | 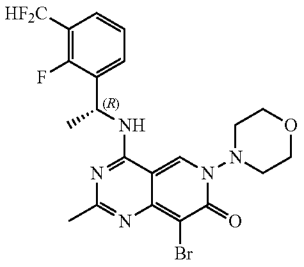 |
| Example 41 | 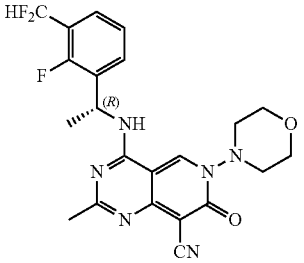 |
| Example 42 | 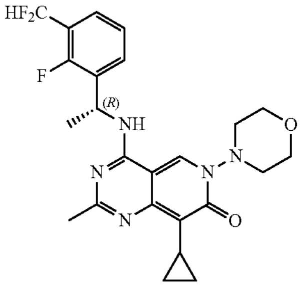 |
| Example 43 | 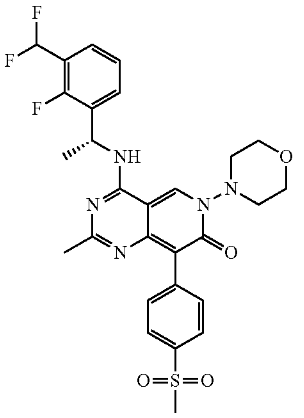 |
| Example 44 | 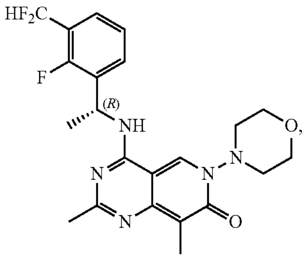 |

-continued
| ID | Structure |
| --- | --- |
| Example 45 | 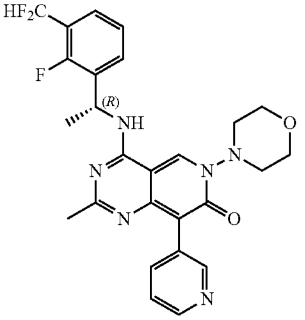 |
| Example 46 | 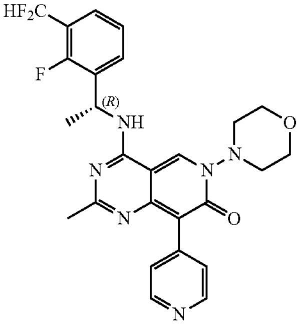 |
| Example 47 | 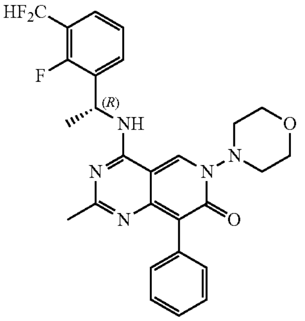 |
| Example 48 | 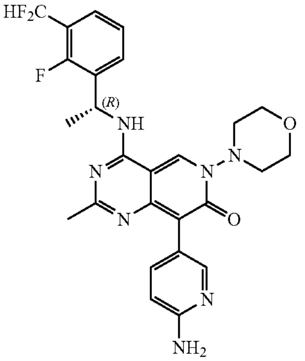 |
| Example 49 | 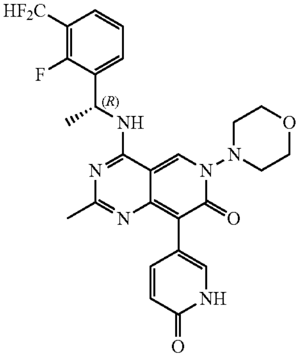 |
| Example 50 | 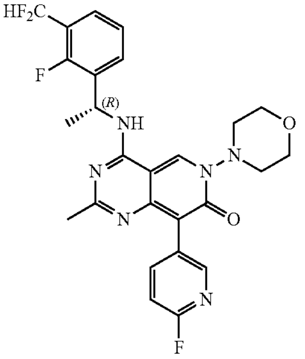 |
| Example 51 | 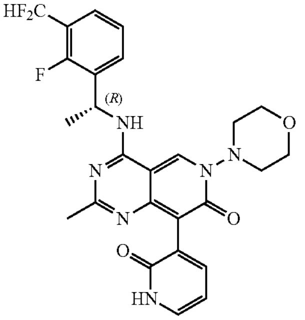 |
| Example 52 | 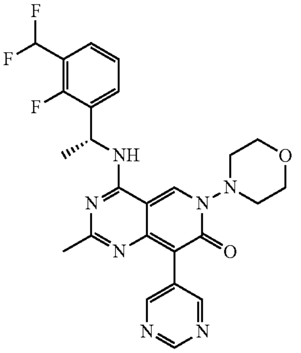 [SMILES: Cc1nc(N[C@H](C)c2cccc(C(F)F)c2F)c2cn(N3CCOCC3)c(=O)c(-c3cncnc3)c2n1] |

-continued
| ID | Structure |
|---|---|
| Example 53 | 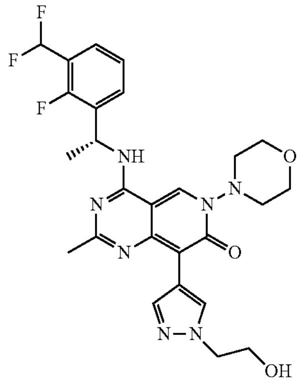 [SMILES: Cc1nc(N[C@H](C)c2cccc(C(F)F)c2F)c2cn(N3CCOCC3)c(=O)c(-c3cnn(CCO)c3)c2n1] |
| Example 54 | 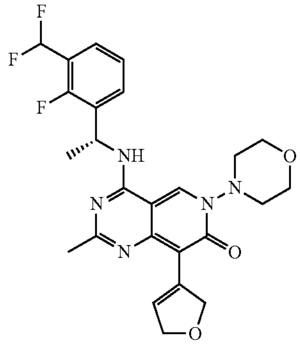 [SMILES: Cc1nc(N[C@H](C)c2cccc(C(F)F)c2F)c2cn(N3CCOCC3)c(=O)c(C3=CCOC3)c2n1] |
| Example 55 | 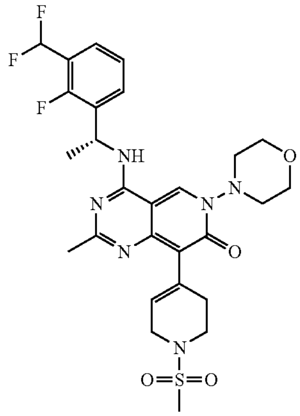 [SMILES: Cc1nc(N[C@H](C)c2cccc(C(F)F)c2F)c2cn(N3CCOCC3)c(=O)c(C3=CCN(S(C)(=O)=O)CC3)c2n1] |
| Example 56 | 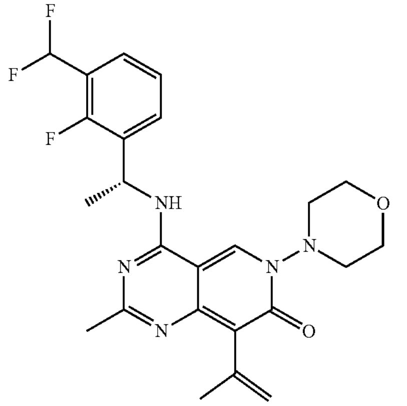 [SMILES: C=C(C)c1c(=O)n(N2CCOCC2)cc2c(N[C@H](C)c3cccc(C(F)F)c3F)nc(C)nc12] |
-continued
| ID | Structure |
|---|---|
| Example 57 | 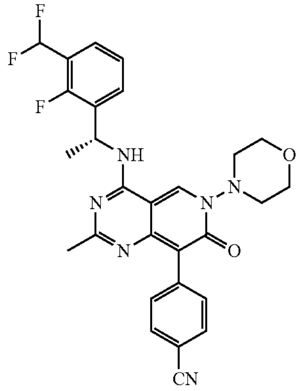 |
| Example 58 | 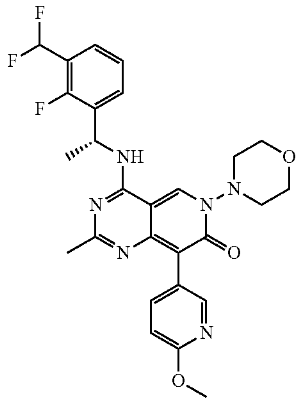 [SMILES: COc1ccc(-c2c(=O)n(N3CCOCC3)cc3c(N[C@H](C)c4cccc(C(F)F)c4F)nc(C)nc23)cn1] |
| Example 59 | 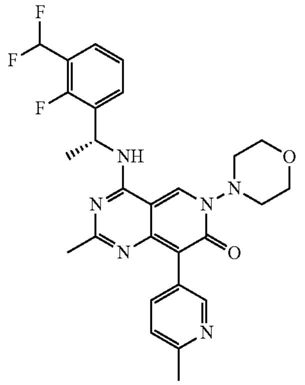 [SMILES: Cc1ccc(-c2c(=O)n(N3CCOCC3)cc3c(N[C@H](C)c4cccc(C(F)F)c4F)nc(C)nc23)cn1] |
| Example 60 | 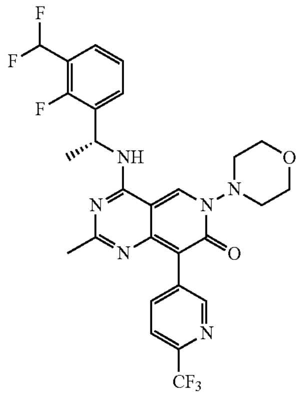 [SMILES: Cc1nc(N[C@H](C)c2cccc(C(F)F)c2F)c2cn(N3CCOCC3)c(=O)c(-c3ccc(C(F)(F)F)nc3)c2n1] |

-continued
| ID | Structure |
| --- | --- |
| Example 61 | 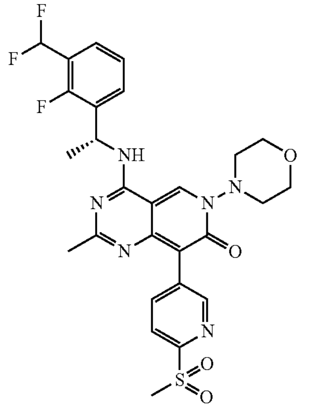 [SMILES: Cc1nc(N[C@H](C)c2cccc(C(F)F)c2F)c2cn(N3CCOCC3)c(=O)c(-c3ccc(S(C)(=O)=O)nc3)c2n1] |
| Example 62 | 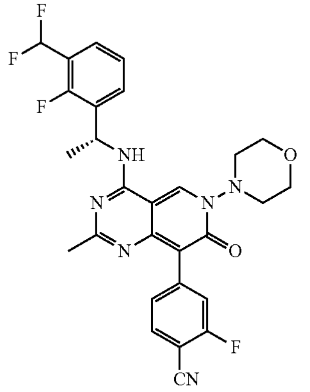 [SMILES: Cc1nc(N[C@H](C)c2cccc(C(F)F)c2F)c2cn(N3CCOCC3)c(=O)c(-c3ccc(C#N)c(F)c3)c2n1] |
| Example 63 | 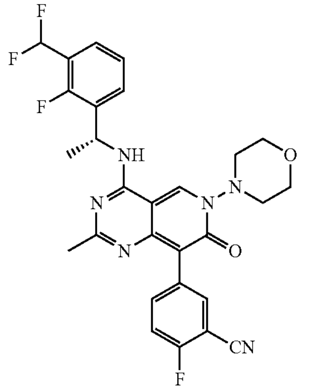 [SMILES: Cc1nc(N[C@H](C)c2cccc(C(F)F)c2F)c2cn(N3CCOCC3)c(=O)c(-c3ccc(F)c(C#N)c3)c2n1] |
| Example 64 | 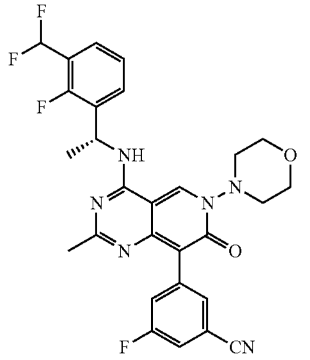 [SMILES: Cc1nc(N[C@H](C)c2cccc(C(F)F)c2F)c2cn(N3CCOCC3)c(=O)c(-c3cc(F)cc(C#N)c3)c2n1] |
-continued
| ID | Structure |
| --- | --- |
| Example 65 | 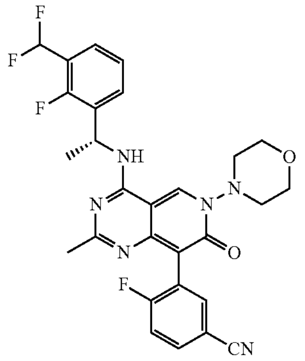 [SMILES: Cc1nc(N[C@H](C)c2cccc(C(F)F)c2F)c2cn(N3CCOCC3)c(=O)c(-c3cc(C#N)ccc3F)c2n1] |
| Example 66 | 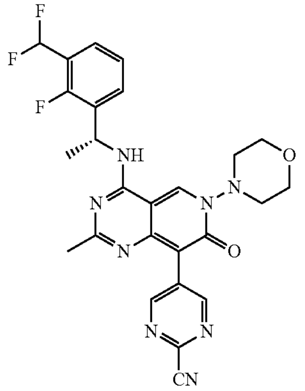 [SMILES: Cc1nc(N[C@H](C)c2cccc(C(F)F)c2F)c2cn(N3CCOCC3)c(=O)c(-c3cnc(C#N)nc3)c2n1] |
| Example 67 | 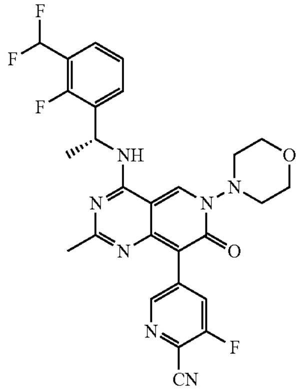 [SMILES: Cc1nc(N[C@H](C)c2cccc(C(F)F)c2F)c2cn(N3CCOCC3)c(=O)c(-c3cnc(C#N)c(F)c3)c2n1] |
| Example 68 | 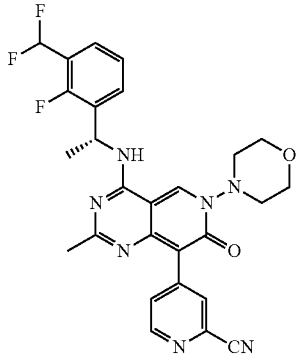 [SMILES: Cc1nc(N[C@H](C)c2cccc(C(F)F)c2F)c2cn(N3CCOCC3)c(=O)c(-c3ccnc(C#N)c3)c2n1] |

-continued
| ID | Structure |
|---|---|
| Example 69 | 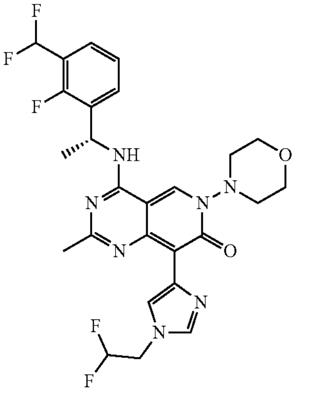 [SMILES: Cc1nc(N[C@H](C)c2cccc(C(F)F)c2F)c2cn(N3CCOCC3)c(=O)c(-c3cn(CC(F)F)cn3)c2n1] |
| Example 70 | 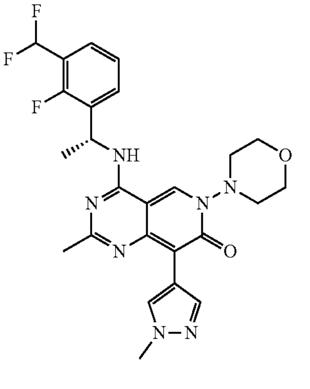 [SMILES: Cc1nc(N[C@H](C)c2cccc(C(F)F)c2F)c2cn(N3CCOCC3)c(=O)c(-c3cnn(C)c3)c2n1] |
| Example 71 | 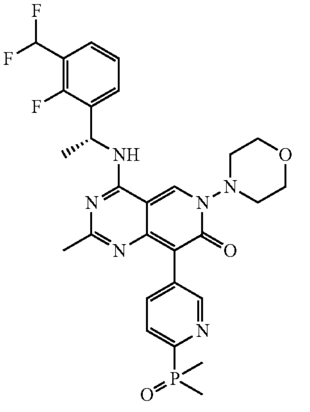 [SMILES: Cc1nc(N[C@H](C)c2cccc(C(F)F)c2F)c2cn(N3CCOCC3)c(=O)c(-c3ccc(P(C)(C)=O)nc3)c2n1] |
| Example 72 | 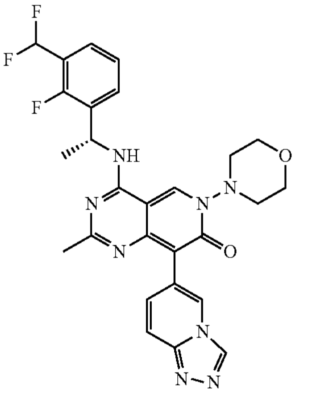 [SMILES: Cc1nc(N[C@H](C)c2cccc(C(F)F)c2F)c2cn(N3CCOCC3)c(=O)c(-c3ccc4nncn4c3)c2n1] |
| Example 73 | 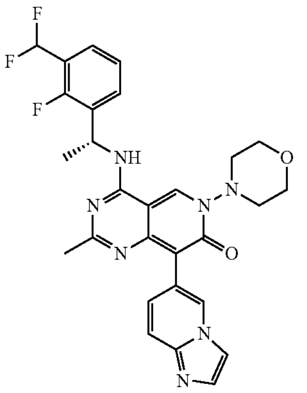 |
| Example 74 | 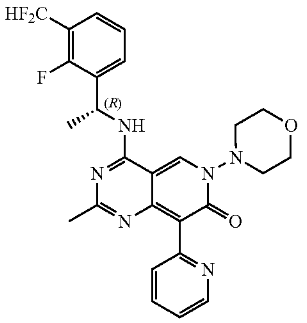 |
| Example 75 | 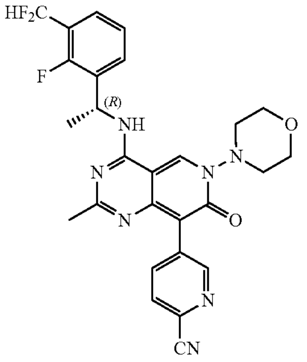 |
| Example 76 | 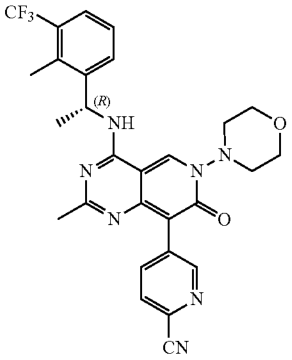 |

-continued
| ID | Structure |
|---|---|
| Example 77 | 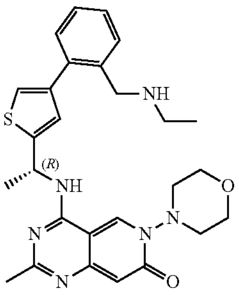 |
| Example 78 | 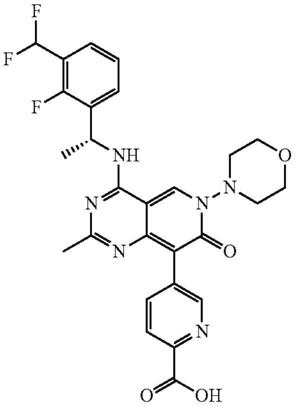 [SMILES: Cc1nc(N[C@H](C)c2cccc(C(F)F)c2F)c2cn(N3CCOCC3)c(=O)c(-c3ccc(C(=O)O)nc3)c2n1] |
| Example 79 | 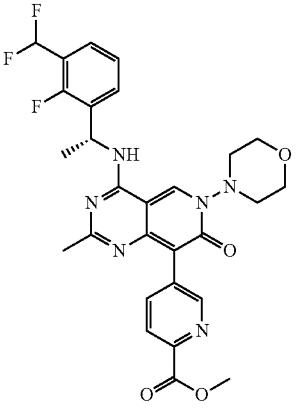 [SMILES: COC(=O)c1ccc(-c2c(=O)n(N3CCOCC3)cc3c(N[C@H](C)c4cccc(C(F)F)c4F)nc(C)nc23)cn1] |
| Example 80 | 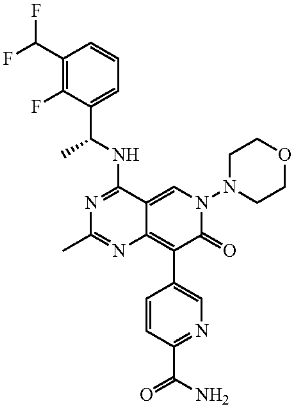 [SMILES: Cc1nc(N[C@H](C)c2cccc(C(F)F)c2F)c2cn(N3CCOCC3)c(=O)c(-c3ccc(C(N)=O)nc3)c2n1] |
-continued
| ID | Structure |
|---|---|
| Example 81 | 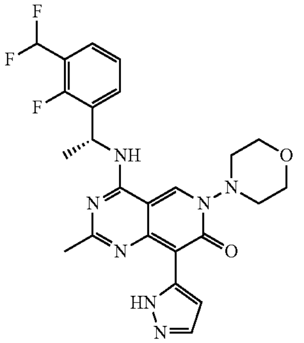 [SMILES: Cc1nc(N[C@H](C)c2cccc(C(F)F)c2F)c2cn(N3CCOCC3)c(=O)c(-c3ccn[nH]3)c2n1] |
| Example 82 | 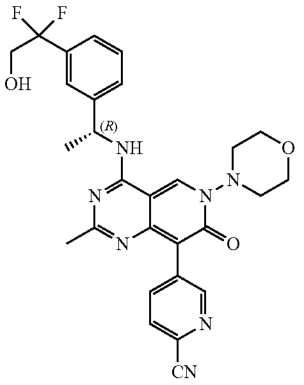 |
| Example 83 | 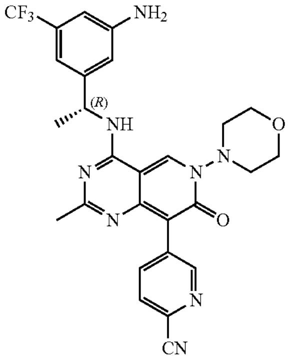 |
| Example 84 | 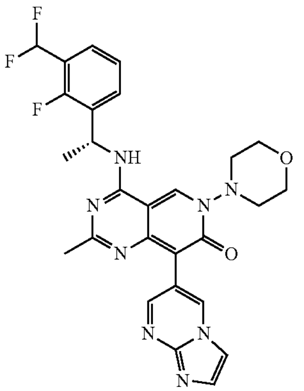 [SMILES: Cc1nc(N[C@H](C)c2cccc(C(F)F)c2F)c2cn(N3CCOCC3)c(=O)c(-c3cnc4nccn4c3)c2n1] |

-continued

| ID | Structure |
|---|---|
| Example 85 | 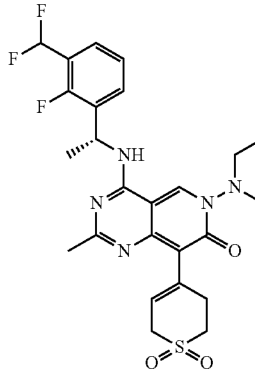 |
| Example 86 | 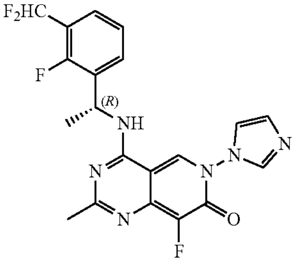 |
| Example 87 | 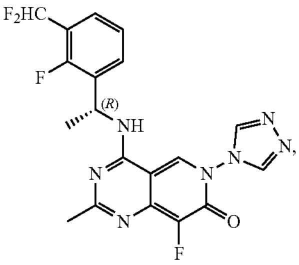, and |

or a pharmaceutically acceptable salt or a stereoisomer thereof.

15. A pharmaceutical composition comprising the compound of claim 1, or a pharmaceutically acceptable salt or a stereoisomer thereof, and a pharmaceutically acceptable carrier or excipient.

16. A method of treating a subject with a disease and/or a condition wherein the inhibition of the interaction of SOS1 and a RAS-family protein or RAC1 is of therapeutic benefit comprising administering to the subject a therapeutically effective amount of the compound of claim 1 or a pharmaceutically acceptable salt or a stereoisomer thereof.

17. A method of treating a subject with cancer comprising administering to the subject a therapeutically effective amount of the compound of claim 1 or a pharmaceutically acceptable salt or a stereoisomer thereof; wherein the cancer selected from the group consisting of pancreatic cancer, lung cancer, colorectal cancer, cholangiocarcinoma, multiple myeloma, melanoma, uterine cancer, endometrial cancer, thyroid cancer, acute myeloid leukaemia, bladder cancer, urothelial cancer, gastric cancer, cervical cancer, head and neck squamous cell carcinoma, diffuse large B cell lymphoma, oesophageal cancer, chronic lymphocytic leukemia, hepatocellular cancer, breast cancer, ovarian cancer, prostate cancer, glioblastoma, renal cancer and sarcoma.

18. The method of claim 17, wherein the compound or a pharmaceutically acceptable salt or a stereoisomer thereof is administered in combination with a therapeutically effective amount of at least one other pharmacologically active substance.

19. The method of claim 18, wherein the at least one other pharmacologically active substance is an inhibitor of MEK and/or of mutants thereof.

20. A compound, a pharmaceutically acceptable salt, or a stereoisomer thereof, wherein the compound is

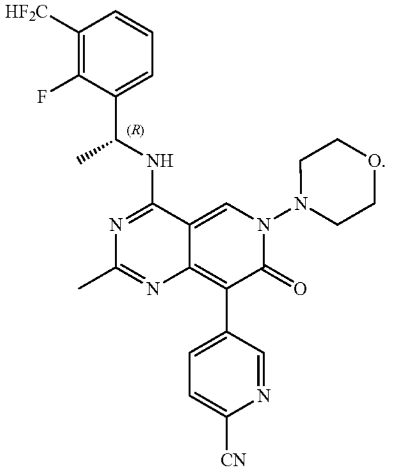

* * * * *